US009873896B2

(12) United States Patent
Slininger et al.

(10) Patent No.: US 9,873,896 B2
(45) Date of Patent: Jan. 23, 2018

(54) YEAST STRAINS

(71) Applicants: The United States of America, as represented by the Secretary of Agriculture, Washington, DC (US); Board of Trustees of Michigan State University, East Lansing, MI (US)

(72) Inventors: Patricia J. Slininger, Metamora, IL (US); Stephanie R. Thompson, Pekin, IL (US); Venkatesh Balan, Sugar Land, TX (US); Leonardo Da Costa Sousa, Lansing, MI (US); Bruce E. Dale, Mason, MI (US); Maureen A. Shea Andersh, Peoria, IL (US); Bruce S. Dien, Peoria, IL (US)

(73) Assignees: The United States of America, as represented by the Secretary of Agriculture, Washington, DC (US); Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/047,195

(22) Filed: Feb. 18, 2016

(65) Prior Publication Data

US 2016/0160241 A1 Jun. 9, 2016

Related U.S. Application Data

(62) Division of application No. 14/167,430, filed on Jan. 29, 2014, now Pat. No. 9,297,027.

(51) Int. Cl.
| | |
|---|---|
| C12P 7/06 | (2006.01) |
| C12P 7/04 | (2006.01) |
| C12P 7/02 | (2006.01) |
| C12P 7/00 | (2006.01) |
| C12P 1/02 | (2006.01) |
| C12P 1/00 | (2006.01) |
| C12P 7/08 | (2006.01) |
| C12P 7/10 | (2006.01) |
| C12N 1/14 | (2006.01) |
| C12R 1/84 | (2006.01) |

(52) U.S. Cl.
CPC ............... *C12P 7/10* (2013.01); *C12N 1/14* (2013.01); *C12R 1/84* (2013.01); *Y02E 50/16* (2013.01); *Y02E 50/17* (2013.01)

(58) Field of Classification Search
None
See application file for complete search history.

(56) References Cited

PUBLICATIONS

Agbogbo, Frank K. and Guillermo Coward-Kelly, "Cellulosic ethanol production using the naturally occurring xylose-fermenting yeast, *Pichia stipitis*", (2008) Biotechnology Letters 30:1515-1524.

Bajwa, Paramjit K. et al., "Mutants of the Pentose-Fermenting Yeast *Pichia stipitis* with Improved Tolerance to Inhibitors in Hardwood Spent Sulfite Liquor", (2009) Biotechnology and Bioengineering 104(5):892-900.

Bajwa, Paramjit K. et al., "Strain improvement of the pentose-fermenting yeast *Pichia stipitis* by genome shuffling", (2010) Journal of Microbiological Methods 81:179-186.

Balan, Venkatesh et al., "Lignocellulosic Biomass Pretreatment Using AFEX", (2009) In: Biofuels:Methods and Protocols, Methods in Moleclular Biology vol. 581 chapter 6 p. 61-77 J. Mielenz (Ed.) Springer LLC New York.

Brunenberg, Peter M. et al., "NADH-linked aldose reductase: the key to anaerobic alcoholic fermentation of xylose by yeasts", (1984) Applied Microbiology and Biotechnology19:256-260.

Hughes, Stephen R. et al., "Random UV-C mutagenesis of Scheffersomyces (formerly Pichia) stipitis NRRL Y-7124 to improve anaerobic growth on lignocellulosic sugars", (2012) Journal of Industrial Microbiology and Biotechnology 39:163-173.

Jin, Mingjie et al., "A novel integrated biological process for cellulosic ethanol production featuring high ethanol productivity, enzyme recycling and yeast cells reuse", (2012) Energy & Environmental Science 5:7168-7175.

Kurtzman, Cletus P. and Motofumi Suzuki, "Phylogenetic analysis of ascomycete yeasts that form coenzyme Q-9 and the proposal of the new genera *Babjeviella*, *Meyerozyma*, *Millerozyma*, *Priceomyces*, and *Scheffersomyces*", (2010) Mycoscience 51:2-14.

Nigam, J.N., "Development of xylose-fermenting yeast *Pichia stipitis* for ethanol production through adaptation on hardwood hemicellulose acid prehydrolysate", (2001) Journal of Applied Microbiology 90:208-215.

Nigam, J.N., "Ethanol production from wheat straw hemicellulose hydrolysate by Pichia stipitis", (2001) Journal of Biotechnology 87:17-27.

Slininger, P. J., "Comparative Evaluation of Ethanol Production by Xylose-Fermenting Yeasts Presented High Xylose Concentrations", (1985) Biotechnology Letters 7(6):431-436.

Slininger, P. J., "Optimum pH and Temperature Conditions for Xylose Fermentation by Pichia stipitis" (1990) Biotechnology and Bioengineering 35:727-731.

Slininger, P. J., "Nitrogen source and mineral optimization enhance D-xylose conversion to ethanol by the yeast *Pichia stipitis* NRRLY-7124" (2006) Applied Microbiology and Biotechnology 72:1285-1296.

Slininger, Patricia J. et al., "Culture Nutrition and Physiology Impact the Inhibitor Tolerance of the yeast *Pichia stipitis* NRRL Y-7124" (2009) Biotechnology and Bioengineering 102(3)778-790.

Slininger, Patricia J., "Repression of Xylose-Specific Enzymes by Ethanol in Scheffersomyces (Pichia) stipitis and Utility of Repitching Xylose-Grown Populations to Eliminate Diauxic Lag", (2011) Biotechnology and Bioengineering 108(8):1801-1815.

Ladisch, Michael R. and Karen Dyck, "Dehydration of Ethanol: New Approach Gives Positive Energy Balance", (1979), Science 205(4409):898-900.

*Primary Examiner* — Emily A Cordas
(74) *Attorney, Agent, or Firm* — David L. Marks; John D. Fado

(57) ABSTRACT

Several mutated strains of *Scheffersomyces stipitis* are generated by repetitive culturing of the parent strain on two types of concentrated hydrolyzates and with ethanol-challenged xylose-fed continuous culture. Isolates collected from various enriched populations are screened and ranked based on relative xylose uptake rate and ethanol yield. Ranking on hydrolyzates with and without nutritional supplementation is used to identify those isolates with best performance across diverse conditions.

2 Claims, 39 Drawing Sheets

YEAST STRAINS

BACKGROUND OF INVENTION

Field of Invention

This invention relates to novel strains of *Scheffersomyces stipitis* that are useful in converting plant sugars to ethanol.

Description of the Prior Art

An estimated 1.3 billion dry tons of lignocellulosic biomass could be available annually to support ethanol production at a level that would allow the U.S. to reduce its petroleum consumption by 30%. The fibrous, cell-wall material that is characteristic of lignocellulosic feedstocks is difficult to deconstruct and depolymerize into fermentable sugars. The chemical pretreatment required to open the structure of plant biomass to enzymatic hydrolysis results in solutions rich in glucose and xylose, but laden with byproducts that inhibit fermentation, including acetic acid, furfural, hydroxymethyl furfural, and others. Traditional industrial yeasts do not ferment xylose and are not able to survive, grow or ferment in toxic concentrated hydrolyzates which contain sugar concentrations high enough to support the greater than 40 g/L ethanol accumulations needed for economical recovery.

*Pichia stipitis* is known to ferment D-xylose to ethanol more efficiently than other native yeasts previously described (Prior, et al., *Process Biochemistry* 24(1), 21-32 (1989)). The *Pichia stipitis* that had been deposited at the USDA's ARS Culture Collection (deposit accession number NRRL Y-7124) was recently renamed *Scheffersomyces stipitis* (Kurtzman and Suzuki, *Mycoscience* 5(2), 2-14 (2010)) and is particularly useful because it has strong NADH-linked, as opposed to NADPH-linked, aldose reductase activity providing for a more favorable cofactor balance in the conversion of xylose to xylulose (Bruinenberg, et al., *Applied Micro. and Biotech.* 19, 256-260 (1984)). *S. stipitis* strain NRRL Y-7124 ferments hexoses and xylose to economically recoverable concentrations of ethanol exceeding 40 g/L with almost no accumulation of xylitol byproduct (Slininger, et al., *Biotechnology Letters* 7, 431-436 (1985); Slininger, et al., *Biotechnology and Bioengineering* 35, 727-731 (1990a); Slininger, et al., *Annals of the New York Academy of Science* 589, 25-40 (1990b)). In nutritionally optimized media, this *S. stipitis* strain is able to produce over 70 g/L ethanol in 40 hours (1.75 g/L/h) from 150 g/L sugars at a yield of 0.41±0.06 g/g and an ethanol productivity of 1.6 g/L/h in high density fermentations (6 g/L cells) (Slininger, et al. (1985); Slininger, et al., *Applied Microbiology and Biotechnology* 72, 1285-1296 (2006); Slininger, et al., *Biotechnology and Bioengineering* 108(8), 1801-1815 (2011)). Given appropriate nitrogen levels, it is also relatively resistant to fermentation inhibitors ethanol, furfural, and hydroxymethylfurfural (HMF) (Slininger, et al., *Biotechnology and Bioengineering* 102(3):778-790 (2009)). *Scheffersomyces stipitis* is one of the most viable native pentose-fermenting yeasts available for commercial scale-up, as reviewed by Agbogbo and Coward-Kelly (*Biotechnology Letters* 30, 1515-1524 (2008)) who point to the need to improve sugar uptake rate in biomass hydrolyzates, including reducing the effects of diauxy and improving ethanol and inhibitor tolerance. Thus, there is a need for novel strains of *S. stipitis* which are tolerant of diverse lignocellulosic hydrolyzates.

To improve the performance of this *Scheffersomyces stipitis* strain, various adaptation procedures are applied. These adaptation procedures include natural selection on hardwood hemicelluose acid prehydrolyzate (Nigam, *J. of Applied Microbiology* 90(2), 208-215 (2001a)) and wheat straw hemicelluloses hydrolyzate (Nigam, *J. of Biotechnology* 87(1), 17-27 (2001b)), UV-C mutagenesis and anaerobic environment selection to reduce oxygen requirement (Hughes, et al., *J. of Industrial Microbiology and Biotechnology* 39, 163-173 (2012)), and UV mutagenesis followed by genome shuffling and selective plating on hydrolyzate gradient plates to improve fermentation of waste sulfite liquor (Bajwa, et al., *Biotechnology and Bioengineering* 104, 892-900 (2009); Bajwa, et al., *J. of Microbiological Methods* 81, 179-186 (2010)). While these experiments suggest the potential utility of an adaptation approach to improving the functionality of *Scheffersomyces* strains for industrial application on lignocellulosic hydrolyzates, they do not describe the application of adapted strains of *S. stipitis* to hydrolyzates with sugar concentrations high enough to support economical ethanol production. Thus a need exists to generate adapted *S. stipitis* that can utilize highly concentrated sugar hydrolyzates so that ethanol production is affordable.

BRIEF DESCRIPTION OF THE INVENTION

It is an object of this invention to have a method of generating a novel *Scheffersomyces stipitis* strain having enhanced capability of producing ethanol from diverse hydrolyzates with diverse nutrient supplementation compared to the parent *S. stipitis* cells from which the novel *S. stipitis* strain is derived. This method has the steps of culturing the parent *S. stipitis* cells in a first medium and selecting one or more first *S. stipitis* isolates with desired characteristics that are superior to the parent *S. stipitis*. The first medium can be a medium containing low furfural concentration, low HMF concentration, high acetic acid concentration, and high nitrogen concentration (such as AFEX-CSH); a medium containing high xylose concentration and low glucose concentration (such as PSGHL); a medium containing high xylose concentration and high glucose concentration (such as SGH); or a medium containing approximately 15 g/L or more ethanol and high xylose concentration. It is another object of the invention that one can optionally irradiate the *S. stipitis* cells prior to or during culturing on the first medium.

It is another object of this invention to have a method of generating a novel *Scheffersomyces stipitis* strain having enhanced capability of producing ethanol from diverse hydrolyzates with diverse nutrient supplementation compared to the parent *S. stipitis* cells from which the novel *S. stipitis* strain is derived. This method has the steps of culturing the parent *S. stipitis* cells in a first medium, selecting one or more first *S. stipitis* isolates with desired characteristics that are superior to the parent *S. stipitis*, culturing the selected first *S. stipitis* isolate in a second medium, and selecting one or more second *S. stipitis* isolates with desired characteristics that are superior to the parent *S. stipitis*. Another object is that one can optionally irradiate the *S. stipitis* cells prior to or during culturing on the first medium and/or the second medium. The first medium and the second medium can be a medium containing low furfural concentration, low HMF concentration, high acetic acid concentration, and high nitrogen concentration (such as AFEX-CSH); a medium containing high xylose concentration and low glucose concentration (such as PSGHL); a medium containing high xylose concentration and high glucose concentration (such as SGH); or a medium containing approximately 15 g/L or more ethanol and high xylose concentration, so long as the first medium and second medium are not the same media.

It is a further object of this invention to have a method of generating a novel *Scheffersomyces stipitis* strain having enhanced capability of producing ethanol from diverse hydrolyzates with diverse nutrient supplementation compared to the parent *S. stipitis* cells from which the novel *S. stipitis* strain is derived. This method has the steps of culturing the parent *S. stipitis* cells in a first medium, selecting one or more first *S. stipitis* isolates with desired characteristics that are superior to the parent *S. stipitis*, culturing the selected first *S. stipitis* isolate in a second medium, selecting one or more second *S. stipitis* isolates with desired characteristics that are superior to the parent *S. stipitis*, culturing the selected second *S. stipitis* isolate in a third medium, and selecting one or more third *S. stipitis* isolates with desired characteristics that are superior to the parent *S. stipitis*. Another object of this invention is that one can optionally irradiate the *S. stipitis* cells prior to or during culturing on the first medium and/or the second medium and/or the third medium. The first medium, the second medium, and the third medium can be a medium containing low furfural concentration, low HMF concentration, high acetic acid concentration, and high nitrogen concentration (such as AFEX-CSH); a medium containing high xylose concentration and low glucose concentration (such as PSGHL); a medium containing high xylose concentration and high glucose concentration (such as SGH); or a medium containing approximately 15 g/L or more ethanol and high xylose concentration, so long as the first medium, the second medium, and the third medium are not the same media.

It is still a further object of this invention to have a method of generating a novel *Scheffersomyces stipitis* strain having enhanced capability of producing ethanol from diverse hydrolyzates with diverse nutrient supplementation compared to the parent *S. stipitis* cells from which the novel *S. stipitis* strain is derived. This method has the steps of culturing the parent *S. stipitis* cells in a first medium, selecting one or more first *S. stipitis* isolates with desired characteristics that are superior to the parent *S. stipitis*, culturing the selected first *S. stipitis* isolate in a second medium, selecting one or more second *S. stipitis* isolates with desired characteristics that are superior to the parent *S. stipitis*, culturing the selected second *S. stipitis* isolate in a third medium, selecting one or more third *S. stipitis* isolates with desired characteristics that are superior to the parent *S. stipitis*, culturing the selected third *S. stipitis* in a fourth medium, and selecting one or more fourth *S. stipitis* isolates with desired characteristics that are superior to the parent *S. stipitis*. Another object of this invention is that one can optionally irradiate the *S. stipitis* cells prior to or during culturing on the first medium and/or the second medium and/or the third medium and/or the fourth medium. The first medium, the second medium, the third medium and the fourth medium can be a medium containing low furfural concentration, low HMF concentration, high acetic acid concentration, and high nitrogen concentration (such as AFEX-CSH); a medium containing high xylose concentration and low glucose concentration (such as PSGHL); a medium containing high xylose concentration and high glucose concentration (such as SGH); or a medium containing approximately 15 g/L or more ethanol and high xylose concentration, so long as the first medium, the second medium, the third medium, and the fourth medium are not the same media.

It is an object of this invention to have a novel and isolated *S. stipitis* strain produced by the methods described above such that the novel and isolated *S. stipitis* strain is tolerant of diverse nutritional environments and is capable of producing ethanol from diverse hydrolyzates. It is a further object of this invention that the novel and isolated *S. stipitis* strain has reduced diauxic lag in the presence of approximately 15 g/L or more ethanol or in another embodiment, approximately 20 g/L or more ethanol.

It is an object of this invention to have a novel and isolated *S. stipitis* strain produced by the methods described above such that the novel and isolated *S. stipitis* strain is tolerant of diverse nutritional environments and is capable of producing ethanol from diverse hydrolyzates. It is a further object of this invention that the novel and isolated *S. stipitis* has a shorter lag preceding growth phase, more rapid initial growth, and more rapid glucose and xylose uptakes for conversion to ethanol in lignocellulosic biomass hydrolyzates compared to the parent *S. stipitis*. It is an optional object of this invention that the novel and isolated *S. stipitis* has reduced diauxic lag in the presence of approximately 15 g/L or more ethanol or in another embodiment, approximately 20 g/L or more ethanol.

It is an object of this invention to have a novel and isolated *S. stipitis* strain produced by the methods described above such that the novel and isolated *S. stipitis* strain is tolerant of diverse nutritional environments and is capable of producing ethanol from diverse hydrolyzates. It is a further object of this invention that the novel and isolated *S. stipitis* has higher ethanol production using xylose from hydrolyzates compared to the parent *S. stipitis*. It is an optional object of this invention that the novel and isolated *S. stipitis* has a shorter lag preceding growth phase, more rapid initial growth, and more rapid glucose and xylose uptakes for conversion to ethanol in lignocellulosic biomass hydrolyzates compared to the parent *S. stipitis*. It is another optional object of this invention that the novel and isolated *S. stipitis* has reduced diauxic lag in the presence of approximately 15 g/L or more ethanol or in another embodiment, approximately 20 g/L or more ethanol.

It is an object of this invention to have a novel and isolated *S. stipitis* strain produced by the methods described above such that the novel and isolated *S. stipitis* strain is tolerant of diverse nutritional environments and is capable of producing at least approximately 40 g/L ethanol from diverse hydrolyzates. It is an optional object of this invention that the novel and isolated *S. stipitis* has higher ethanol production using xylose from hydrolyzates compared to the parent *S. stipitis*. It is another optional object of this invention that the novel and isolated *S. stipitis* has a shorter lag preceding growth phase, more rapid initial growth, and more rapid glucose and xylose uptakes for conversion to ethanol in lignocellulosic biomass hydrolyzates compared to the parent *S. stipitis*. It is a further optional object of this invention that the novel and isolated *S. stipitis* has reduced diauxic lag in the presence of approximately 15 g/L or more ethanol or in another embodiment, approximately 20 g/L or more ethanol.

It is an object of this invention to have a novel and isolated *S. stipitis* strain produced by the methods described above such that the novel and isolated *S. stipitis* strain is tolerant of diverse nutritional environments and is capable of producing ethanol from diverse hydrolyzates. It is a further object of this invention that the novel and isolated *S. stipitis* strain produces higher quantity of ethanol than the parent *S. stipitis* strain when cultured on lignocellulosic biomass. It is an optional object of this invention that the isolated *S. stipitis* strain is capable of producing approximately 40 g/L or more ethanol from diverse hydrolyzates. It is another optional object of this invention that the novel and isolated *S. stipitis* has higher ethanol production using xylose from hydrolyzates compared to the parent *S. stipitis*. It is another optional object of this invention that the novel and isolated *S. stipitis* has a shorter lag preceding growth phase, more rapid initial growth, and more rapid glucose and xylose uptakes for conversion to ethanol in lignocellulosic biomass hydrolyzates compared to the parent *S. stipitis*. It is a further optional object of this invention that the novel and isolated *S. stipitis* has reduced diauxic lag in the presence of approximately 15 g/L or more ethanol or in another embodiment, approximately 20 g/L or more ethanol. It is a further object of this invention that the lignocellulosic biomass can be either woody biomass or herbaceous biomass. It is still another optionally object of this invention that the herbaceous biomass can be AFEX-CSH, PSGHL, or SGH.

It is an object of this invention to have a novel and isolated *S. stipitis* strain produced by the methods described above such that the novel and isolated *S. stipitis* strain is tolerant of diverse nutritional environments, is capable of producing ethanol from diverse hydrolyzates, and is *S. stipitis* ARS patent deposit accession number NRRL Y-50857, *S. stipitis* ARS patent deposit accession number NRRL Y-50858, *S. stipitis* ARS patent deposit accession number NRRL Y-50859, *S. stipitis* ARS patent deposit accession number NRRL Y-50860, *S. stipitis* ARS patent deposit accession number NRRL Y-50861, *S. stipitis* ARS patent deposit accession number NRRL Y-50862, *S. stipitis* ARS patent deposit accession number NRRL Y-50863, *S. stipitis* ARS patent deposit accession number NRRL Y-50864, *S. stipitis* ARS patent deposit accession number NRRL Y-50865, *S. stipitis* ARS patent deposit accession number NRRL Y-50871, *S. stipitis* ARS patent deposit accession number NRRL Y-50872, *S. stipitis* ARS patent deposit accession number NRRL Y-50873, *S. stipitis* ARS patent deposit accession number NRRL Y-50874, or a combination thereof.

It is an object of this invention to have a method for producing ethanol comprising growing the novel and isolated *S. stipitis* cells produced by one or more of the methods described above on a culture medium containing glucose and xylose for a period of time effective to allow the *S. stipitis* cells to grow on one or both sugars and to ferment both sugars to ethanol. In another embodiment of this invention, the culture medium contains a hydrolyzate of a lignocellulosic material.

It is another object of this invention to have a novel and isolated *S. stipitis* strain capable of producing ethanol from glucose and xylose such that the novel and isolated *S. stipitis* strain has improved capability to produce ethanol from lignocellulosic biomass compared to the parental strain *S. stipitis* ARS Culture Collection accession number NRRL Y-7124. In an optional embodiment of this invention, the novel and isolated *S. stipitis* strain is more tolerant of diverse hydrolyzates and diverse nutritional environments compared to the parent *S. stipitis* NRRL Y-7124. In another optional embodiment of this invention, the novel and isolated *S. stipitis* strain has reduced diauxic lag during sugar transition from glucose to xylose compared to the parental *S. stipitis* NRRL Y-7124. In a further optional embodiment, the novel and isolated *S. stipitis* strain has reduced diauxic lag during sugar transition from glucose to xylose occurs in the presence of approximately 15 g/L or more ethanol in one embodiment or approximately 20 g/L or more ethanol in another embodiment. In yet another optional embodiment of this invention, the novel and isolated *S. stipitis* strain is capable of producing approximately 30 g/L or more ethanol in one embodiment, approximately 35 g/L or more ethanol in another embodiment, or approximately 40 g/L or more ethanol in a third embodiment, on diverse hydrolyzate.

It is another object of this invention to have a novel and isolated *S. stipitis* strain capable of producing ethanol from glucose and xylose such that the novel and isolated *S. stipitis* strain has improved capability to produce ethanol from lignocellulosic biomass compared to the parental strain *S. stipitis* ARS Culture Collection accession number NRRL Y-7124. It is further object of this invention that the novel and isolated *S. stipitis* strain is *S. stipitis* ARS patent deposit accession number NRRL Y-50857, *S. stipitis* ARS patent deposit accession number NRRL Y-50858, *S. stipitis* ARS patent deposit accession number NRRL Y-50859, *S. stipitis* ARS patent deposit accession number NRRL Y-50860, *S. stipitis* ARS patent deposit accession number NRRL Y-50861, *S. stipitis* ARS patent deposit accession number NRRL Y-50862, *S. stipitis* ARS patent deposit accession number NRRL Y-50863, *S. stipitis* ARS patent deposit accession number NRRL Y-50864, *S. stipitis* ARS patent deposit accession number NRRL Y-50865, *S. stipitis* ARS patent deposit accession number NRRL Y-50871, *S. stipitis* ARS patent deposit accession number NRRL Y-50872, *S. stipitis* ARS patent deposit accession number NRRL Y-50873, *S. stipitis* ARS patent deposit accession number NRRL Y-50874, or a combination thereof.

It is an object of this invention to have a method of generating a novel *S. stipitis* strain having enhanced capability of producing ethanol from glucose and xylose compared to the parent *S. stipitis* cells from which the novel *S. stipitis* strain is derived, the method being culturing the parent *S. stipitis* on a first medium; selecting first *S. stipitis* cells having at least a first desired characteristic superior to the parent *S. stipitis* strain; culturing the selected first *S. stipitis* cells on a second medium; selecting second *S. stipitis* cells having at least a second desired characteristic superior to the parent *S. stipitis* strain; optionally culturing the second *S. stipitis* cells on a third medium; optionally selecting third *S. stipitis* cells having at least a third desired characteristic superior to the parent *S. stipitis* strain; optionally culturing the third *S. stipitis* cells on a fourth medium; and optionally selecting fourth *S. stipitis* cells having at least a fourth desired characteristic superior to the parent *S. stipitis* strain; such that the first medium, the second medium, the third medium, and the fourth medium can be either AFX-CSH, PSGHL, SGH, or a high ethanol concentration and high xylose concentration medium; and such that the first medium, second medium, third medium, and fourth medium are different and distinct from each other. Another object of this invention is that one can optionally irradiate the *S. stipitis* cells prior to or during culturing on the first medium and/or the second medium and/or the third medium and/or the fourth medium. It is another object of this invention to have a novel and isolated *S. stipitis* strain generated by this method.

BRIEF DESCRIPTION OF THE FIGURES

FIG. 2A and FIG. 2B are biomass (square), glucose (circle with dashed line), xylose (circle with solid line), ethanol (triangle), and xylitol (diamond).

Figure 1:
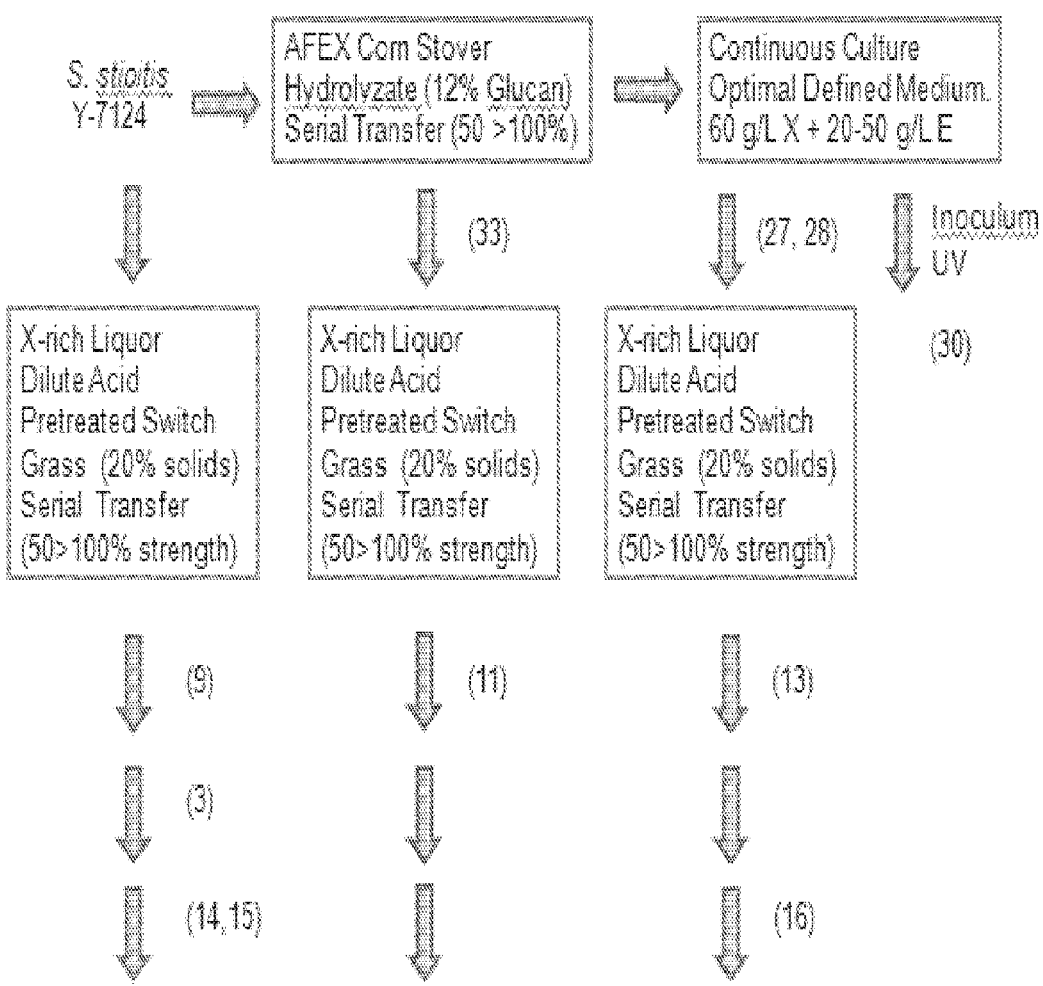
FIG. 1 illustrates an adaptation flow chart indicating the stresses applied and the points of recovery of superior isolates (numbers in parenthesis).

STATEMENT REGARDING DEPOSIT OF BIOLOGICAL MATERIAL UNDER THE TERMS OF THE BUDAPEST TREATY

On or before Sep. 24, 2013, the inventors deposited samples of the biological materials, described in Table 1 and that is the subject matter of this patent application, with the U.S.D.A., Agricultural Research Service's Patent Culture Collection located at the National Center for Agricultural Utilization Research, 1815 N. University Street, Peoria, Ill. 61604, in a manner affording permanence of the deposit and ready accessibility thereto by the public if a patent is granted. These deposits have been made under the terms of the Budapest Treaty on the International Recognition of the Deposit of Microorganisms for the Purposes of Patent Procedure and the regulations thereunder.

TABLE 1

| Name | Isolate Designation | ARS Patent Deposit Accession Number |
| --- | --- | --- |
| Scheffersomyces stipitis | 2A.1.53.R S100E40-1 | NRRL Y-50857 |
| Scheffersomyces stipitis | Y7124-10 | NRRL Y-50858 |
| Scheffersomyces stipitis | Y7124-6 | NRRL Y-50859 |
| Scheffersomyces stipitis | 2A.1.53R-1 | NRRL Y-50860 |
| Scheffersomyces stipitis | 2A.1.53R-E20-C1 | NRRL Y-50861 |
| Scheffersomyces stipitis | 2A.1.53R-E30-C3 | NRRL Y-50862 |
| Scheffersomyces stipitis | Y7124 GP-5 | NRRL Y-50863 |
| Scheffersomyces stipitis | 2A.30R-E40-C5 | NRRL Y-50864 |
| Scheffersomyces stipitis | Colony 5 GP-6 | NRRL Y-50865 |
| Scheffersomyces stipitis | Colony 5 | NRRL Y-50871 |
| Scheffersomyces stipitis | Colony 1 | NRRL Y-50872 |
| Scheffersomyces stipitis | Colony 7 | NRRL Y-50873 |
| Scheffersomyces stipitis | Y7124 S90E40-1 | NRRL Y-50874 |

All restrictions on the availability to the public of the a particular above listed biological material which has been deposited as described herein will be irrevocably removed upon the granting of a patent covering that particular biological material.

The biological materials identified herein have been deposited under conditions such that access to the microorganisms are available during the pendency of the patent application to one determined by the Commissioner to be entitled thereto under 37 C.F.R. § 1.14 and 35 U.S.C § 122.

The deposited biological material will be maintained with all the care necessary to keep them viable and uncontaminated for a period of at least five years after the most recent request for the furnishing of a sample of the deposited microorganism, and in any case, for a period of at least thirty (30) years after the date of deposit for the enforceable life of the patent, whichever period is longer.

We, the inventors for the invention described in this patent application, hereby declare further that all statements regarding this Deposit of the Biological Material made on information and belief are believed to be true and that all statements made on information and belief are believed to be true, and further that these statements are made with knowledge that willful false statements and the like so made are punishable by fine or imprisonment, or both, under section 1001 of Title 18 of the United States Code and that such willful false statements may jeopardize the validity of the instant patent application or any patent issuing thereon.

DETAILED DESCRIPTION OF THE INVENTION

Because a need for novel strains of S. stipitis which are tolerant of diverse lignocellulosic hydrolyzates exists, selective pressure is used to create novel strains of S. stipitis that are more tolerant of diverse lignoscellulosic hydrolyzates. In one embodiment of this invention, the method of generating S. stipitis with the desired phenotypes involves culturing S. stipitis serially under four different conditions. One can use culture conditions in any order to generate S. stipitis having the phenotypes described herein. The culture conditions are, in no particular order, (1) media having low levels of furan aldehyde, inhibitory levels of acetic acid, and high quantities of nitrogen sources (AFEX-CSH is one example of this type of media); (2) media having high levels of furan aldehyde, high levels of acetic acid, high levels of xylose, low levels of glucose, and low quantities of nitrogen sources (with or without nitrogen source supplementation) (PSGHL is one example of this type of media); (3) media having high levels of furan aldehyde, high levels of acetic acid, high levels of xylose, high levels of glucose, and low quantities of nitrogen sources (with or without nitrogen source supplementation) (SGH is one example of this type of media); and (4) high levels of ethanol and high levels of xylose. In another embodiment of this invention, one can generate S. stipitis with one or more desired phenotype by culturing the cells in any one or two or three of the above mentioned culture conditions, again in any order. The examples and descriptions infra describe one possible method of this invention. The desired phenotype includes one or more of the following: an ability to produce high levels of ethanol (at least approximately 20 g/L; at least approximately 25 g/L; at least approximately 30 g/L; at least approximately 35 g/L; at least approximately 40 g/L); an ability to use xylose to produce ethanol; an ability to produce ethanol from diverse hydrolyzates with different nutritional levels; ability to produce ethanol from lignocellulosic biomass; an ability to produce ethanol from woody biomass; an ability to produce ethanol from herbaceous biomass; a reduced diauxic lag during sugar transition (from glucose to xylose) in presence of ethanol (at least approximately 15 g/L; at least approximately 20 g/L); and ability to produce ethanol even in the presence of inhibitors (including, but not limited to, furan aldehyde, acetic acid, ethanol, poor nitrogen levels and poor nutrient levels). The indicated levels of these desired phenotypes are compared to the parental S. stipitis' phenotype.

Two different types of industrially promising hydrolyzate are selected for application in the adaptation process. The chemical pretreatment process, ammonia fiber explosion (AFEX), can be combined with subsequent enzymatic saccharification of the exposed cellulose to yield a concentrated sugar solution from crop biomass, such as corn stover. AFEX corn stover hydrolyzate (AFEX-CSH) is significantly lower in furan aldehyde inhibitors, but still contains inhibitory levels of acetic acid, and likely other byproducts of the reaction (Balan, et al., *Lignocellulosic Biomass Pretreatment Using AFEX*, in Mielenz (ed.), *Biofuels: Methods and Protocols, Methods in Molecular Biology* 581, 61-77 Humana Press (2009); Jin, et al., *Energy and Environmental Science* 5, 7168-7175 (2012)). AFEX-CSH is a useful starting material for adaptation, not only because of its lack of inhibitory furans and relatively low levels of acetic acid, but also because of its high content of the nitrogen sources ammonia and amino acids which have been recognized as important to supporting xylose fermentation by native pentose fermenting yeast S. stipitis strain USDA deposit accession number NRRL Y-7124 (Slininger, et al. (2006)) and genetically engineered *Saccharomyces* (Wang, et al., *Biotechnology and Bioengineering* doi:10.1002/bit.24992 (2013)). Another industrially important type of hydrolyzate is enzymatically saccharified dilute acid-pretreated postfrost switchgrass hydrolyzate (SGH). In contrast to AFEX-CSH, SGH is characterized by high contents of furan aldehydes and acetic acid, but very low levels of available nitrogen needed to support yeast growth and fermentation (see Table 2). Pretreated switchgrass hydrolyzate liquor (PSGHL), is the liquid in association with the pre-treated biomass prior to enzyme saccharification, and it is rich in xylose and low in glucose (see Table 2). Thus, PSGHL is a useful enrichment medium to force selection for improved xylose utilization in hydrolyzates, a failing point for many yeasts tried in the past. The low available nitrogen content of the switchgrass hydrolyzates provides an opportunity to explore the utility of nitrogen supplementation in the process of screening and ranking improved strains of S. stipitis.

TABLE 2

Compositions of hydrolyzates used in cultivations[1]

| | AFEX-pretreated corn stover hydrolyzate | | | | Dilute acid-pretreated switchgrass hydrolyzates (20% solids) | | | | | | |
| --- | --- | --- | --- | --- | --- | --- | --- | --- | --- | --- | --- |
| | 6% Glucan | | 12% Glucan | | PSGHL | | SGH | | SGH-N1 | | SGH-N2 | |
| Component | Mean | s | Mean | s | Mean | s | Mean | s | Mean | s | Mean | s |
| Glucose (g/L) | 58.9 | 9.0 | 107.4 | 16.7 | 7.9 | 2.5 | 69.2 | 3.2 | 67.4 | 6.5 | 64.2 | 1.3 |
| Xylose (g/L) | 34.2 | 7.3 | 48.7 | 15.8 | 52.1 | 5.1 | 48.6 | 2.7 | 45.3 | 3.5 | 47.4 | 0.8 |

TABLE 2-continued

Compositions of hydrolyzates used in cultivations[1]

| | AFEX-pretreated corn stover hydrolyzate | | | | Dilute acid-pretreated switchgrass hydrolyzates (20% solids) | | | | | | | |
|---|---|---|---|---|---|---|---|---|---|---|---|---|
| | 6% Glucan | | 12% Glucan | | PSGHL | | SGH | | SGH-N1 | | SGH-N2 | |
| Component | Mean | s | Mean | s | Mean | s | Mean | s | Mean | s | Mean | s |
| Arabinose (g/L) | 4.3 | 0.6 | 9.5 | 0.4 | 7.6 | 0.9 | 6.1 | 0.3 | 4.4 | 0.7 | 7.6 | 0.2 |
| Galactose (g/L) | 3.1 | 0.3 | 5.7 | 0.6 | 3.0 | 0.7 | 5.2 | 0.3 | 5.2 | 0.3 | 5.2 | 0.3 |
| Fructose (g/L) | 4.0 | 1.7 | 8.2 | 3.0 | 0.9 | 0.4 | 0.7 | 0 | 0.7 | 0 | 0.7 | 0 |
| Mannose (g/L) | 1.0 | 0.1 | 2.0 | 0.2 | 8.9 | 5.1 | 0 | 0 | 0 | 0 | 0 | 0 |
| Acetic Acid (g/L) | 1.8 | 0.2 | 4.7 | 1.0 | 6.1 | 2.8 | 5.4 | 0.4 | 4.3 | 0.6 | 5.8 | 0.3 |
| HMF (mM) | 0.3 | 0.5 | 1.1 | 1.5 | 2.8 | 3.1 | 1.8 | 0.2 | 1.1 | 1.3 | 3.6 | 0.5 |
| Furfural (mM) | 0.2 | 0.1 | 0.4 | 0.0 | 24.4 | 7.6 | 18.3 | 4.5 | 24.5 | 4.5 | 19.1 | 0.8 |
| PAN (mg N/L) | 318.7 | 49.9 | 493.2 | 69.1 | 33.7 | 15.6 | 69.9 | 14.7 | 188.0 | 4.0 | 173.0 | 22.0 |
| Urea (mg N/L) | 83.1 | 29.3 | 105.5 | 9.1 | 0.7 | 0.7 | 7.0 | 2.7 | 1101.0 | —[2] | 962.0 | 105.0 |
| Ammonia (mg N/L) | 1193.4 | 289.7 | 2707.6 | 385.6 | 25.0 | 21.0 | 23.0 | 24.6 | | | 369.0 | 63.0 |

[1]Values are reported in terms of mean and standard deviation (s) across hydrolyzates used in exampled reported.
[2]No values of s because N content is calculated based on urea addition.
Abreviations:
HMF = hydroxymethylfurfural;
PAN = Primary amino nitrogen;
PSGHL = Pretreated switchgrass hydrolyzate liquor;
SGH = switchgrass hydrolyzate; or with nutrient supplements -N1 or -N2.

Each of the three hydrolyzates (media) described herein, AFEX-CSH, PSGHL, and SGH, can include nutrient supplemented hydrolyzates and hydrolyzates that are not nutrient supplemented, unless clearly specified otherwise in the sentence or paragraph. While AFEX-CSH, PSGHL, and SGH are used in the examples herein, any hydrolyzate from lignocellulosic biomass, whether chemically or biocatalytically produced and whether herbaceous biomass or woody biomass, can be used instead of AFEX-CSH, PSGHL, and/or SGH, so long as the other hydrolyzate contains similar nutrient concentrations and/or inhibitor concentrations as the hydrolyzate that it is replacing. Further, any artificial media having similar nutrient concentrations and/or inhibitor concentrations can replace the hydrolyzates described herein. The media can be nutrient-enriched or non-enriched, as the hydrolyzates used herein. See Table 2, supra. Alternatively, a hydrolyzate or medium equivalent to AFEX-CHS contains, at a minimum, low furfural concentration (less than or equal to approximately 5 mM in one embodiment; less than or equal to approximately 3 mM in another embodiment; less than or equal to approximately 1 mM in a third embodiment); low HMF concentration (less than or equal to approximately 2 mM in one embodiment; less than or equal to approximately 1 mM in another embodiment); high acetic acid concentration (equal or greater than approximately 1 g/L in one embodiment; equal to or greater than approximately 2 g/L in another embodiment; equal to or greater than approximately 4 g/L in a third embodiment); and high nitrogen concentration (carbon to nitrogen molar ratio (C:N) between approximately 10:1 and approximately 130:1 in one embodiment; between approximately 20:1 and approximately 100:1 in another embodiment; in combination with equal to or greater than approximately 140 mg/L primary amino nitrogen in one embodiment; equal to or greater than approximately 170 mg/L primary amino nitrogen in another embodiment). A hydrolyzate or medium equivalent to PSGHL contains, at a minimum, high xylose concentration (equal to or greater than approximately 20 g/L in one embodiment; equal to or greater than approximately 15 g/L in another embodiment) and low glucose concentration (less than or equal to approximately 30 g/L in one embodiment; less than or equal to approximately 25 g/L in another embodiment). A hydrolyzate or medium equivalent to SGH contains, at a minimum, high xylose concentration (equal to or greater than approximately 20 g/L in one embodiment; equal to or greater than approximately 15 g/L in another embodiment) and high glucose concentration (equal to or greater than approximately 25 g/L in one embodiment; equal to or greater than approximately 30 g/L in another embodiment). Alternative hydrolyzates to AFEX-CSH, PSGHL, and SGH are well-known to one of ordinary skill in the art and can be supplemented with nutrients or not.

Both AFEX-CSH and PSGHL are used in sequence and in parallel as challenging selective media to force the evolution of *S. stipitis* toward derivatives with enhanced ability to grow and ferment in diverse hydrolyzates. The repetitive culturing and retrieval of functional populations from increasingly concentrated hydrolyzate environments is the general strategy to be accomplished in microplates employing a dilution series of 12% glucan AFEX-CSH or PSGHL prepared at 20% solids loading. This strategy utilizes natural selection and enrichment to recover spontaneous hydrolyzate inhibitor tolerant derivatives of USDA deposit accession number NRRL Y-7124.

Ethanol-challenged continuous culture is used to further enhance and stabilize AFEX-CSH adapted populations. Ethanol-challenged xylose growth and fermentation are targeted to enrich for populations able to resist ethanol damage, grow and survive on xylose as a sole carbon source and able to induce xylose-specific enzymes, thereby allowing fermentation of xylose to ethanol even in the presence of high levels of ethanol. Slininger, et al. (2011) demonstrated that ethanol concentrations approximately 15 to approximately 50 g/L progressively repressed enzyme inductions specific to xylose utilization. The resulting populations enriched in ethanol-tolerant derivatives of the AFEX-CSH tolerant population are subjected to further enrichment on PSGHL to broaden the functionality of strains in various types of hydrolyzates.

Once adaptations are completed, isolates are evaluated. Adapted individuals from populations occurring at various phases of adaptation are obtained by enrichment under target stress conditions followed by dilution plating to skim the most prevalent populations from which to pick colonists. Selected colonists are then ranked using dimensionless relative performance indices to determine best overall performance considering xylose uptake rate and ethanol yield on various hydrolyzates with or without nutrient supplementations. FIG. 1 provides a schematic overview of the adaptation processes used to obtain all tolerant S. stipitis strains, and indicates the screening numbers and points of isolation for superior ranking strains characterized by consistently high xylose consumption rates and high ethanol yields across all hydrolyzate formulations (see Table 2, supra) or extremely high, consistent performance on at least one type of hydrolyzate. On the basis of identical nucleotide sequences for domains D1/D2 of the large subunit rRNA gene using the protocol set forth in Kurtzman & Robnett (*Antonie van Leeuwenhoek* 73, 331-371 (1998)), all superior tolerant isolates are identified as *Scheffersomyces stipitis* and have been deposited in USDA's ARS Patent Culture Collection with the accession numbers listed in Table 3, and which lists the adaptation stresses applied during strain evolution, screening numbers, and isolate designation used in tables and figures.

TABLE 3

| Depository Accession Number | Screening number | Isolate designation | Adaptation stress |
|---|---|---|---|
| NRRL Y-50871 | 33 | Colony 5 | AFEX-CSH |
| NRRL Y-50872 | | Colony 1 | AFEX-CSH |
| NRRL Y-50873 | | Colony 7 | AFEX-CSH |
| NRRL Y-50861 | 27 | 2A.1.53R-E20-C1 | AFEX-CSH>E |
| NRRL Y-50862 | 28 | 2A.1.53R-E30-C3 | AFEX-CSH>E |
| NRRL Y-50864 | 30 | 2A.30R2-E40-C5 | AFEX-CSH>E (UV) |
| NRRL Y-50857 | 13 | 2A.1.53R S100E40-1 | AFEX-CSH>E>PSGHL |
| NRRL Y-50860 | 16 | 2A.1.53R-1 | AFEX-CSH>E>PSGHL |
| NRRL Y-50865 | 11 | Colony 5 GP-6 | AFEX-CSH>PSGHL |
| NRRL Y-50874 | 3 | Y7124 S90E40-1 | PSGHL |
| NRRL Y-50863 | 9 | Y7124 GP-5 | PSGHL |
| NRRL Y-50859 | 14 | Y7124-6 | PSGHL |
| NRRL Y-50858 | 15 | Y7124-10 | PSGHL |

AFEX-CSH = ammonia fiber explosion-pretreated corn stover enzyme hydrolyzate;
E = ethanol-fed continuous culture;
UV = ultra-violet light-treated inocula for E;
PSGHL = dilute acid pretreated switchgrass hydrolyzate liquor.

The S. stipitis mutants of this invention are significantly improved over the parent S. stipitis strain, USDA deposit accession number NRRL Y-7124, in accordance with high solids loading hydrolyzate screening targets and are able to produce >40 g/L ethanol in AFEX-CSH and in appropriately soy nitrogen-supplemented SGH. The evolved yeast strains will support lower cost production of renewable ethanol from agricultural biomass, reducing dependence on fossil fuels from petroleum.

For the examples, infra, a lyophilized culture of the parent strain S. stipitis is acquired from the ARS Culture Collection (National Center for Agricultural Utilization Research, Peoria, Ill.), deposit accession number NRRL Y-7124. Stock cultures of deposit accession number NRRL Y-7124 and its derivatives are maintained in 10% glycerol at −80° C. Glycerol stocks are used to inoculate Yeast Malt (YM) agar plates (comprised of 3 g/L Bacto-yeast extract (Becton Dickinson, Sparks, Md.), 3 g/L Bacto-malt extract (Becton Dickinson), 5 g/L Fluka Peptone Type IV from Soybeans (Sigma-Aldrich, St. Louis Mo.), 10 g/L dextrose (Fisher Scientific, Fair Lawn, N.J.) and 15 g/L Bacto-agar (Becton Dickinson)) which are incubated between approximately 48 hours and approximately 72 hours at 25° C. Developed plates are stored up to a week at 4° C. prior to use as liquid pre-culture inocula.

The following Optimal Defined Medium (ODM) composition which is optimized for ethanol production from high xylose concentration feeds (Slininger, et al. (2006)) is used in all precultures and growth cultures for inhibitor tolerance bioassays. Purines/Pyrimidines: 10 mg/L each of adenine, cytocine, guanine, uracil, and thymine. Macro-Minerals: 1 g/L $K_2HPO_4$, 1 g/L $KH_2PO_4$, and 0.75 g/L $MgSO_4.7H_2O$. Trace Minerals: 10 mg/L NaCl, 50 mg/L $FeSO_4.7H_2O$, 5.5 mg/L $ZnSO_4.7H_2O$, 1.6 mg/L $CoCl_2.6H_2O$, 12.5 mg/L $MnCl_2$, 5 mg/L $(NH_4)_6(Mo_7O_{24}).4H_2O$, 8 mg/L $CuSO_4.5H_2O$, 27.5 mg/L $CaCl_2$. $H_2O$, 250 mg/L EDTA. Vitamins: 0.5 mg/L each of biotin, thiamin, riboflavin, calcium pantothenate, niacin, pyridoxamine, and thioctic acid; and 0.05 mg/L each of folic acid and $B_{12}$. Carbon and Nitrogen Sources: The medium is originally optimized to accommodate efficient conversion of 150 g/L xylose with 0.15 M nitrogen supplied 80% by 3.56 g/L urea and 20% by amino acids (10 g/L DIFCO™ Vitamin-Assay Casamino Acids (product 228830; Sigma-Aldrich, St. Louis, Mo.)+0.1 g/L D,L-tryptophan (product T3300; Sigma-Aldrich, St. Louis, Mo.)+0.4 g/L L-cysteine (product C7352; Sigma-Aldrich, St. Louis, Mo.) (Slininger, et al., 2006). In certain instances as designated, the medium is applied at one-third the sugar and nitrogen source loadings—i.e., with 50 g/L xylose or glucose and 0.05 M nitrogen as amino acids and/or urea to maintain carbon:nitrogen at 33:1, which is near the optimal 37:1 ratio.

AFEX-pretreated corn stover hydrolyzate (AFEX-CSH) at 6% glucan and 12% glucan is prepared as follows. Corn stover harvested in September 2008 and grown from seed variety Pioneer 36H56 (triple stack-corn borer/rootworm/ROUNDUP® Ready (glyphosate resistant)) (DuPont Pioneer, Johnston, Iowa), is obtained from Arlington Research Station located in Wisconsin. The biomass size reduction is performed first by using a hammer mill (Christison Scientific LTD, Gateshead, England) followed by drying at room temperature until the moisture content of the biomass is <10% (dry weight basis). Then further fine milling is performed using a Thomas Model 4 Wiley® Mill (Swedesboro, N.J.) to 4 mesh size (0.5 cm) and are stored at 4° C. in a Zip-lock bags until further use. AFEX pretreatment is carried out using a 5 gallon high pressure stainless steel batch reactor purchased from Parr Company (Moline, Ill.) at Michigan Biotechnology Institute (MBI) pretreatment facility (Lansing, Mich.) according to the protocol in Balan, et. al. (2009). About 750 g of biomass is pretreated in a batch process. Biomass moisture content is raised to 60% by spraying de-ionized water onto the biomass, and the moistened biomass is then placed in the reactor. The reactor is charged with nitrogen, followed by pumping anhydrous liquid ammonia using an ammonia delivery system (comprising of an ammonia pump and a flow meter) into the reactor at 1:1 ammonia to biomass ratio. The reactor is then heated using a heating mantle until the temperature of the biomass reaches 100° C. (approximately 300 psi). This condition is maintained for approximately 30 minutes, after which the ammonia is released by venting. The pretreated biomass is then transferred to a plastic tray and dried in the hood overnight to remove residual ammonia present in the biomass. The AFEX treated biomass is then packed in a plastic Zip-lock bag and stored at 4° C. until further use.

AFEX-pretreated biomass is hydrolyzed at high solid loading (6% and 12% glucan loading) using commercial enzymes supplied by Novozymes (Franklinton, N.C.) and Genencor (Palo Alto, Calif.) at 30 mg/g of glucan enzyme loading (70% Ctec2, 15% Htec2 and 15% Multifect Pectinase). Enzyme hydrolysis is performed under sterile conditions using 2 L baffled shake flasks at 50° C., 250 rpm for 168 hours. The pH is maintained at 4.8 using 3 M HCL. Biomass is loaded in two (6%) to three (12%) batches during hydrolysis to overcome mixing problems caused by high viscosity during the initial stages of hydrolysis (Jin, et. al. (2012)). After the completion of hydrolysis, the hydrolyzate slurry is transferred to 1 L centrifuge tubes and is spun at 6000 rpm for 30 minutes to remove the solids from the liquid using BECKMAN AVANTI® centrifuge system (Brea, Calif.). The hydrolysed sugar stream (supernatant liquid) is sterile filtered using a 0.2 μm steri-cup membrane filtration system (Millipore, Billerica, Mass.) and stored at 4° C. until further use. The average compositions of 6% and 12% glucan hydrolyzate batches are given in Table 2, supra.

Dilute acid-pretreated switchgrass hydrolyzate liquor (PSGHL) is prepared as follows. Switchgrass hydrolyzates are prepared from Kanlow N1 baled post-frost from Mead, Nebr., that is milled to pass through a 2 mm screen. Switchgrass is pretreated at the 20% solids level by mixing 20 g dry weight of biomass with 80 mL of 0.936% (v/v) sulfuric acid solution and 0.3 g PLURONIC® F-68 (Sigma-Aldrich, St. Louis, Mo.). Each of 12 closed stainless steel vessels are loaded with reactants, are mounted in a Mathis AG Labomat IR Dyer Oven (Switzerland), are rotated at 50 rpm (1 minute right then 1 minute left), and are heated to 160° C., held for 15 minutes, and then cooled at 40° C. To prepare PSGHL, the pretreatment reaction products are centrifuged for 45 minutes at 7000 rpm and are sterile filtered through 0.2 μm NALGENE™ filter units (Thermo Fisher Scientific, Inc., Pittsburgh, Pa.). Supernates are combined and adjusted with $Ca(OH)_2$ to pH 6.0-6.5, and the resulting switchgrass pretreatment liquor (PSGHL) is filter sterilized and refrigerated at approximately 4° C. until ready for use.

To prepare enzyme-saccharified dilute acid pretreated switchgrass hydrolyzate (SGH), switchgrass is pretreated in the Labomat oven (Mathis AG, Switzerland) at the 20% solids level as described above. After pretreatment, the product is adjusted to pH 4.5 by adding 7.14 mL 15% $Ca(OH)_2$ solution and 4.5 mL 1 M citric acid buffer directly into each vessel and then tumbling 15 minutes in the Labomat. Pretreatment hydrolyzates are transferred to 250 mL Pyrex® bottles for saccharification. To each bottle, 2.7 mL of CTec and 0.5 mL of HTec enzymes (Novozyme, Franklinton, N.C.) are added. Tightly capped bottles are incubated approximately 72 hours at 50° C. and 175 rpm. Resulting hydrolyzates are sterile filtered through 0.2 μm NALGENE™ filter units (Thermo Fisher Scientific, Inc., Pittsburgh, Pa.) and are refrigerated at 4° C. until used. The resulting switchgrass hydrolyzate (SGH) is amended with the following nutrients then is filter sterilized for use in isolate performance screening: SGH-N1 (nutrient level 1)=SGH+6.66 g/L Casamino acids, 0.066 g/L tryptophan, 0.266 g/L cysteine+2.36 g/L urea+½ of liquid vitamin stock for Optimal Defined Medium (ODM) (prepared as described supra)+½ of dry $MgSO_4$ for ODM added prior to pH adjustment to 5.6+/−0.1 followed by filter sterilization of the finished hydrolyzate. SGH-N2 (nutrient level 2)=SGH is supplemented with soy flour (ADM Toasted Nutrisoy Flour, Product Code 063160, Decatur, Ill.) and urea to yield the nutrient levels set forth in Table 2, supra, and pH adjustment to approximately 5.75. The goal is to achieve amino and urea nitrogen content similar to that which was noted previously for *S. stipitis* USDA deposit accession number NRRL Y-7124 when the ODM sugar loading was approximately 100 g/L sugars (Slininger, et al. (2006)).

Cell biomass is measured by culture absorbance at 620 nm in 1 cm cuvettes using GENESYS™ 2 spectrophotometer (0.167 g/L biomass per unit absorbance) (ThermoFischer Scientific, Waltham, Mass.) or in microplates using POWERWAVE™ XS plate reader (Biotek Instruments, Inc., Winooski, Vt.). Samples are diluted as needed to obtain linear sensitivity to cell concentration. For 200 μL samples per well, the plate reader absorbance is 0.438× (GENESYS™ 2 absorbance). Unless otherwise specified, all absorbances are reported in terms of GENESYS™ 2 absorbance units. Viable cell counts are performed by serial dilutions of 100 μL cell suspension in 900 μL pH 7 buffer and are plated as four 10 μL spots onto YM agar plates to assess viable cell concentrations as colony forming units (cfu)/mL. For available nitrogen assays, enzyme-based test kits are used according to provided directions to assay primary amino nitrogen, ammonia and urea (Megazyme International Ireland Ltd., Wicklow, Ireland).

Quantitation of sugars, ethanol, furfural, HMF, and acetic acid in culture samples is performed by HPLC. Cell-free supernatants are stored at −20° C., then are thawed in cold water, and are diluted as needed prior to analysis. Sample concentrations are assessed using an HPLC (Waters, Corp., Milford, Mass.) containing a refrigerated WISP 717 Plus Autosampler at 10° C., 515 Pump, 2414 Refractive Index Detector and 2489 UV/VIS Detector (215 nm). Samples (10 μL) are injected onto Aminex HPX-87H ion exclusion column (Bio-Rad, Hercules, Calif.) fitted with a Microguard Cation H Micro-Guard Cartridge (125-0129) (Bio-Rad, Hercules, Calif.) and are eluted isocratically at 60° C. with acidified water (15 mM $HNO_3$) at 0.6 mL/minute. For hydrolyzate compositional analysis, Aminex HPX-87P carbohydrate analysis column (product number 125-0098) (with Deashing cartridge (product number 125-0118) and Carbo-P Micro-Guard Cartridge (product number 125-0119)) (Bio-Rad, Hercules, Calif.) are used at 80° C. with water mobile phase. For higher through-put analyses of isolate screenings in deep-well micro-plates, ethanol is evaluated using a Fast Acid Analysis column (product number 125-0100) (Bio-Rad, Hercules, Calif.) at 0.6 mL/minute acidified water mobile phase. Glucose and xylose are analyzed in microplates using a YSI 2900 Biochemistry Analyzer (YSI, Inc., Yellow Springs, Ohio).

Analysis of variance (ANOVA) and Student Newman Keuls (SNK) pairwise comparison analyses are performed using Sigmastat 3.5 (Systat Software, Inc., Chicago, Ill.) at significance criterion $P \leq 0.05$.

Example 1 AFEX-CSH Serial Transfer Culture Adaptation

A preculture of *S. stipitis* (USDA deposit accession number NRRL Y-7124) is inoculated by loop transfer of cells from YM agar to 75 mL ODM+150 g/L xylose to challenge growth under osmotic stress. Pre-cultures in 125 mL flasks with Bellco silicon sponge closures are incubated 24 hours at 25° C. with shaking (150 rpm, 1" orbit) (Bellco Glass, Inc., Vineland, N.J.).

Frozen aliquots of 6% AFEX-CSH and 12% glucan AFEX-CSH are thawed in cold water and are used at pH 5 to prepare a dilution series in 96 well microplates. Plates are filled with 50 μL per well and 8 wells per dilution, then inoculated with a few microliters of preculture per well to allow for an $A_{620,0} \geq 0.1$. Plates are statically incubated in a plastic box with a wet Wypall® for humidity at 25° C. for between approximately 24 and approximately 48 hours. Using the most concentrated hydrolyzate dilution in which *S. stipitis* grew, between approximately 1 and approximately 5 μL of the hydrolyzate and cells are transferred to each well of a new hydrolyzate dilution series ($A_{620,0} \geq 0.1$).

Cell growth is monitored by culture absorbance (620 nm) using a plate-reading spectrophotometer (POWERWAVE™ XS, Biotek Instruments, Inc., Winooski, Vt.). An uninoculated dilution series serves as a control and blank. Glycerol stocks of adaptation cultures are prepared at regular time intervals for subsequent isolation of improved strains or for use in reinoculating continuing hydrolyzate dilution series. The greatest hydrolyzate series concentration that was colonized is mixed 200 μL+800 μL 20% glycerol in duplicate cryovials for freezing at −80° C.

For isolation of single tolerant colonists, selected glycerol stocks of adaptation cultures are streaked to YM agar and are used to inoculate three microplate wells of 50 μL each 3% glucan hydrolyzate (pH 5) to $A_{620,o}=0.1$. The 96-well microplates are incubated as before supra for 24 hours and at 25° C. Colonized culture wells are pooled, and a dilution is plated to YM agar or 6% glucan AFEX-CSH agar. Selected single colonies are picked after approximately 24 hours to approximately 48 hour incubation at 25° C. and restreaked to YM plates for incubation and glycerol stock preparation by freezing 24 hour cells in 20% glycerol.

For evaluation in 6% glucan AFEX-CSH batch cultures, cells from 48 hour plates streaked from glycerol stocks are suspended in buffer to $A_{620}=10$, and 1 μL is used to inoculate each of four wells of 50 μL 3% glucan hydrolyzate (12% glucan AFEX-CSH at pH 5 diluted 1:3 with sterile water) to $A_{620}=0.2$. Microplates are developed for 24 hours, and then 2 wells are transferred to inoculate precultures of 25 mL of pH 5 6% glucan AFEX-CSH/50 mL flasks with silicon sponge closures (Bellco Glass, Inc., Vineland, N.J.). The precultures are incubated for 24 hours at 25° C., approximately 150 rpm (1" orbit) and then are used to inoculate similar 25 mL growth cultures to $A_{620}=0.1$. The cultures are incubated as described supra for precultures, and sampled daily (0.2 mL) are removed for monitoring biomass accumulation (absorbance at 620 nm) and concentrations of sugars and fermentation products via HPLC.

The performance of 6% glucan AFEX-CSH-grown populations repitched to 8% glucan hydrolyzates is also studied. Inocula for 30 mL growth cultures are prepared as described above for 6% glucan AFEX-CSH batch cultures. Growth cultures are inoculated to $A_{620}=0.1$ and are then incubated in 50 mL flasks with silicon sponge closures (Bellco Glass, Inc., Vineland, N.J.). Cultures are sampled daily for $A_{620}$ and HPLC analyses. When the majority of the xylose is consumed, the cells from growth cultures are harvested by centrifugation and are repitched to $A_{620}=40$ in 4.2 mL of 8% glucan AFEX-CSH in 50 mL flasks with septum caps, vented with ⅜" 26 G needles. All cultures are incubated at initial pH 5, 25° C., 150 rpm, 1" orbit. The daily samples are plated for viable cells, $A_{620}$ is measured, and the remaining sample is centrifuged to collect supernate for HPLC analyses as described supra.

In later studies, repitched 6% glucan AFEX-CSH cultures are fed with 12% glucan hydrolyzate. Following the above procedure, cells are harvested by centrifugation and resuspended to $A_{620}=50$ in 4.2 mL of 6% glucan AFEX-CSH (pH 5) in a 50 mL flask with vented septum cap. All flasks are incubated as described supra. After approximately 24 hours and significant sugar consumption in the 6% glucan hydrolyzate, the cultures are then fed 4 mL of 12% glucan hydrolyzate (pH 5). The cultures are sampled prior to the feed and thereafter.

To evaluate the diauxic lag of the cultures on ODM with mixed sugars and tolerance of acetic acid, precultures of 75 mL ODM with 150 g/L xylose in 125 mL flasks with silicone sponge closures (Bellco Glass, Inc., Vineland, N.J.) are inoculated by loop transfer from YM glycerol streaks. The 24 hour precultures are used to inoculate similar 75 mL test cultures but with ODM containing 75 g/L of glucose and 75 g/L of xylose. All flask cultures have initial pH 6.5 and are shaken at 25° C., 150 rpm (1" orbit). Time courses of biomass accumulation are monitored by optical density, and the sugar and fermentation product concentrations are measured via HPLC using the methods described supra. The impact of 0-15 g/L acetic acid on strain fermentation of glucose and xylose is also tested using a similar cultivation protocol except that the initial pH is set at approximately 6.0±0.2 in order to buffer pH rise resulting from acetic acid consumption.

Figure 2A:
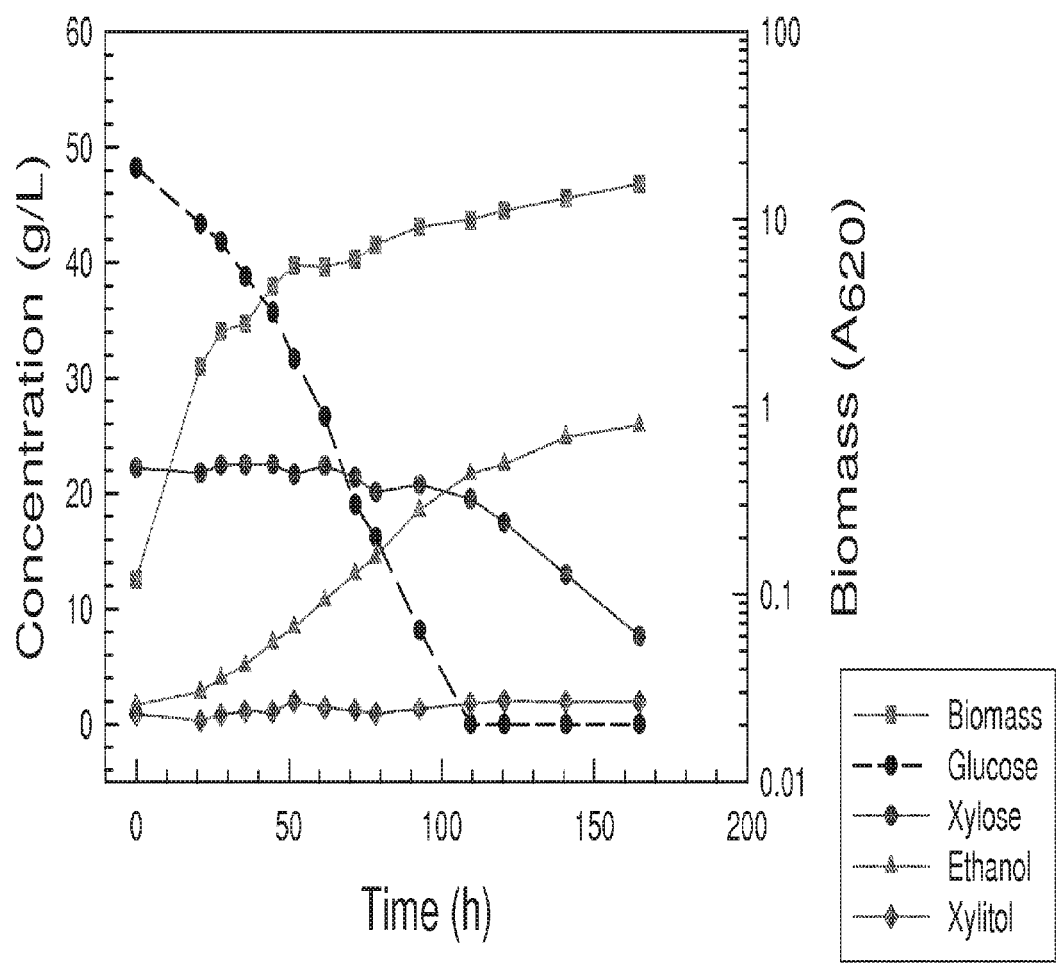
FIGS. 2A and 2B illustrate *S. stipitis* parent strain fermentation of 6% glucan AFEX-pretreated corn stover hydrolyzate (FIG. 2A) and adapted Colony 5 fermentation (FIG. 2B). Symbols in both
Figure 2B:
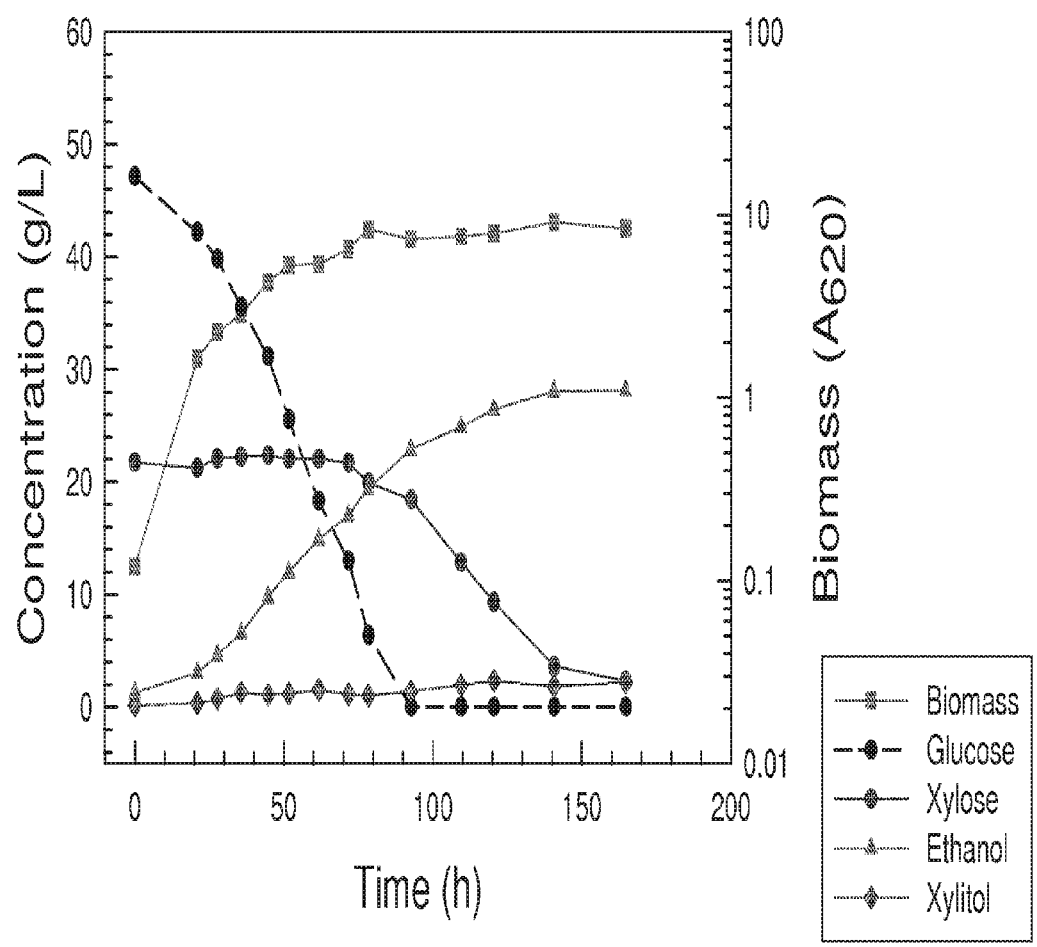
Figure 3A:
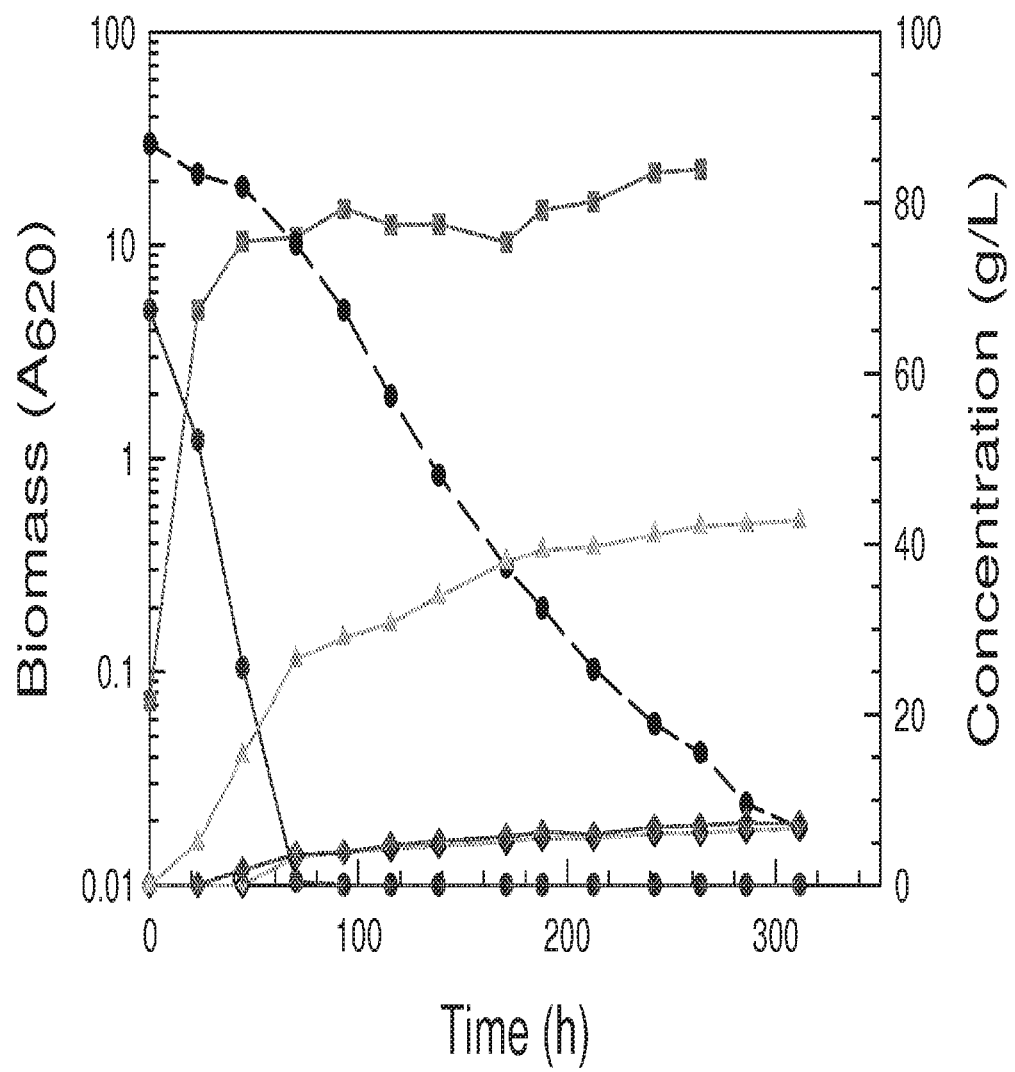
FIGS. 3A, 3B, 3C, and 3D show the fermentation performance on ODM with 66 g/L glucose and 87 g/L xylose for parent strain *S. stipitis* (FIG. 3A), for AFEX-CSH adapted population derived from parent strain *S. stipitis* (FIG. 3B), for single cell Colony 1 isolated from the adapted *S. stipitis* population (FIG. 3C), and for single cell Colony 5 isolated from the adapted *S. stipitis* population (FIG. 3D). Symbols for FIGS. 3A, 3B, 3C, and 3D are biomass (square), glucose (circle with dashed line), xylose (circle with solid line), ethanol (triangle), xylitol (diamond), and adonitol (light diamond with black edge).
Figure 3B:
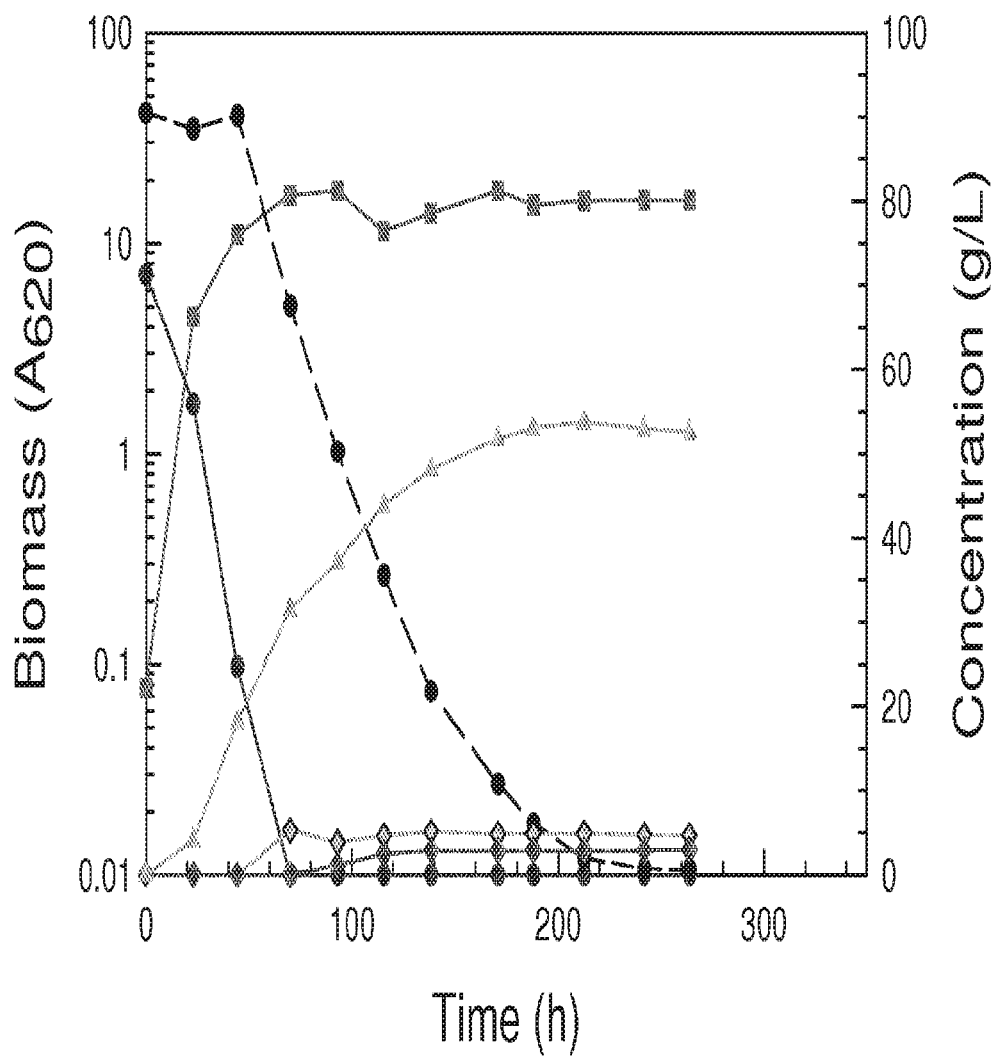
Figure 3C:
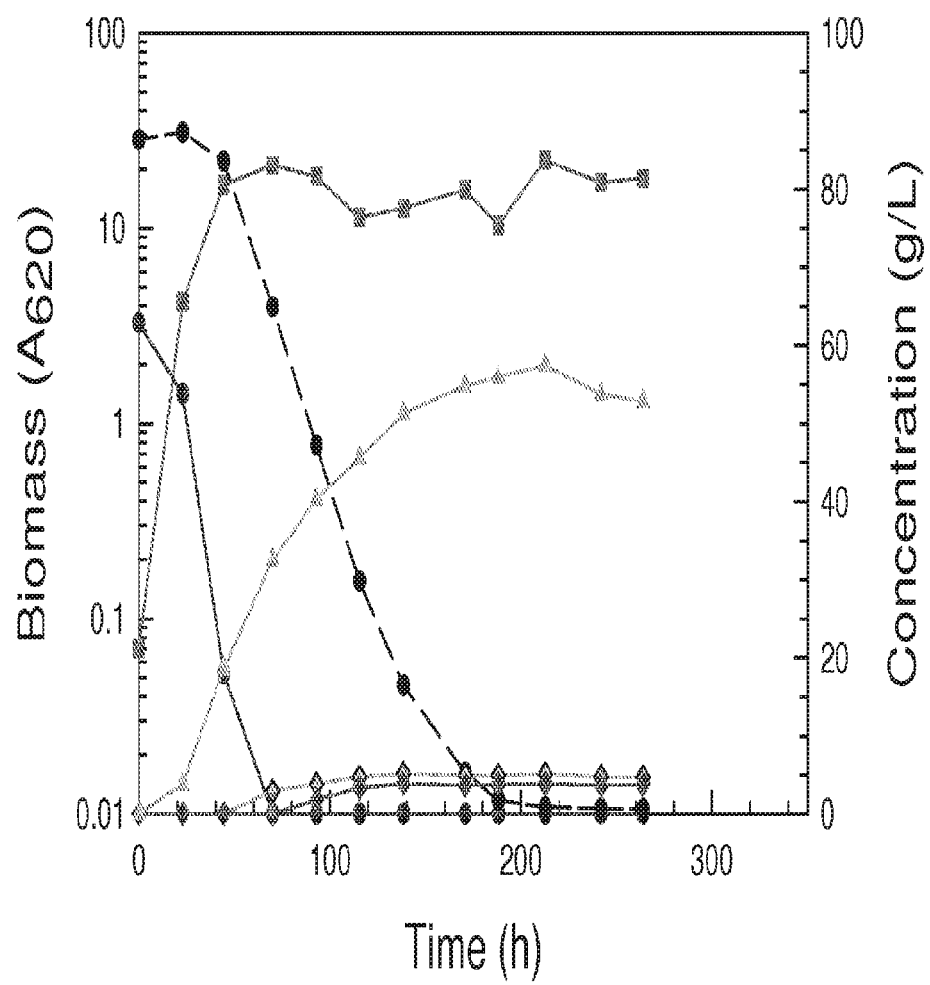
Figure 3D:
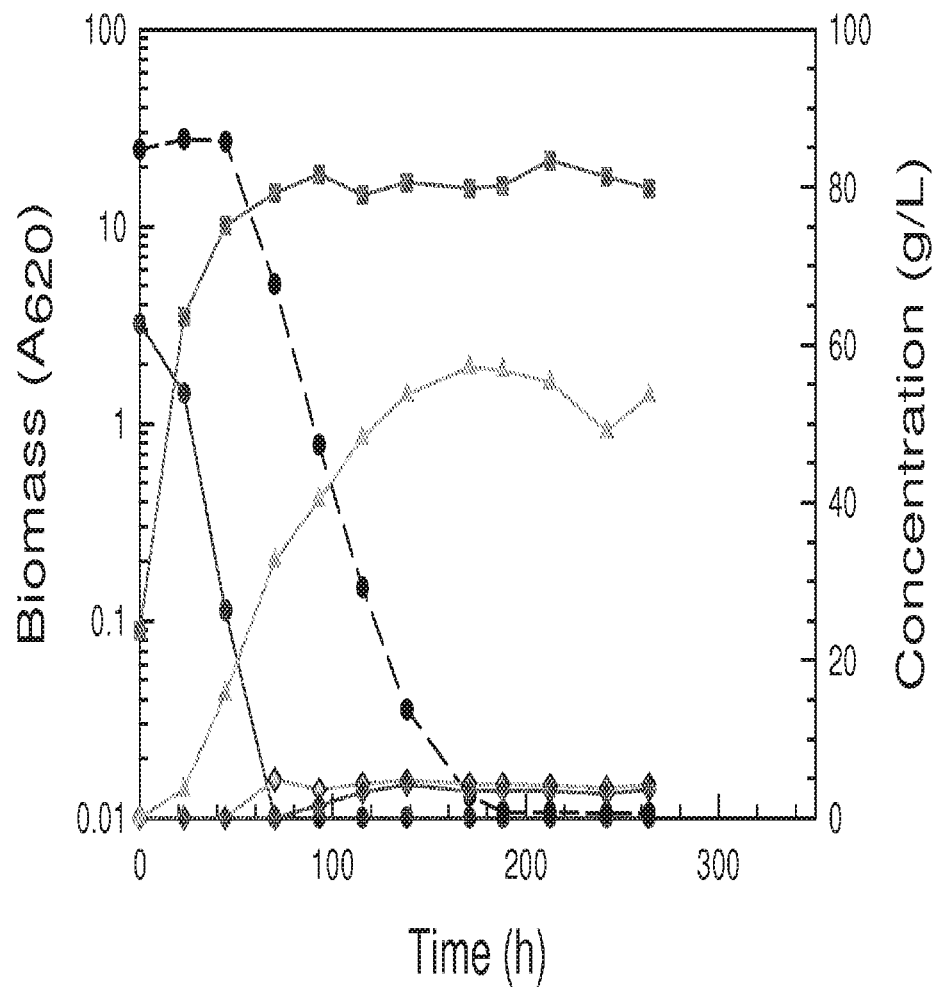
Figure 4A:
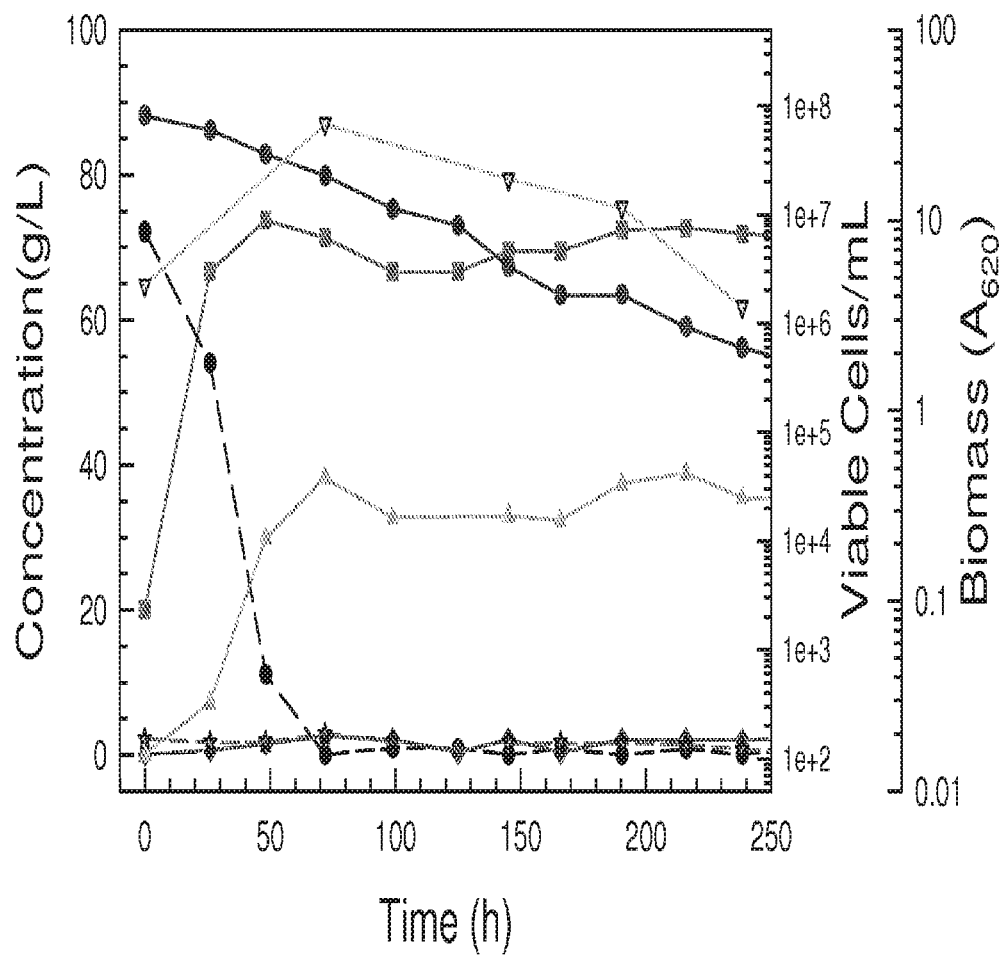
FIGS. 4A, 4B, and 4C show the sensitivity of *Scheffersomyces stipitis* parent strain to increasing acetic acid concentrations at 2 g/L (FIG. 4A), 6 g/L (FIG. 4B), and 10 g/L (FIG. 4C).
Figure 4B:
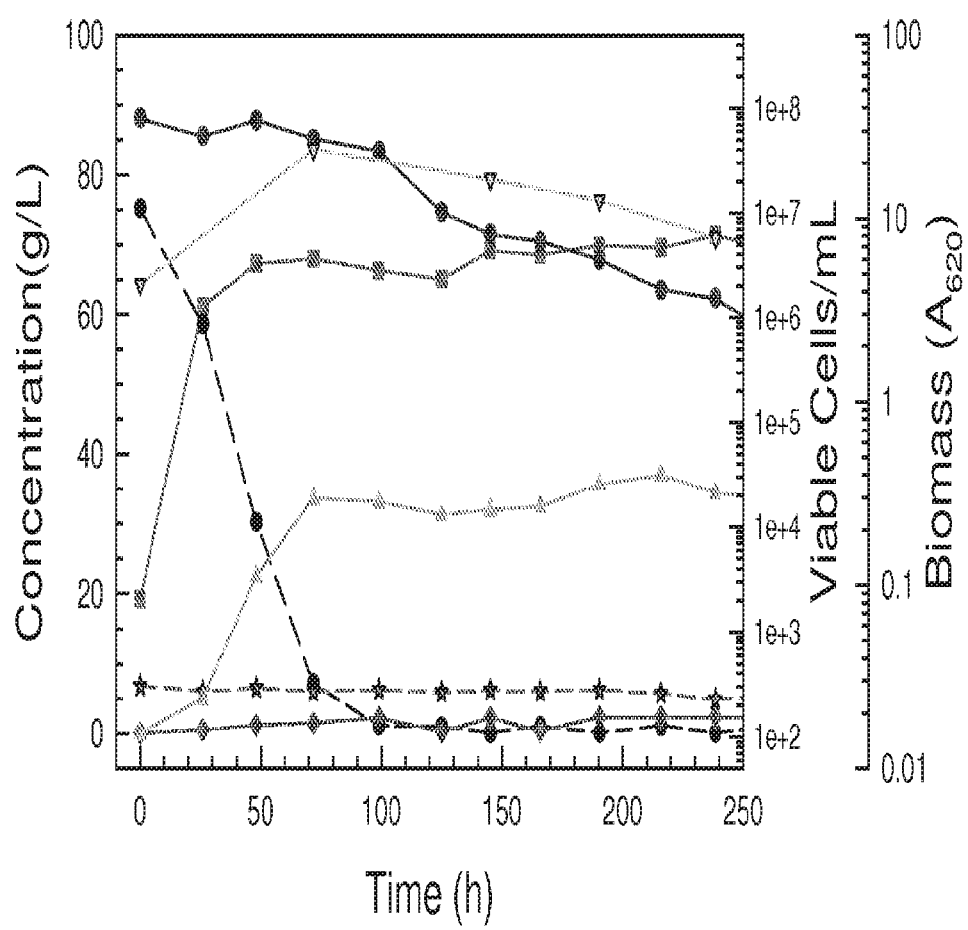
Figure 4C:
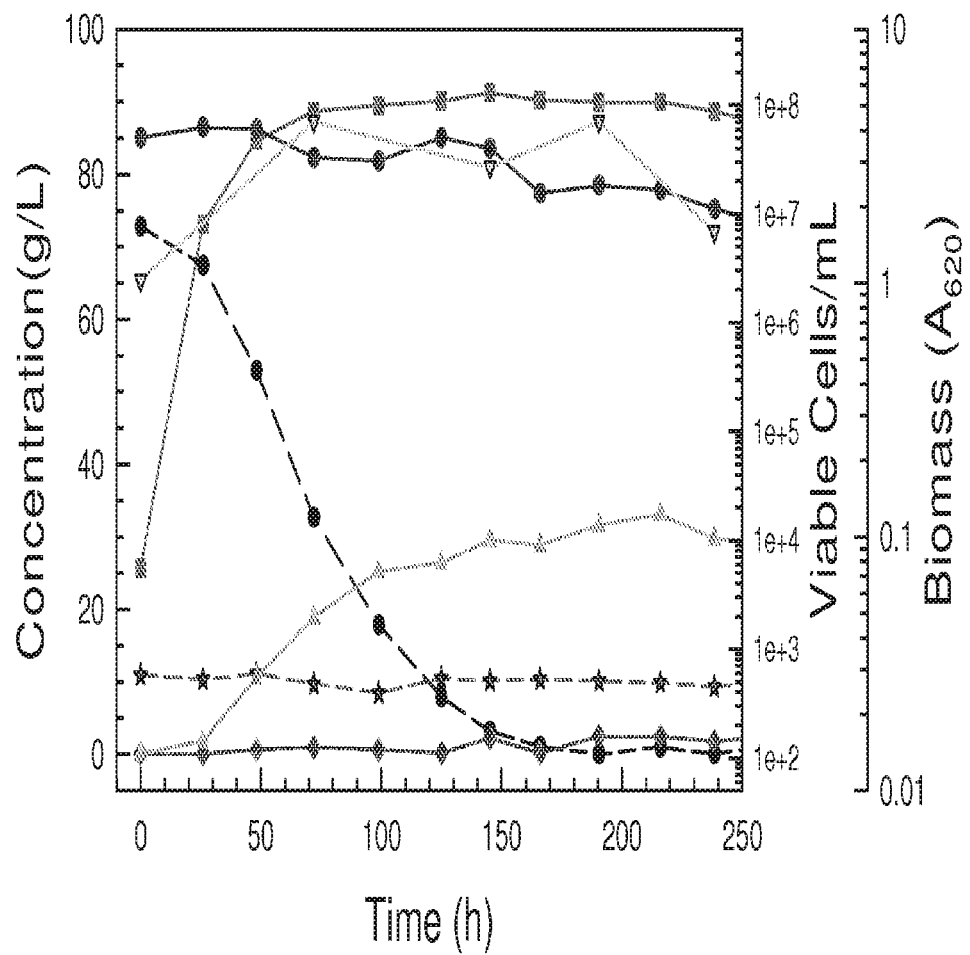
Figure 4D:
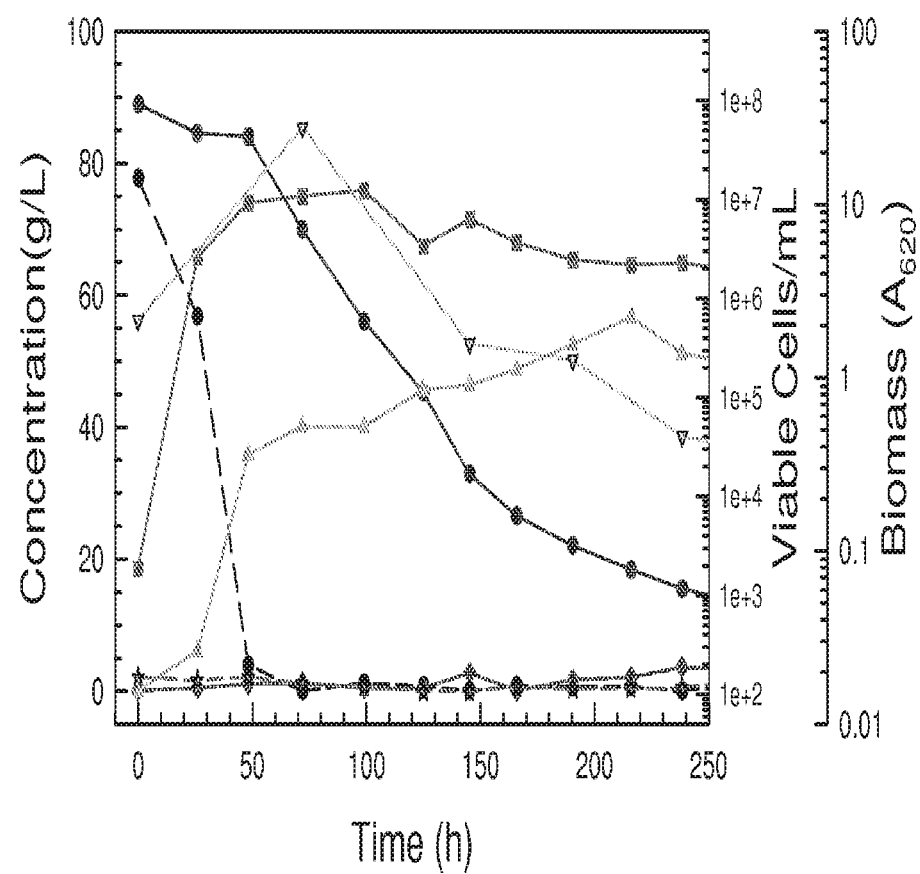
FIGS. 4D, 4E, and 4F show the relative tolerance of adapted Colony 5 to increasing acetic acid concentrations at 2 g/L (FIG. 4D), 6 g/L (FIG. 4E), and 10 g/L (FIG. 4F). In these figures, biomass (squares), glucose (circles and dashed line), xylose (circles and solid line), xylitol (diamonds), acetic acid (stars), ethanol (triangles), and viable cells (inverted triangle) are shown.
Figure 4E:
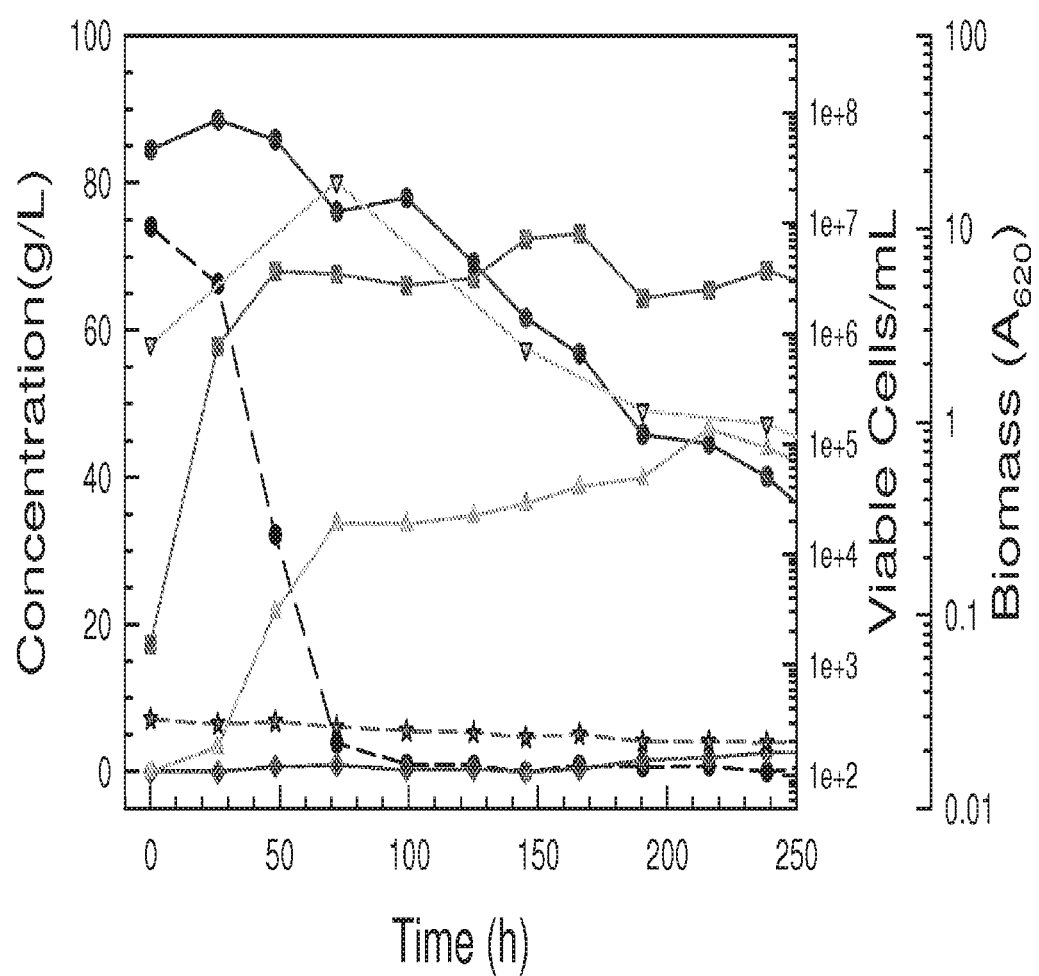
Figure 4F:
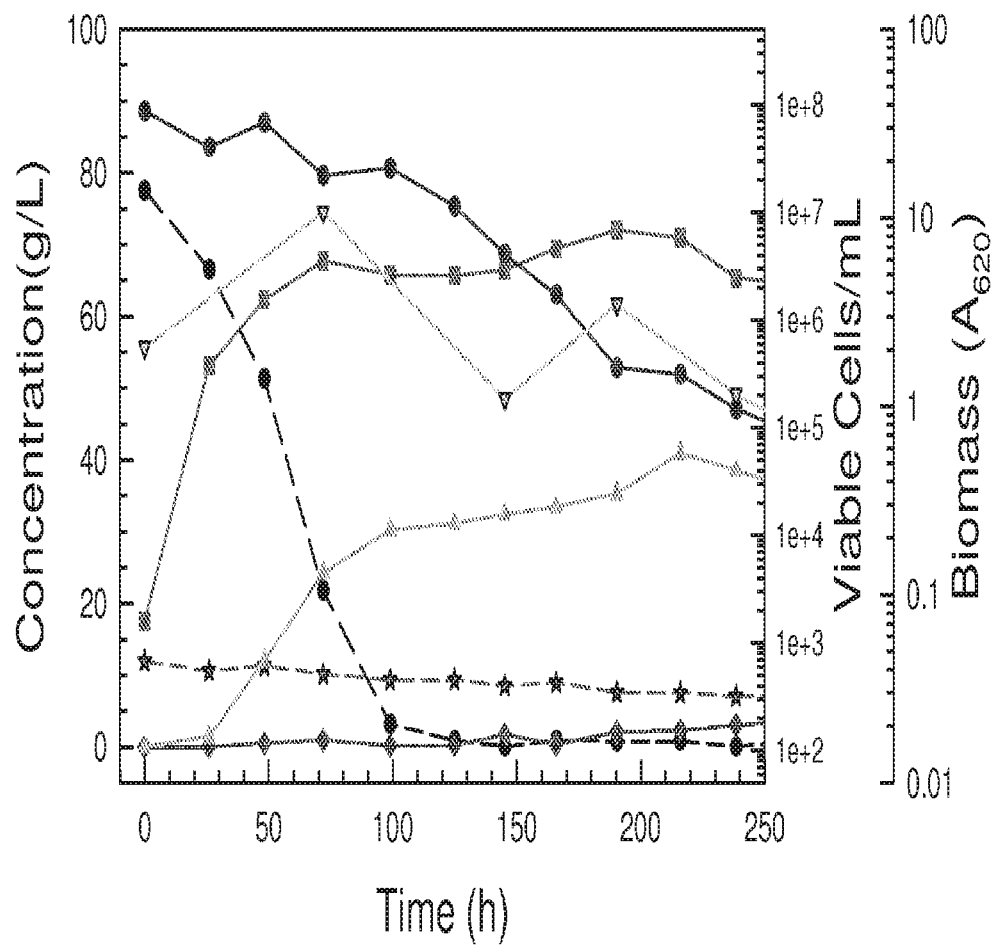

After the parent *S. stipitis* strain (deposit accessory number NRRL Y-7124) is exposed to decreasing dilutions of 12% glucan AFEX-CSH for several weeks, an adapted population is stored as a glycerol stock. When the adapted population is cultivated on 6% glucan AFEX-CSH in comparison with the parent strain, a significantly enhanced performance is observed as shown in FIG. 2. Superior performance features of the adapted population include faster glucose and xylose uptake rates, more complete xylose uptake, and higher ethanol production rate and accumulation.

When single cell isolates of the adapted population are obtained and are compared on ODM with 66 g/L glucose and 87 g/L xylose against the parent *S. stipitis*, all isolates show similar performance to the adapted population and significantly less diauxic lag compared to the parent cultures. FIG. 3 shows the relative performances and indicates that the adapted population and superior isolated single-cell clones (Colonies 1, 5, and 7 (not shown)) are significantly improved in their ability to rapidly switch to xylose fermentation after glucose is depleted. Both of the clones from Colony 1 and Colony 5 consume all xylose by 200 hours and made approximately 57 g/L ethanol, while the parent *S. stipitis* cells have 7 g/L xylose remaining even at 300 hours and accumulate only about 44 g/L ethanol. It was shown previously that the induction of enzymes specific for xylose metabolism are repressed in parent *S. stipitis* strain (deposit accession number NRRL Y-7124) when ethanol concentration exceeds 15 g/L (see Slininger, et al. (2011)). For the fermentations shown in FIGS. 3A, 3B, 3C, and 3D, ethanol reaches nearly 30 g/L by the time glucose is depleted, and the adapted population and clones are not repressed in xylose utilization although the parent strain is severely crippled in its ability to use xylose after the glucose is consumed. Exposure to decreasing dilutions of AFEX-pretreated corn stover hydrolyzate leads to an adapted population better able to ferment this hydrolyzate not only because of enrichment of the population in members more resistant to the inhibitory environment of the hydrolyzate but also because of enrichment of the population in members that are less susceptible to ethanol-associated repression of enzymes specific to xylose metabolism, thus avoiding extended diauxic lag.

Despite exposure to relatively low levels of acetic acid (between 2 to 4.7 g/L in dilutions of 12% glucan AFEX-CSH), Colony 5 is able to ferment both glucose and xylose in ODM+2 g/L acetic acid, ODM+6 g/L acetic acid, and ODM+10 g/L acetic acid more efficiently compared to the parent S. stipitis strain (see FIGS. 4A-4F). Even at 10 g/L acetic acid, Colony 5 continues to ferment xylose to ethanol while the parent strain is not able to do so (see FIGS. 4C and 4F). Casey, et al. (*FEMS Yeast Research* 10, 385-393 (2010)) Also Documented Impaired Abilities of engineered *S. cerevisiae* to shift from glucose to xylose utilization in the presence of 7.5 to 15 g/L acetic acid. Despite the strong impact of acetic acid on fermentation, growth of the parent strain and Colony 5 are relatively unimpaired across the concentrations used, although cell death rate appears to be significant.

Figure 5A:
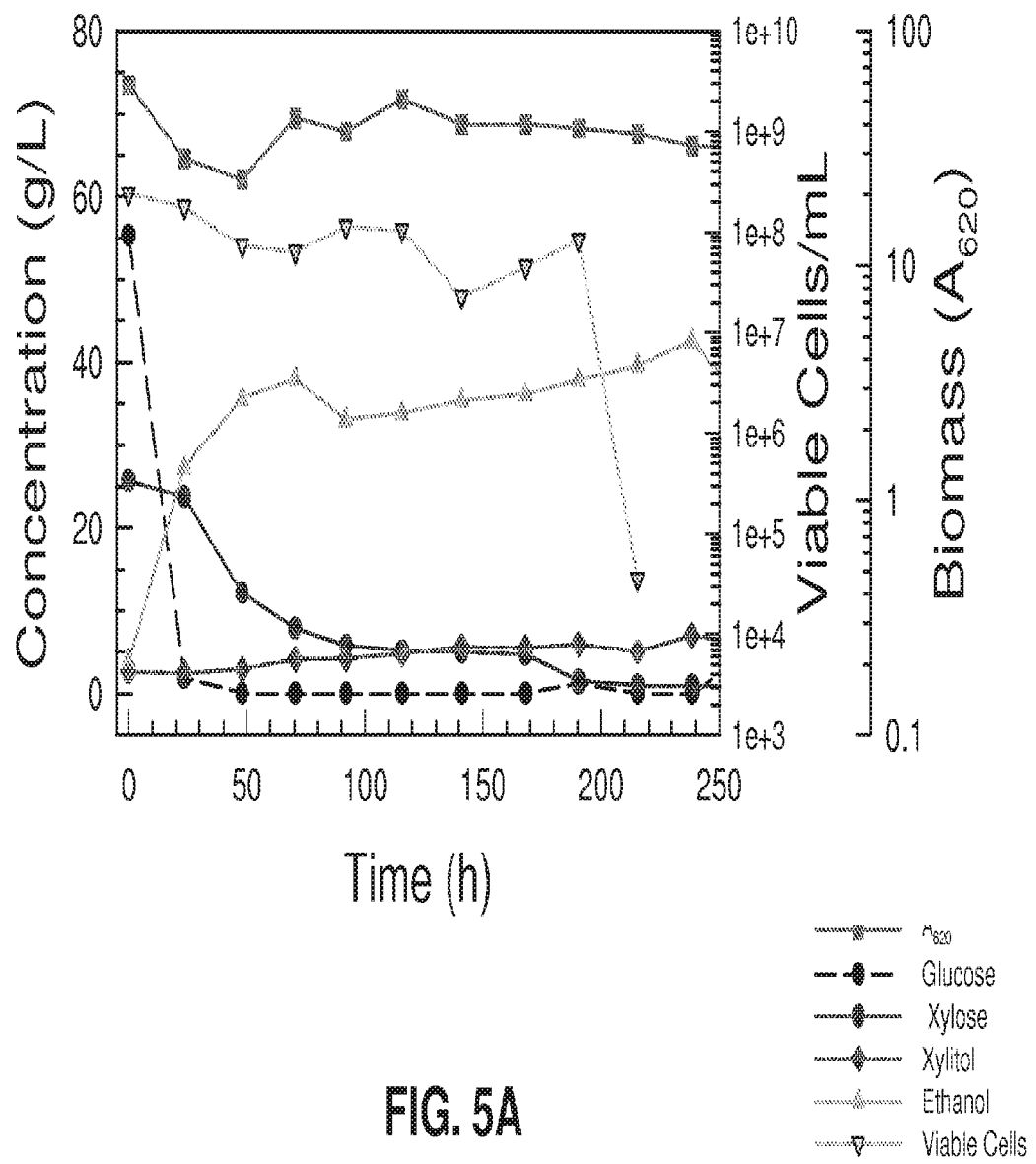
FIGS. 5A and 5B show fermentation data of batches A and B of 8% glucan AFEX-pretreated corn stover hydrolyzate by a large population of *S. stipitis* AFEX-CSH tolerant Colony 5 repitched from 6% glucan batch growth during xylose utilization. Data include biomass (squares), glucose (circles and dashed line), xylose (circles and solid line), xylitol (diamonds), ethanol (triangles), and viable cells (inverted triangles).
Figure 5B:
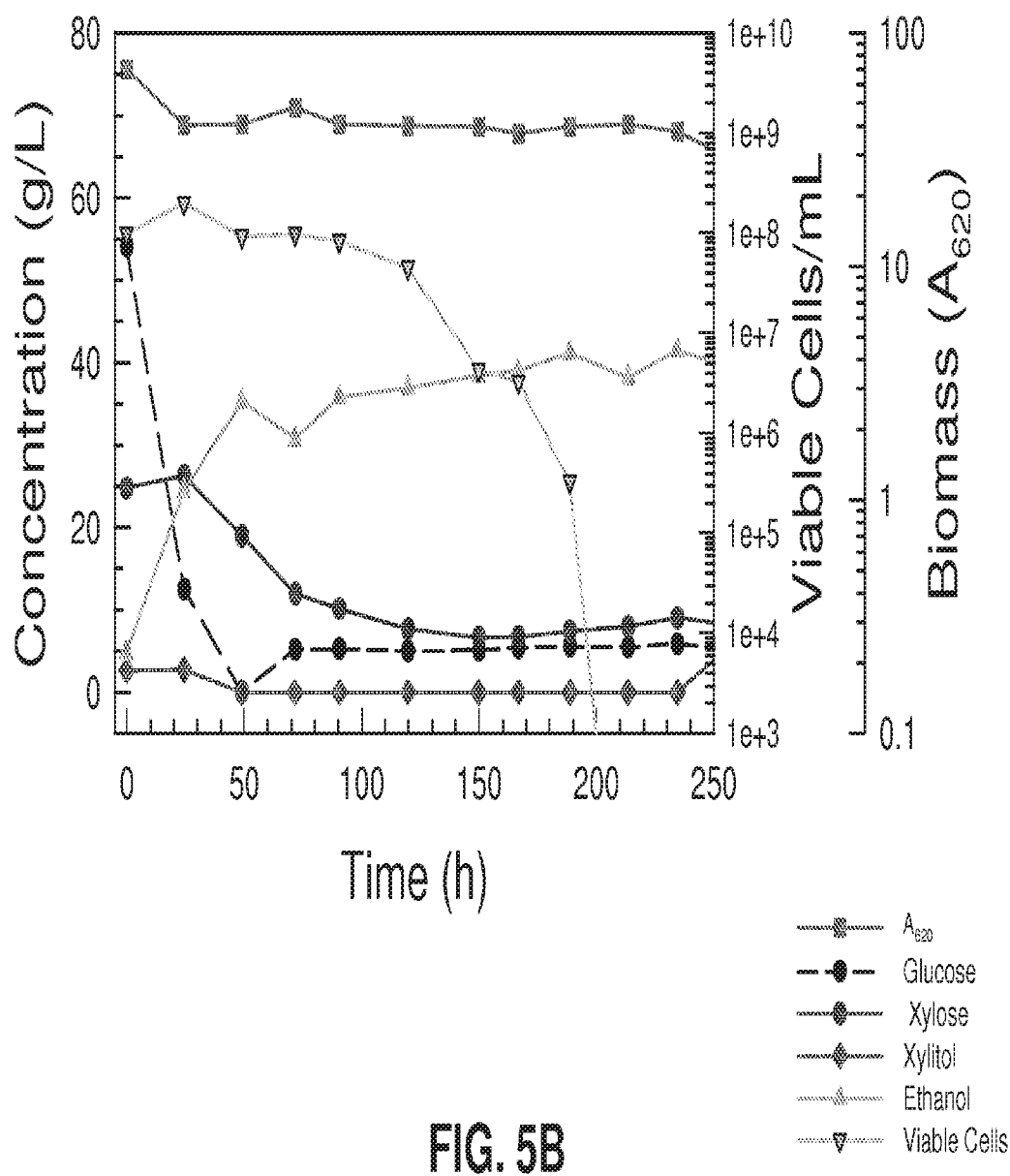
Figure 6A:
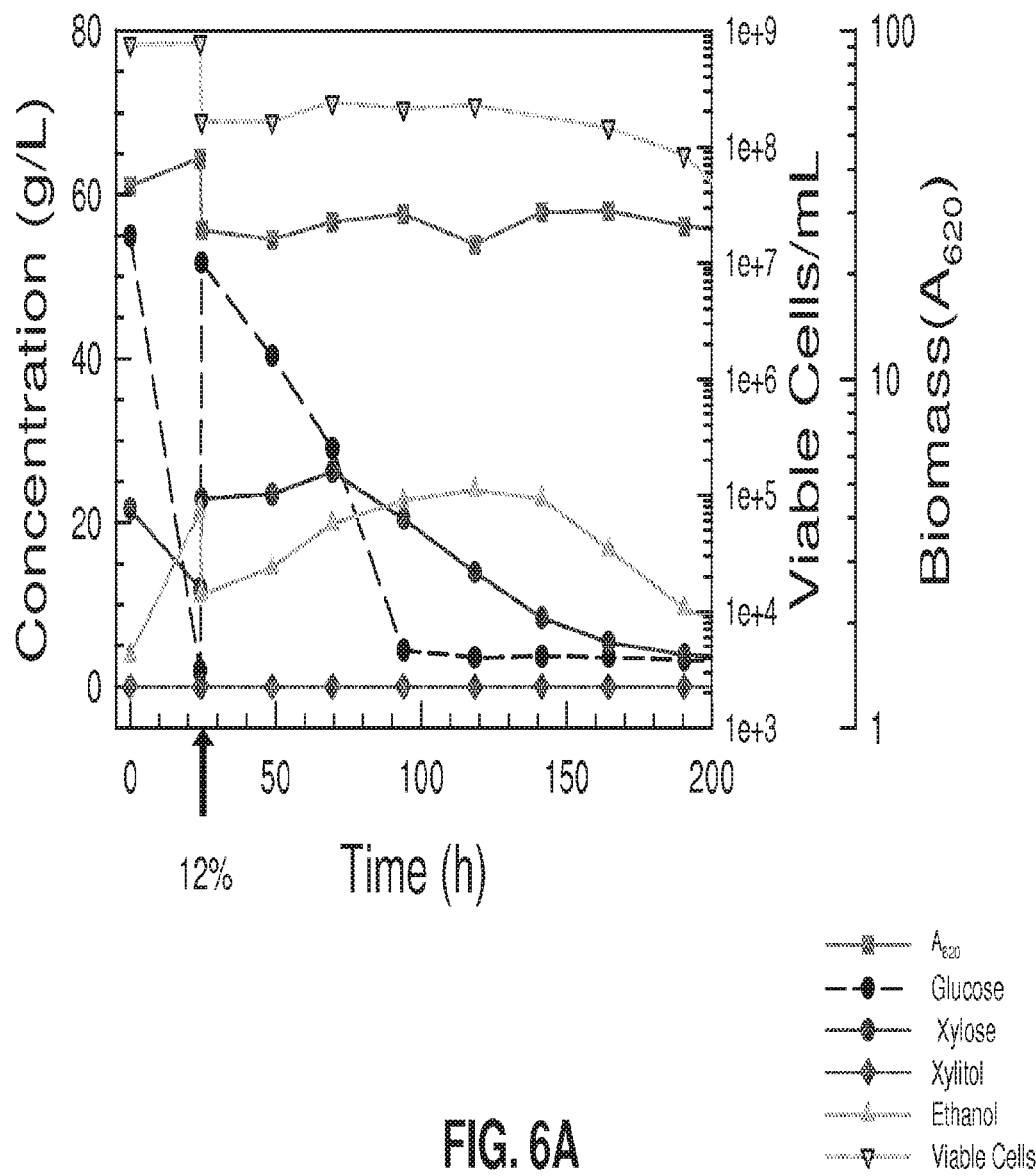
FIGS. 6A and 6B compares the performances of high density cultures of *Scheffersomyces stipitis* parent cells (FIG. 6A) and hydrolyzate tolerant Colony 5 cells (FIG. 6B) both repitched from 6% glucan during xylose uptake into fresh 6% glucan hydrolyzate then fed at 24 hours with an equal volume of 12% glucan hydrolyzate. Data include biomass (squares), glucose (circles and dashed line), xylose (circles and solid line), xylitol (diamonds), ethanol (triangles), and viable cells (inverted triangles).
Figure 6B:
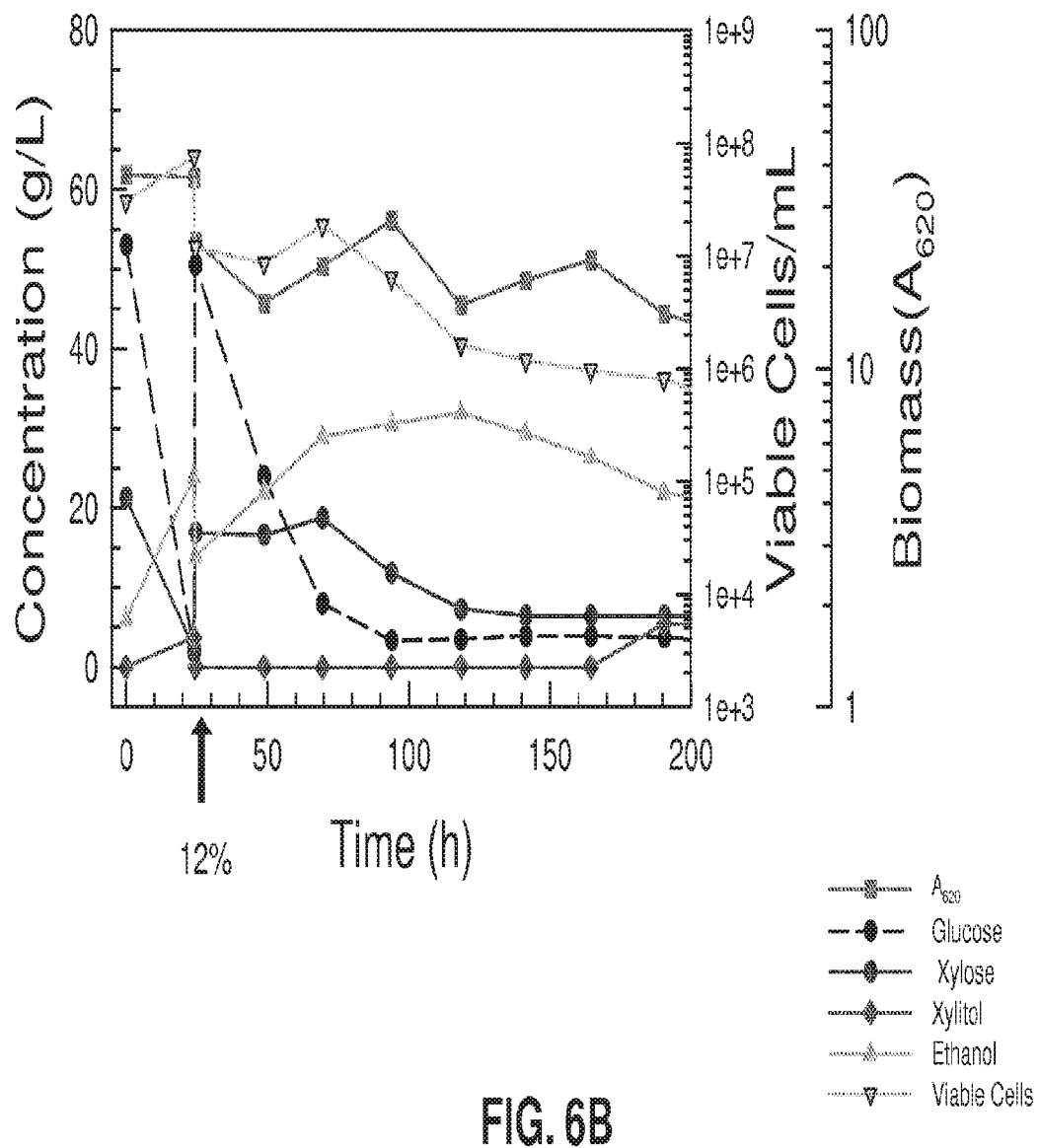

Two Colony 5 populations grown on 6% glucan AFEX-CSH and repitched to $A_{620}$=40 in higher glucan hydrolyzates are also tested and found to allow the accumulation of over 40 g/L ethanol on approximately 8% glucan hydrolyzates (FIGS. 5A and 5B). Although full accumulation of the ethanol requires over 188 hours, approximately 85% of the ethanol accumulates in the first 48 hours. Further testing of adapted Colony 5 strain in comparison to its parent in populations repitched to $A_{620}$=40 in 6% glucan hydrolyzate and later fed with an equal volume of 12% glucan hydrolyzate indicates a significant improvement in Colony 5 cells over the parent cells with respect to xylose uptake rate, ethanol productivity and maximum ethanol accumulation (see FIGS. 6A and 6B) during both the initial batch and fed-batch phases of the cultivation. The adapted Colony 5 isolate is able to consume both glucose and xylose more quickly than the parent S. stipitis strain, reducing the sugar consumption time by 25% from 200 hours to just under 150 hours. In addition, ethanol accumulation of the adapted Colony 5 strain is improved by about 30% over that of the parent S. stipitis cells. However xylose utilization is not complete, and Colony 5's cell viability falls near the end of glucose consumption and the beginning of xylose uptake, suggesting a potential problem of combating deleterious impacts of ethanol while trying to metabolize the xylose.

Example 2 Continuous Culture Selection for Ethanol-Challenged Xylose Utilization To improve ethanol tolerance and resistance to repression of enzymes specific to xylose utilization, Colony 5 is inoculated to a continuous culture operated at a low dilution rate with high ethanol concentrations and xylose in the feed, as described below. The goal of this treatment of Colony 5 is to select and enrich for yeast cells with improved growth and fermentation on xylose as sole carbon source in the presence of high ethanol concentrations. Cells are exposed to equal to or more than 15 g/L ethanol, which is associated with repression of xylose-specific enzymes in the parent S. stipitis strain (Slininger, et al. (2011)). The continuous culture feed medium is ODM with 60-100 g/L xylose and 20-50 g/L ethanol at pH 6.3±0.2. AFEX-tolerant Colony 5 is precultured in 75 mL ethanol-free feed medium in 125 mL flasks at 25° C., 150 rpm (1" orbit) for 24 hours. The continuous culture is initiated with Colony 5 preculture by inoculating 100 mL of ODM+100 g/L xylose+20 g/L ethanol to $A_{620,o}$=approximately 0.5. The 100 mL culture holding volume is maintained at 25° C. in a jacketed 100 mL spinner flask (Bellco Glass, Inc., Vineland, N.J.) stirred at 200 rpm and outfitted with a sterilizable pH electrode. Temperature is controlled with a refrigerated circulating water bath. For the first 125 days of cultivation, the feed medium is dosed using a pH actuated pump such that when the culture fermentation is sufficient to drop the pH to 5.4, the feed medium at 100 g/L xylose and 50 g/L ethanol doses to prevent the pH from dropping lower. A continuously pumping effluent pump drawing from the culture surface maintains a constant fermentation volume. Thus the ethanol concentration of the culture rises at an artificially high rate in response to fermentation progress. Samples (1-2 mLs) are removed from the continuous cultures every 48 hours to 72 hours and are analyzed for cell density ($A_{620}$), cell viability, sugars and ethanol as described supra. Effluent is collected and measured at sample times. Glycerol stocks are saved on a regular basis by isolating from viability spread plates allowing formation of approximately 30 to approximately 100 colonies, which would be a sampling of the most prevalent, robust colonists at that point in the enrichment process. This plate is flooded with approximately 5 mL of 20% glycerol to prepare duplicate cryovials. On occasion, it is necessary to restart the continuous culture using the most recent glycerol stock.

Once pH-actuated continuous feed cultures are able to grow solely on xylose in the presence of up to 28 g/L ethanol, the remainder of the continuous culture selection process (next 300 days) is carried out at a dilution rate of ~0.012 per hour using Gilson Minipuls 2 feed and effluent pumps (Gilson, Inc., Middleton, Wis.) and a feed medium of ODM with 60 g/L xylose and 30-50 g/L ethanol. The selection culture is restarted from the current most resistant glycerol stock population streaked to YM and is transferred to a pre-culture of ethanol-free ODM with 60 g/L xylose for incubation as described above. The 100 mL holding volume of ODM with 60 g/L xylose and 20 g/L ethanol is inoculated to $A_{620}$=0.5, and the population is allowed to grow batchwise to stationary phase; then the feed medium flow is started. Over time, ethanol concentration in the feed is raised as yeast tolerance improves. If viable cell densities fall below $10^4$ cells/mL, the culture is returned to batch mode to allow recovery before resuming continuous flow. To capture advances, glycerol stocks are prepared as described above. The continuous culture is restarted on occasion using the most recent glycerol stock(s) demonstrating significant improvement based on performance testing as described below.

During the last six months of operation, ultra-violet (UV) irradiation is used approximately monthly to induce further mutations in the glycerol stock populations used to restart cultures. Colonies from glycerol streaked plates are resuspended in 10 mL of ODM with 60 g/L xylose (as used for precultures) and are transferred to a common sterile flask. The combined cell suspension at approximately $5 \times 10^8$ viable cells/mL is used to cover the bottom of four or five petri plates. Each open plate is situated below the UV light source in a biological safety cabinet, and is exposed for 45 minutes. The excess cell suspension remaining after filling plates and a post-irradiation sample are dilution plated to allow estimating the kill rate at approximately 97%. The UV-exposed cultures (approximately 30 mLs) are transferred to a foil covered 50-mL flask to preserve mutations as cultures are incubated at 25° C. and 150 rpm for 24 hours while viable cell counts returned to between approximately $1 \times 10^8$ viable cells/mL for continuous culture inoculation and approximately $1 \times 10^7$ viable cells/mL.

Performance of adapted population growth and fermentation of xylose in the presence of ethanol is performed. In order to focus isolation efforts, selected glycerol stock cultures are screened to identify those with best growth and fermentation of xylose in the presence of ethanol. First, xylose uptake by glucose-grown high cell densities is evaluated in the presence of ethanol. Three 75-mL pre-cultures per glycerol streak are inoculated by loop. The pre-culture medium in this case is ODM with 150 g/L glucose instead of xylose. Precultures are incubated as described above, but for 96 hours prior to use as inocula for the test flask cultures in order to produce large populations requiring enzyme induction for xylose utilization. Test cultures are inoculated to $A_{620}=40$ by resuspending pelleted cells from precultures in 30 mL ODM+60 g/L xylose+30-45 g/L ethanol, and are incubated at 25° C., 150 rpm (1" orbit) in 50-mL flasks with silicon sponge closures.

Growth on xylose in the presence of ethanol is also evaluated. Precultures are inoculated by loop transfer to 75 mL of ODM with 150 g/L xylose in 125 mL flasks, and incubated as previously described. Test cultures are inoculated to an $A_{620}=0.1$ in 25 mL of ODM+60 g/L xylose+30-45 g/L ethanol in 125 mL flasks. Flasks are incubated at 25° C., 300 rpm, 1" orbit and are sampled.

Isolation of single-cell colonies utilizing xylose in the presence of ethanol is performed next. For each glycerol stock showing superior ability to grow on and ferment xylose in the presence of ethanol, 1 mL precultures on PSGHL mixed 1:1 with ODM+50 g/L xylose (no ethanol) are inoculated by picking from glycerol stock streaks. Precultures are contained in 96-well, deep well plates with low evaporation covers (Duetz clamping system, Applikon Biotechnology, Inc., Foster City, Calif.) and are incubated 48 hours at 25° C., 400 rpm, 1" orbit. Precultures are used to inoculate 16×1 mL replicate cultures to $A_{620}=0.5$ in 1:1 PSGHL:ODM+50 g/L xylose with 20, 30, or 40 g/L ethanol for enrichment of tolerant colonists. Enrichment cultures are incubated similarly to precultures. Harvesting from highest ethanol concentration allowing growth and xylose use, each cell line is plated to YM agar to obtain single colonies. Ten colonies per cell line are picked and are streaked to new YM agar plates for glycerol stock preparation.

Figure 7A:
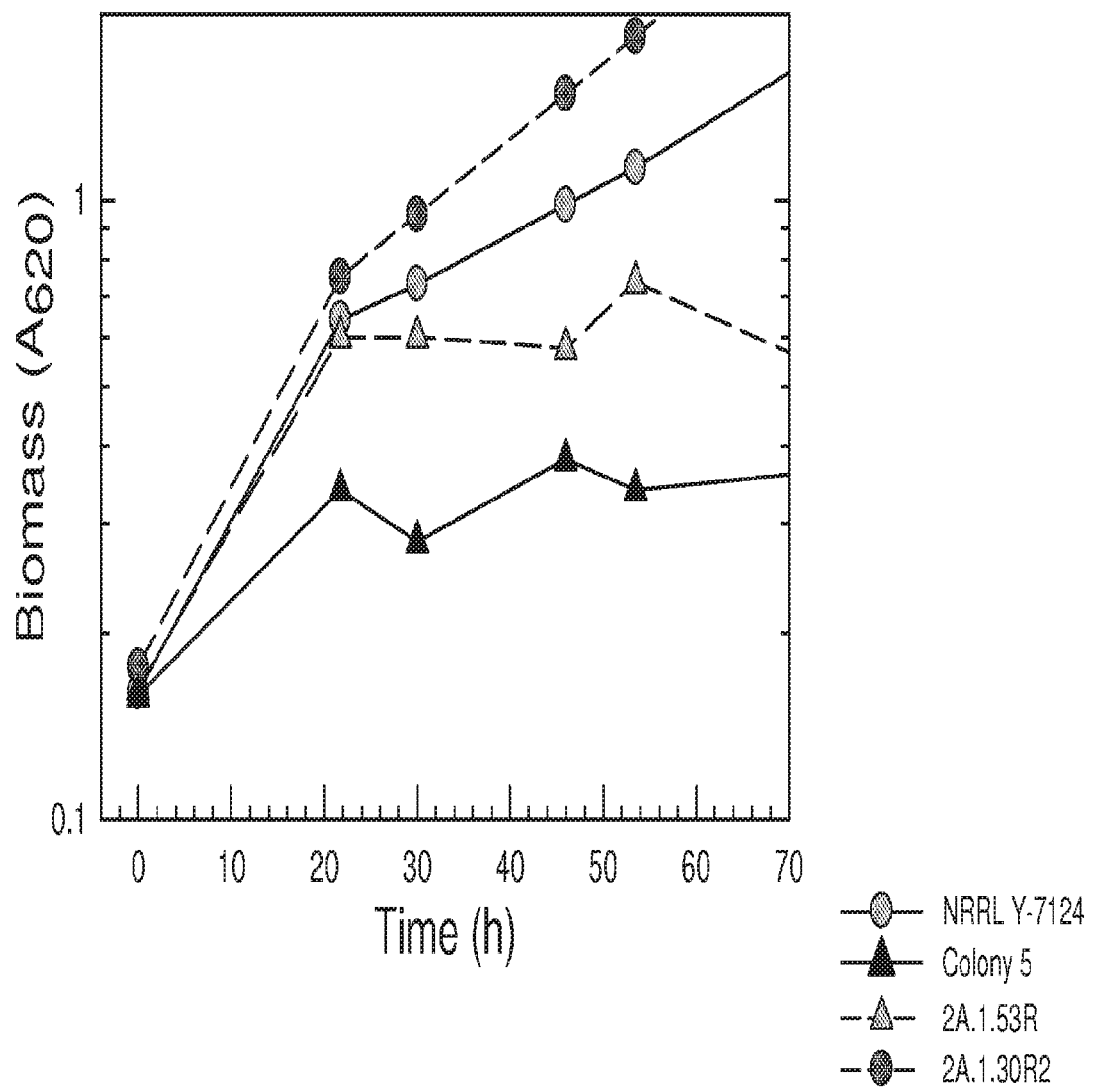
FIG. 7A shows the growth rate on ODM+60 g/L xylose+40 g/L ethanol of two ethanol resistant derivatives of Colony 5 [a derivative glycerol stock population obtained early in the selection process (2A.1.53R, triangle and dashed line) and after UV irradiation of continuous culture inocula (2A.1.30R.2, circle and dashed line)], *S. stipitis* parent cells (circle with solid line) and AFEX-CSH tolerant Colony 5 cells (triangle with solid line).
Figure 7B:
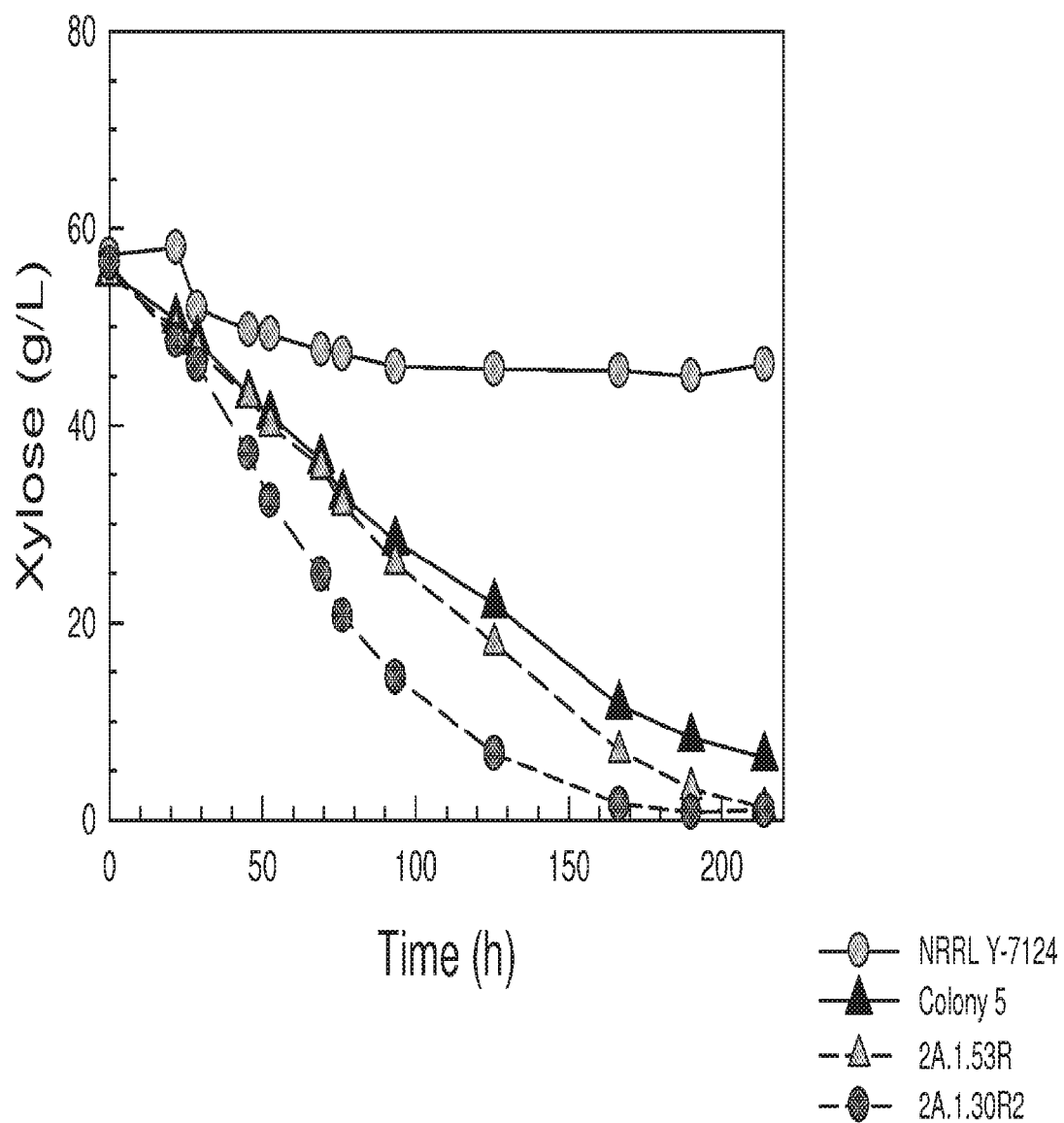
FIG. 7B shows xylose uptake by dense populations of glucose-grown yeast ($A_{620}$=50) in ODM with 40 g/L ethanol strains 2A.1.53R (triangle and dashed line), 2A.1.30R.2 (circle and dashed line), *S. stipitis* parent cells (circle with solid line) and Colony 5 cells (triangle with solid line).

Derivatives of Colony 5 with improved ethanol tolerance and reduced repression of enzymes specific to xylose utilization result from the continuous culture selection described supra. In FIGS. 7A-7B the progressive improvement in initial growth rate on xylose in the presence of 40 g/L ethanol is demonstrated for two enriched populations, 2A.1.53R and 2A.1.30R2, which are collected at earlier and later times, respectively, during operation and then frozen in glycerol. Population 2A.1.30R2 is obtained from continuous culture following reinoculation with UV-mutagenized populations and further enrichment under 40-50 g/L ethanol challenge. These data suggest that the ethanol resistance loss shown by Colony 5 is alleviated by the continuous culture process and UV exposure. In addition, the ability of glucose-induced cells to switch to xylose metabolism in the presence of 40 to 45 g/L ethanol is improved over that of the Colony 5 inoculum and is far better than that of the parental S. stipitis cells. The enriched populations 2A.1.30R2 and 2A.1.53R are successful at using xylose even in the presence of >40 g/L ethanol when yeast have been cultivated on glucose and are then transferred in high density to ODM with xylose and ethanol. Three single cell isolates (2A.1.53R-E20-C1, 2A.1.53R-E30-C3, and 2A.30R2.E40-05) are recovered from the populations which demonstrate superior ability to ferment hydrolyzates in subsequent screens.

Example 3 PSGHL Serial Transfer Culture Adaptation

To further broaden hydrolyzate tolerance, Colony 5 and the ethanol tolerant derivative population 2A.1.53R are further challenged by repetitive serial transfer to decreasing dilutions of xylose-rich PSGHL in microplates. Additionally, parent strain S. stipitis is subjected to direct adaptation in PSGHL as a control relative to sequential application of different adaptation challenges. Using dilution plating, over 150 isolates are recovered either directly from adaptation microplates or from frozen glycerol stock populations after streaking to YM agar and selective enrichment with hydrolyzate and/or ethanol challenges. Four superior hydrolyzate-fermenting isolates are identified from parent strain S. stipitis adaptation to PSGHL (Y7124 GP-5, Y7124 S90E40-1, Y7124-6 and Y7124-10) and one isolate each is derived from Colony 5 and population 2A.1.53R (Colony 5 GP-6 and 2A.1.53R-1, respectively) when the following protocols, screening, and ranking processes are applied.

Pre-cultures of S. stipitis parental cells, USDA deposit accession number NRRL Y-7124, Colony 5, and 2A.1.53R in 75 mL ODM+150 g/L xylose are prepared and are incubated as described above for the AFEX-CSH hydrolyzate adaptation process. PSGHL is diluted with water to provide a series of increasing concentrations in 96-well microplates for each of the three cell lines. Each 50 μL micro-culture of the dilution series is initiated to $A_{620}$=approximately 0.1 to approximately 0.5 with precultures. The PSGHL adaptation is carried out using the same procedure as the AFEX-CSH hydrolyzate adaptation detailed above, and glycerol stocks of progressive populations are prepared. Single-cell isolates are obtained directly from final (480 day) adaptation plates by dilution plating each of the three cell lines to YM agar because all cells are growing in the full strength PSGHL. Ten large colonies are picked for each of the three cell lines and then bar streaked to YM plates for glycerol stocks.

Glycerol stocks of the three cell lines at two earlier points of adaptation (360 day and 420 day) are streaked to YM agar, pre-cultured 24 hours on ODM+50 g/L xylose, then are challenged in 50 μL of 50% PSGHL per micro-plate well incubated statically for 48 hours from initial $A_{620}=$ approximately 0.2, then are spread onto PSGHL gradient plates ranging from 0 to 50% strength hydrolyzate (delivering approximately 300 to approximately 400 viable cells per plate). Ten single colonies are picked per cell line from the highest hydrolyzate concentration area of the gradient (Syzbalski and Bryson, *J. of Biotechnology* 64, 489-499 (1952)). Picked colonies are streaked to YM for glycerol stock preparation.

Alternatively, cell lines are propagated from glycerol stocks for selective plating on gradient agar, but instead of the gradient agar plates, 96-well micro-plates with a range of hydrolyzate concentrations from approximately 50% to approximately 100% strength and ethanol from approximately 10 to approximately 40 g/L are inoculated to $A_{620}$=approximately 0.2. Micro-plates are developed 72 hours to 96 hour with the following conditions: 50 µL/well, static incubation, 25° C., humidified box. Cells are isolated from wells of the harshest hydrolyzate-ethanol combinations showing growth. Culture samples are serially diluted and are spread plated on YM agar. Ten colonies, among the most prevalent per well, are picked per each of the three cell lines and purity streaked for freezing in glycerol as described above.

Example 4 Performance Ranking Screens to Select Best Single-Celled Colonies from AFEX-CSH, Ethanol, and Dilute Acid PSGHL Adaptation Phases Deep well plate screen of PSGHL performance is used as a primary elimination of inferior isolates. Five sets of thirty isolates are screened along with parent *S. stipitis* (USDA deposit accession number NRRL Y-7124) as the control to choose six top strains from each set of thirty isolates. For higher throughput, the screen is carried out in deep well plates filled 1 mL per well and covered with stainless steel lids with black silicone low evaporative seals (Duetz System, Applikon Biotechnology, Inc., Foster City, Calif.). Plates are incubated in an INNOVA® 42R shaker (Eppendorf AG, Hamburg, Germany) at 25° C. and 400 rpm (1" shaker orbit). Isolates are picked from glycerol streaks, are placed in duplicate wells of ODM+50 g/L xylose, and are incubated for 48 hours. All deep well plate filling patterns are designed to allow separation of different isolates by open wells. The 50% PSGHL is prepared by mixing PSGHL 1:1 with ODM+10 g/L glucose+50 g/L xylose. 50 µL ODM pre-cultures ($A_{620}$=approximately 10) are transferred to each of two 50% PSGHL wells for each of the isolates and controls to obtain an $A_{620}$=approximately 0.5. Cells of each isolate are harvested at 72 hours from the 50% PSGHL challenge pre-cultures and are used to inoculate 50 µL per 1000 µL to $A_{620}$=approximately 0.5 in five deep wells for each of two test media: 60% PSGHL+ODM nutrients and 75% PSGHL+ODM+YM nutrients. In the two test media using the indicated partial strength of PSGHL, the nutrients (excluding sugars) are at half of the strength as standard ODM (when designed for use with 50 g/L sugar). When present, YM nutrients are also used at half of the standard strength of 3 g/L yeast extract, 3 g/L malt extract, 5 g/L peptone. For each sampling, a well per each isolate is transferred to centrifuge tubes, which are centrifuged at 7000 rpm, 15 minutes, and the supernate is removed for HPLC assay of ethanol via a Bio-Rad Fast Acid column (Hercules, Calif.) and rapid YSI 2900 automated enzyme analysis of glucose and xylose in 96-well plates (YSI, Inc., Yellow Springs, Ohio). Biomass is measured in 96-well plates with a POWERWAVE™ spectrophotometer (Biotek Instruments, Inc., Winooski, Vt.). Within each of the five sets of isolates tested, relative performance indexes are calculated and are used to rank each strain based on ethanol yield and xylose uptake rate on both test media Next, a comparison of the top PSGHL performers on SGH at different nutrient levels occurs. The top thirty-two isolates performing in the deep well plate screen of PSGHL and the parent *S. stipitis* (control) are next screened twice in 16 mL flask cultures on SGH and SGH amended with two levels of nitrogen, SGH-N1 and SGH-N2. Isolates are picked from glycerol streaks to duplicate deep wells of 1 mL ODM+50 g/L xylose as described previously and incubated 48 hours in the Duetz System (Applikon Biotechnology, Inc., Foster City, Calif.). Then 50 µL of ODM precultures are transferred to 50% SGH challenge cultures which are incubated in the Duetz System (Applikon Biotechnology, Inc., Foster City, Calif.). The 50% SGH is prepared by mixing SGH 1:1 with sugarless ODM+50 g/L xylose (pH 5.6). Isolates are harvested after 72 hours from the 50% SGH challenge pre-cultures ($A_{620}$=approximately 10). For each isolate, 16 mL aliquot of SGH, SGH-N1, or SGH-N2 is inoculated with the cell pellet (15 minutes, 4900 rpm) from three wells of challenge culture to yield initial test culture ($A_{620}$=approximately 2.0). Test cultures are incubated at 25° C., 180 rpm (1" orbit) in 25-mL flasks with silicone sponge closures (Bellco Glass, Inc., Vineland, N.J.). Flasks are sampled and analyzed per the PSGHL screen as described above.

The top 21 isolates performing in the deep well plate screen of SGH and the parent *S. stipitis* control are next screened twice in 16 mL flask cultures on 6% glucan AFEX-CSH. Isolates are picked from glycerol streaks, placed in duplicate deep wells of 1 mL ODM+50 g/L xylose and incubated 48 hours using the Duetz System (Applikon Biotechnology, Inc., Foster City, Calif.). 3% glucan AFEX-CSH challenge medium (pH 5.0) is prepared by mixing 6% glucan AFEX-CSH 1:1 with water and is used to inoculate with 50 µL ODM preculture/well and then are incubated in the Duetz system. Cells of each isolate are harvested after 72 hours from challenge pre-cultures ($A_{620}$=approximately 10). For each of the isolates, 16 mL aliquot of 6% glucan AFEX-CSH (pH 5.2) is inoculated with the cell pellet from three wells of challenge culture to yield initial test culture $A_{620}$=approximately 2.0. Test cultures are incubated as described above for the SGH screen.

Figure 8A:
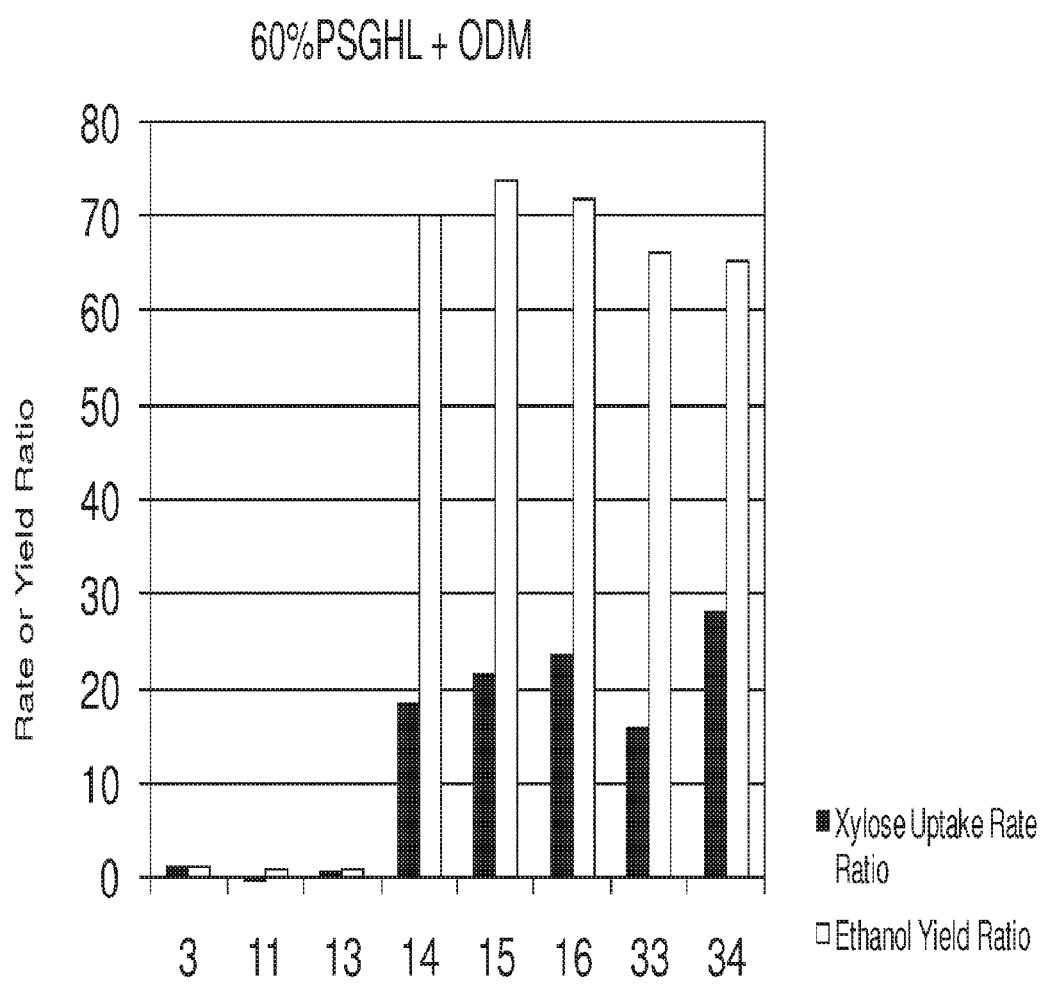
FIGS. 8A, 8B, 8C, and 8D show the performance of superior tolerant isolates (numbers given along x-axis) via the ratio to the corresponding performance of the control parent *S. stipitis* strain in 60% PSGHL+ODM (FIG. 8A), 75% PSGHL+ODM+YM (FIG. 8B), 60% PSGHL+ODM+75 g/L Glucose (FIG. 8C) and 75% PSGHL+ODM+YM+75 g/L Glucose (FIG. 8D). Performances are assessed in terms of xylose uptake rate and ethanol yield per sugar supplied.
Figure 8B:
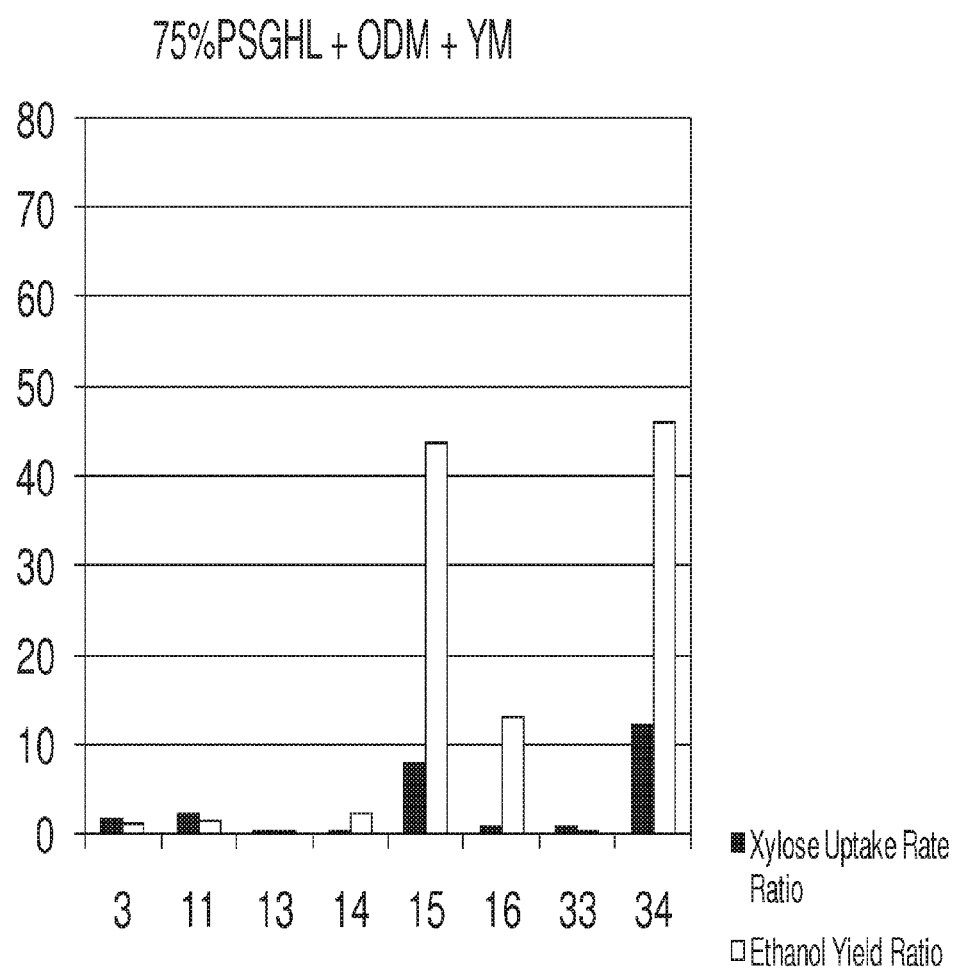
Figure 8C:
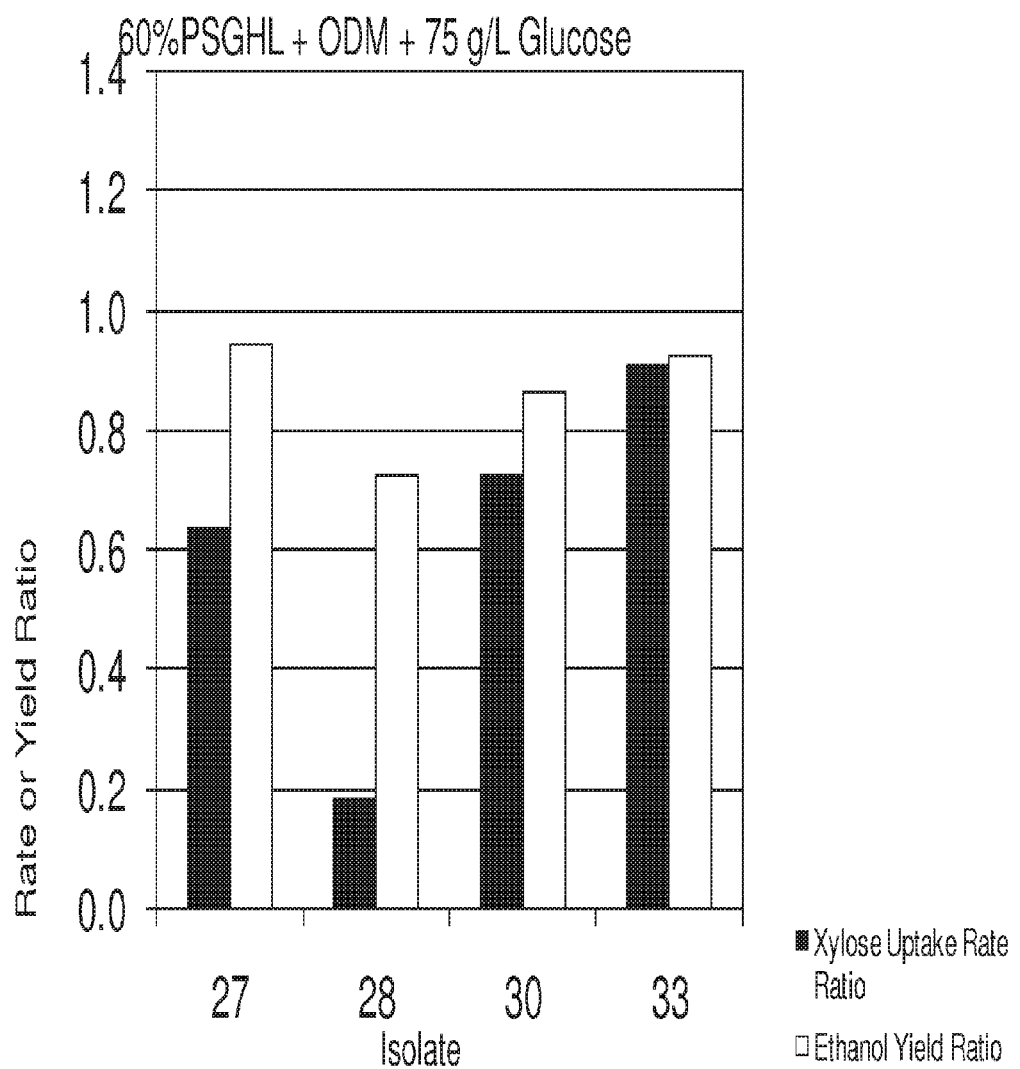
Figure 8D:
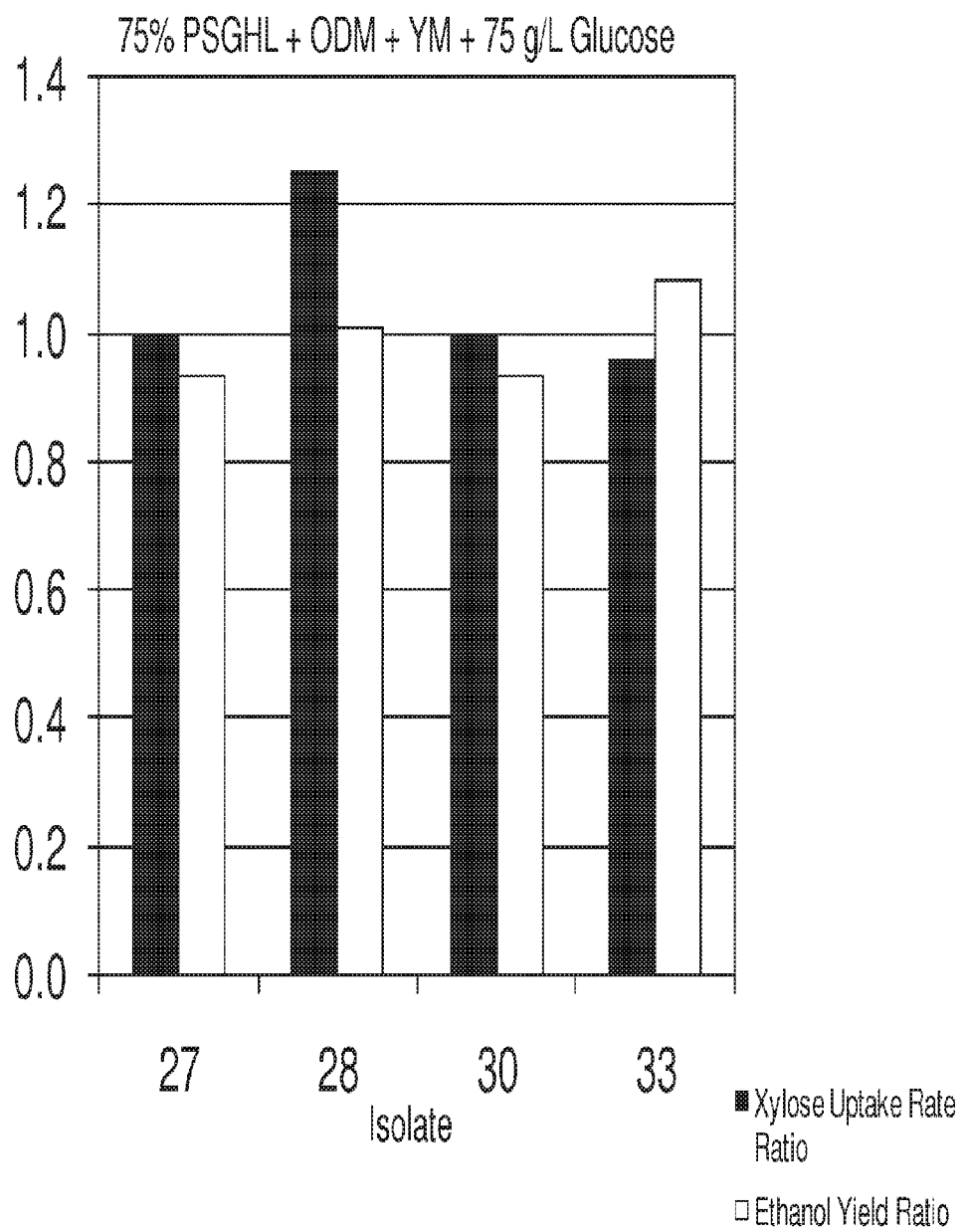

Isolates from all phases of the adaptation process are screened in PSGHL as the primary elimination point for those cultures not able to ferment xylose. The isolates chosen for representation in FIGS. 8A, 8B, 8C, and 8D are among the best performing yeast cells on PSGHL out of approximately 150 ranked in this primary screen and all secondary phases of performance ranking described below. In order to indicate improvement relative to the parent strain, the performance of each isolate is expressed as the ratio of isolate kinetic parameter value to parent strain *S. stipitis* kinetic parameter value. Ratio values of "one" occur if the isolate performance, based on either yield or xylose uptake rate, is equivalent to the parent. Ethanol yield per initial sugar available and xylose uptake rate ratios are used to rank relative performances of isolates. As the harshness of the hydrolyzate environment increases relative to adaptation exposure, the performance ratios became progressively smaller as shown in FIGS. 8A, 8B, 8C, and 8D, respectively. FIGS. 8A and 8B provide a summary of top isolate performances on 60% and 75% strengths of PSGHL with ODM and ODM+YM nutrient supplements, respectively. In the 60% strength PSGHL, five of seven top isolates exposed to PSGHL selection pressure perform many times better than the parent yeast cells (isolate 1), and four isolates perform slightly better than Colony 5 (isolate 33) which has evolved during exposure to AFEX-CSH but had no previous selective exposure to PSGHL. However, in the 75% strength of PSGHL, only 3 isolates significantly surpass both the parent yeast cells and Colony 5 (isolate 33). Isolates obtained from the continuous culture challenged with xylose growth in the presence of ethanol (isolates 27, 28, 30) are screened on the PSGHL medium supplemented also with 75 g/L glucose. Glucose is added to allow formation of enough ethanol to present an ethanol repression challenge to xylose utilization in order to detect isolates with the conserved reduced diauxy feature characteristic of the parent Colony 5 (isolate 33) from which they arose, as well as general ethanol resistance to cell damage. However, these isolates were not previously exposed to PSGHL, and, as shown in FIGS. 8C and 8D, they struggle to surpass par with the parent strain even when the nutrient environment is enriched with YM components.

When isolates passing the primary screen are submitted to a secondary screen on unamended SGH without any nitrogen supplementation, all isolates perform poorly, and there is no significant variation (P>0.05). Across the 33 isolates tested, including the parent S. stipitis strain, the kinetic parameter means and standard deviations are 0.19±0.1 g/g for ethanol yield per initial sugar and 0.10±0.03 g/L/h, for xylose uptake rate.

Figure 9:
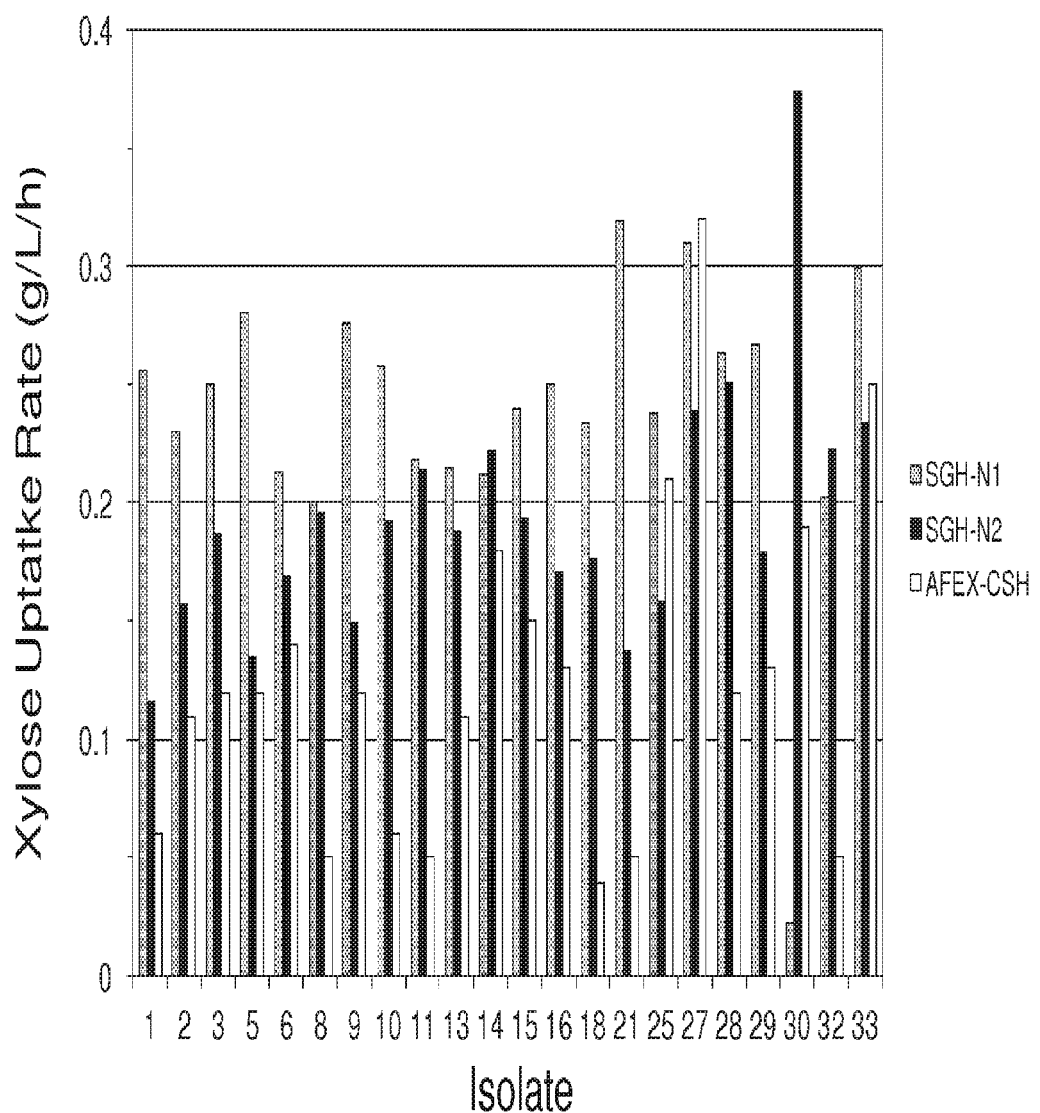
FIG. 9 demonstrates the significant dependence of xylose uptake rate on the interaction of isolate with hydrolyzate type ($P<0.001$). Isolates (identified along x-axis) are screened on two nutrient formulations of switchgrass hydrolyzate SGH-N1 and SGH-N2 and AFEX-pretreated cornstover hydrolyzate (AFEX-CSH) without nutrient supplement.

While carbon:nitrogen and PAN:ammonia content are easily measurable, the hydrolyzate environment is complex and likely to vary in inhibitor, amino acid, growth factor, and mineral profiles, which may potentially impact fermentations. The strategy for the secondary isolate screen is to apply all three nutritional environments in search of isolates with the flexibility to perform well and consistently despite the potential for nutritional and inhibitor variability to occur under commercial circumstances. A two-way ANOVA testing the impact of isolates x hydrolyzate types on yield and xylose uptake rate is carried out on data collected from hydrolyzate screen conducted in duplicate. When superior isolates passing the primary screen on PSGHL are evaluated on the three hydrolyzate types (SGH-N1, SGH-N2, and AFEX-CSH), the overall mean xylose uptake rate across isolates varies significantly between hydrolyzate types (P<0.001): 0.24 g/L/h for SGH-N1, 0.19 g/L/h for SGH-N2, and 0.12 g/L/h for AFEX-CSH. The relative xylose consumption rates among isolates are significantly dependent on the hydrolyzate type used in the screen, such that there is a nearly significant dependence on isolate (P=0.058) and a strongly significant interaction of isolate with hydrolyzate type impacting xylose uptake rate as shown in FIG. 9 (P<0.001). In contrast, the ethanol yield is not significantly impacted by hydrolyzate type (P=0.967) or isolate (P=1). The yield mean and standard deviation are 0.30±0.03 g ethanol/g initial ethanol per g initial sugar supplied. These data suggest that on average isolates preferred certain hydrolyzate types (SGH-N1>SGH-N2>AFEX-CSH). However, robust strains with flexibility to perform relatively well on all hydrolyzates can be identified using a ranking strategy.

Ranking of single-cell isolates from AFEX-CSH, ethanol, and dilute acid SGH adaptation phases is performed. Relative performance indices (RPI) are calculated in order to rank isolates in sets within a series of different experiments based on their relative performance in a variety of hydrolyzates and nutritional environments tested. RPI is a dimensionless value that is useful in combining data sets to use in overall ranking and/or statistical analysis of subjects submitted to various testing procedures. For this invention, yeast isolates are ranked based on ethanol yield per initial sugar available and xylose uptake rate within various experiment sets. Given that the parameters calculated for the performance of each isolate on each hydrolyzate are normally distributed across the group of isolates tested, the value of $F=(X-X_{avg})/s$ ranges from −2 to +2. Here, X designates yield (Y) or rate (R) observed per isolate, and $X_{avg}$ and s are the average and standard deviation, respectively, of all values observed for the group of isolate treatments within a given experiment, such as the testing of isolates on AFEX-CSH. $RPI=(2+F)\times 100/4$, such that the value of RPI ranges from approximately 0 to 100 percentile from lowest to highest rate or yield value, respectively. RPI averages for each isolate within a given hydrolyzate type trial are calculated as $RPI=(RPI_Y+RPI_R)/2$, where yield and rate contributions (subscripted Y and R, respectively) are given equal weighting. In general, different weights could be rationally assigned to the yield and rate contributions to the overall RPI average. Additionally, $RPI_{overall}$ is computed across the number of types of hydrolyzates tested (n): $RPI_{overall}=\Sigma[(RPI_Y+RPI_R)/2]_i/n$. During primary ranking of the approximately 150 single-cell isolates adapted to xylose-rich dilute acid-pretreated switchgrass hydrolyzate liquors (PSGHL), the $RPI_{overall}$ is calculated for rates and yields across the two PSGHL formulations applied in the screen, i.e., 60% PSGHL and 75% PSGHL. During secondary screening of the top 20% of isolates from the primary screen, the $RPI_{overall}$ is calculated for each of the isolates performing on three enzyme-saccharified pretreated hydrolyzate formulations including AFEX-CSH, SGH-N1 and SGH-N2, and this ranking parameter is applied to further winnow the list of superior isolates.

Figure 10A:
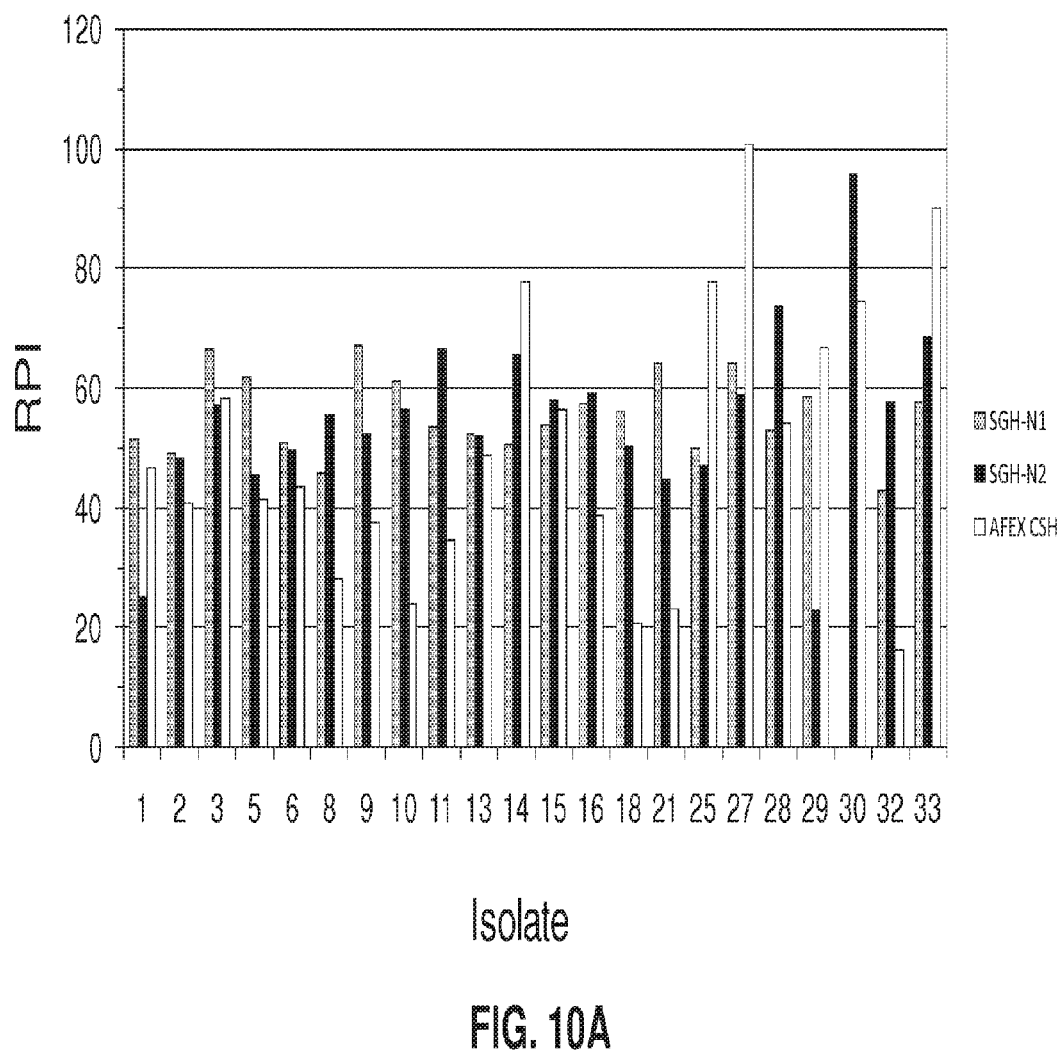
FIG. 10A shows the relative performance index (RPI) for 33 *S. stipitis* isolates within each hydrolyzate type based on xylose uptake rate and ethanol yield per sugar supplied.
Figure 10B:
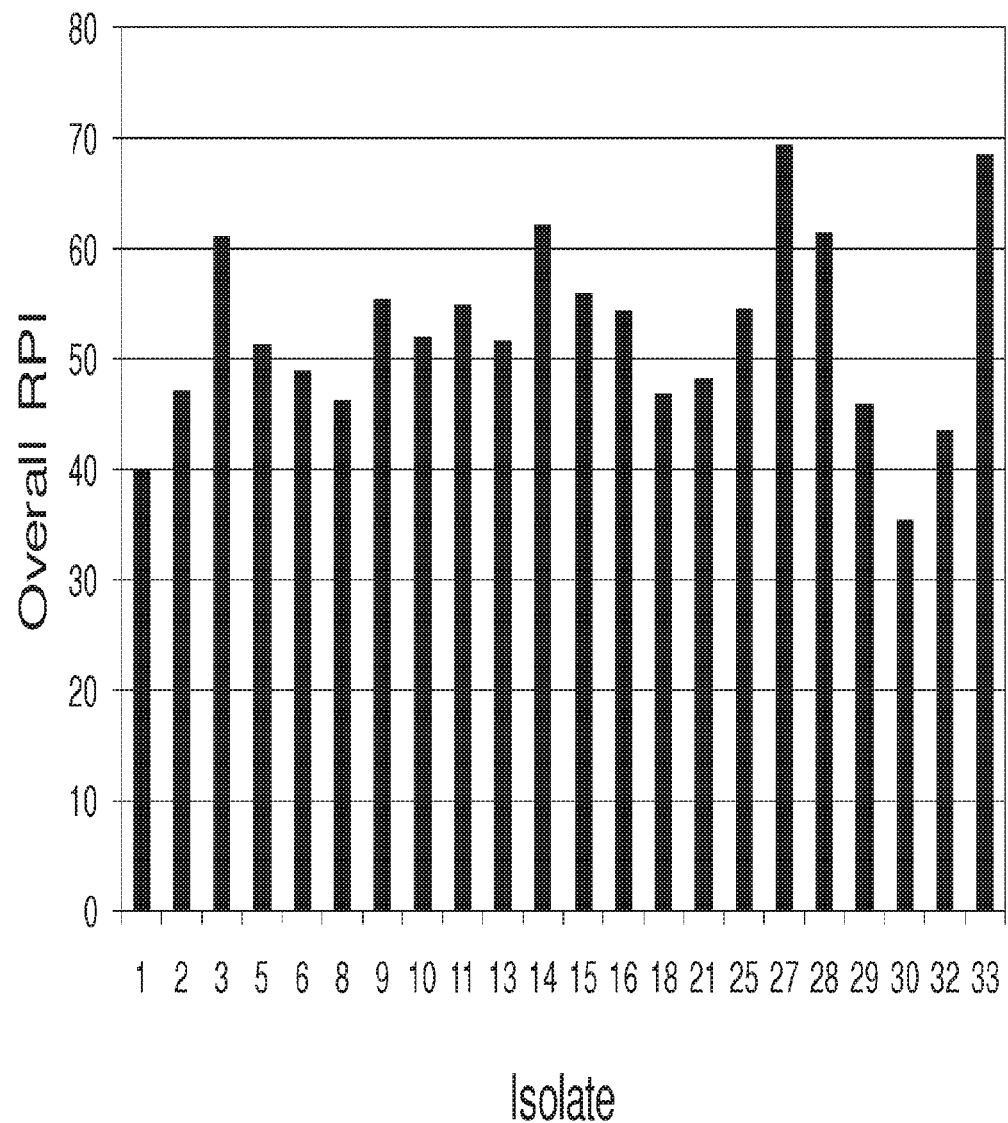
FIG. 10B shows the overall RPI calculated across all hydrolyzate types for the 33 *S. stipitis* isolates indicated as superior strains.
Figure 11A:
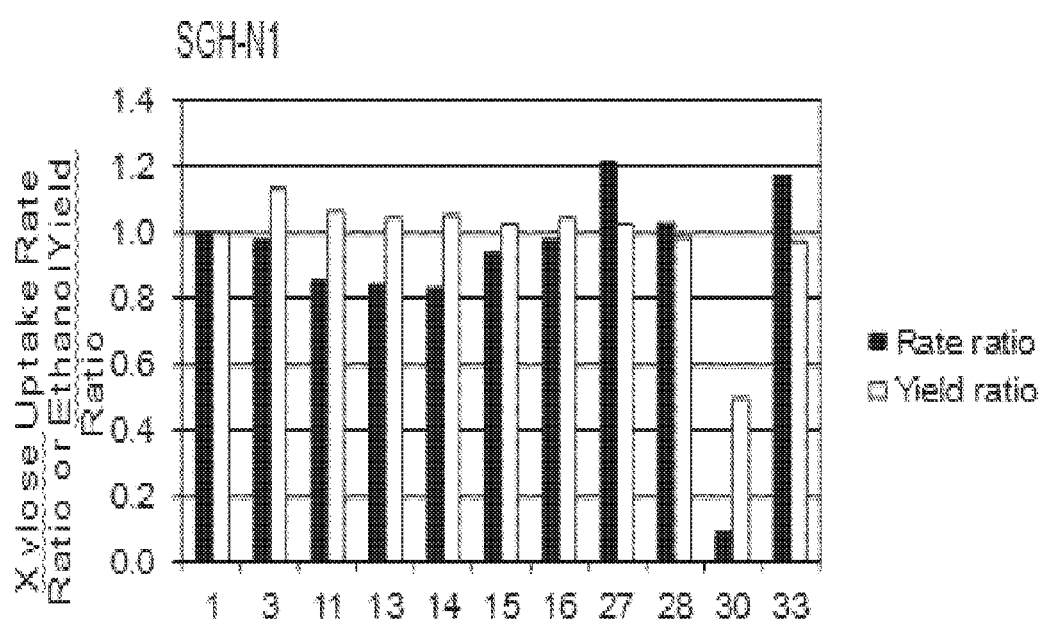
FIGS. 11A, 11B, and 11C show the performance of superior adapted *S. stipitis* isolates screened on three hydrolyzate types, including switchgrass hydrolyzate with two nutrient formulations, SGH-N1 (FIG. 11A) and SGH-N2 (FIG. 11B) and AFEX-CSH (FIG. 11C). The improvement in superior adapted isolates over the parent strain is hydrolyzate dependent and is indicated in terms of the xylose uptake rate ratio (dark bars) or the ethanol yield ratio (light bars), which are ratios of adapted strain to the parent strain kinetic parameter values.
Figure 11B:
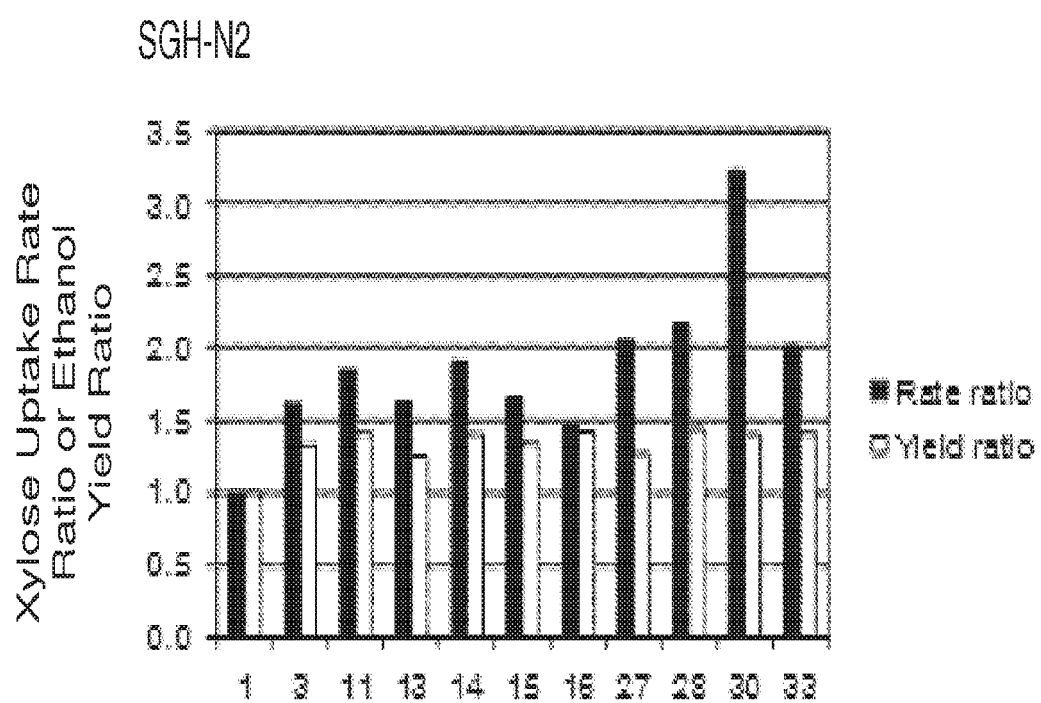
Figure 11C:
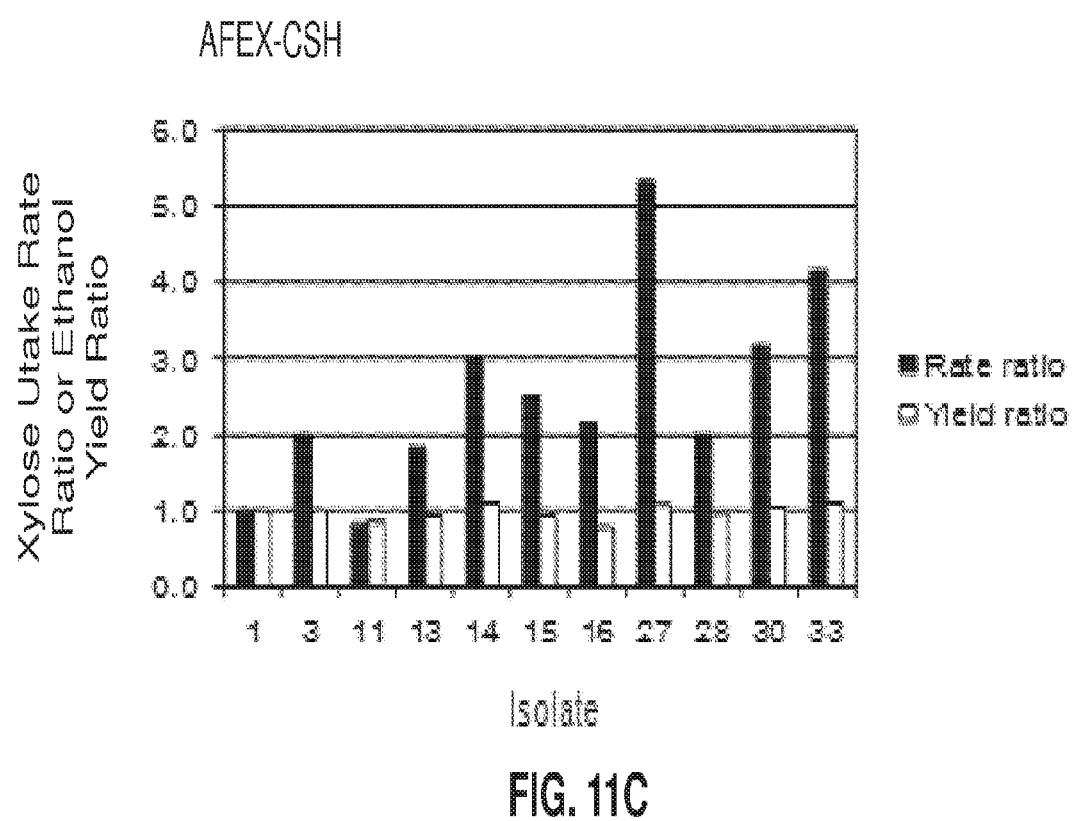

FIG. 10A shows RPI results within the three different hydrolyzate types for a selection of the better isolates among the 33 isolates tested in the secondary screen. A two-way ANOVA indicated significant variation in RPI due to isolate (P=0.003). Because RPI values are scaled within each hydrolyzate type relative to the data set mean and standard deviation, the mean RPI does not significantly vary among the three hydrolyzates tested (P=0.27), which had mean RPIs ranging from 50 to 55. However, the interaction of isolate with hydrolyzate type is strongly significant (P<0.001), and the relative ranking of isolates depends upon the type of hydrolyzate. This variation in ranking may exist because of variations in isolate nutritional requirements or inhibitor sensitivities, but it also may arise because of instability of certain isolates and inconsistencies even within the same type of hydrolyzate. The identification of isolates with highest overall RPI and lowest relative standard deviation among rankings on different hydrolyzates and replicates is a goal. Such isolates possess broad inhibitor tolerance, nutritional diversity, and genetic stability—all characteristics useful towards commercial robustness. Five such superior isolates with RPI>60 are indicated in FIG. 10B: 3, 14, 27, 28, 33. Another strategy is to identify any isolates that are specialists or that consistently rank highly RPI>55 within a hydrolyzate type or overall with a low relative standard deviation: 11 (SGH), 13, 15, 16 (SGH), 30 (SGH-N2) as indicated in Table 4 (infra) and FIG. 10. Most superior isolates fall within statistics group A or B, but isolate 30 is in group D because it is very good in SGH-N2 and AFEX-CSH but very poor in SGH-N1. FIGS. 11A, 11B, and 11C indicate the improvement of each of the superior isolates over the unadapted parent *S. stipitis* strain for each type of hydrolyzate, and show that isolate abilities are best separated by fermentation on AFEX-CSH and SGH-N2. AFEX-CSH supports the highest dynamic range of improvement in xylose uptake rate among isolates tested, but SGH-N2 supports the highest range of improvement in the ethanol yield per initial sugar supplied. Isolate abilities are not very distinguishable from one another on SGH-N1 (the least cost effective) perhaps because it is the least challenging as the most nutritionally fortified with added yeast extract, malt extract, amino acids, vitamins and minerals.

transfer from YM glycerol streaks to 200 mL ODM with 150 g/L xylose or 150 g/L glucose at pH 6 in 300 mL flasks with silicone sponge caps (Bellco Glass, Inc., Vineland, N.J.). Flasks are incubated at 150 rpm (1" orbit) for 96 hours at 25° C. Test cultures are inoculated to an $A_{620}=50$ using cell pellets from precultures in 12 mLs ODM+75 g/L xylose with 0-15 g/L acetic acid at pH 6.0. The 12 mL treatments are distributed 1 mL per well to 12 wells of a deep well plate and incubated in the Duetz System (Applikon Biotechnology, Inc., Foster City, Calif.).

To study impact of inhibitors on growth, liquid precultures are inoculated by sterile loop in 20 mL cultures of ODM with 50 g/L xylose (or glucose) at pH 6.0 in 50 mL flasks with silicone sponge caps (Bellco Glass, Inc., Vineland, N.J.). Flasks are incubated at 150 rpm (1" orbit) for 24 hours at 25° C. Test cultures are inoculated to an $A_{620}=0.1$ in duplicate wells containing 0.8 mL ODM+50 g/L

TABLE 4

| Screen number | Isolate designation | SGH-N1 and SGH-N2 | | | | SGH-N1, SGH-N2, and AFEX-CSH | | | |
|---|---|---|---|---|---|---|---|---|---|
| | | RPI Y/R average | s | Rel. s (%) | Statistic group | RPI Y/R average | s | Rel. s (%) | Statistic group |
| 1 | Y-7124 | 38.3 | 23.6 | 61.5 | D | 40.0 | 23.0 | 57.3 | C |
| 2 | Y7124 580E40-2 | 48.6 | 24.7 | 50.8 | C | 47.0 | 22.2 | 47.1 | C |
| 3 | Y7124 S90E40-1 | 61.8 | 15.6 | 25.2 | A | 61.1 | 14.7 | 24.0 | A |
| 4 | Colony 5 S90E40-5 | 40.1 | 12.6 | 31.5 | C | | | | |
| 5 | Colony 5 S100E40-5 | 53.6 | 11.8 | 22.0 | B | 51.1 | 12.3 | 24.0 | B |
| 6 | 2A.1.53R S90E40-4 | 54.0 | 19.0 | 35.2 | B | 48.8 | 12.4 | 25.5 | C |
| 7 | 2A.1.53R S100E40-5 | 52.3 | 16.6 | 31.7 | B | | | | |
| 8 | Y7124 GP-1 | 50.7 | 23.9 | 47.1 | B | 46.2 | 23.1 | 50.1 | C |
| 9 | Y7124 GP-5 | 59.8 | 15.7 | 26.3 | B | 55.3 | 17.6 | 31.9 | B |
| 10 | Colony 5 GP-2 | 58.9 | 10.1 | 17.2 | B | 51.9 | 17.4 | 33.5 | B |
| 11 | Colony 5 GP-6 | 59.9 | 15.4 | 25.8 | B | 54.8 | 17.7 | 32.3 | B |
| 12 | 2A.1.53R S90E40-2 | 34.2 | 17.1 | 50.1 | D | | | | |
| 13 | 2A.1.53R S100E40-1 | 52.2 | 10.5 | 20.1 | B | 51.5 | 9.5 | 18.4 | B |
| 14 | Y7124-6 | 58.2 | 16.2 | 27.9 | B | 62.1 | 17.0 | 27.3 | A |
| 15 | Y7124-10 | 57.6 | 6.6 | 11.4 | B | 55.9 | 6.7 | 11.9 | B |
| 16 | 2A.1.53R-1 | 58.3 | 10.2 | 17.4 | B | 54.4 | 14.0 | 25.8 | B |
| 17 | 2A.1.53R-6 | 49.4 | 13.1 | 26.5 | C | | | | |
| 18 | Colony 5-3 | 53.3 | 11.7 | 22.0 | B | 46.7 | 17.2 | 36.8 | C |
| 19 | Colony 5-4 | 41.6 | 16.7 | 40.1 | C | | | | |
| 20 | Y7124 GP3-1 | 32.0 | 18.2 | 56.8 | D | | | | |
| 21 | Y7124 GP3-5 | 54.4 | 18.9 | 34.7 | B | 48.1 | 21.2 | 44.1 | C |
| 22 | Colony 5 25%-2N | 46.8 | 29.3 | 62.6 | C | | | | |
| 23 | 2A.1.53R 25%-1N | 47.8 | 13.8 | 28.9 | C | | | | |
| 24 | 2A.1.53R 25%-2 | 51.5 | 16.7 | 32.4 | B | | | | |
| 25 | 2A.44R-E20-C1 | 48.6 | 15.4 | 31.7 | C | 54.4 | 18.4 | 33.8 | B |
| 26 | 2A.44R-E40-C2 | 55.0 | 29.7 | 54.0 | B | | | | |
| 27 | 2A.1.53R-E20-C1 | 61.5 | 23.7 | 38.6 | A | 69.3 | 27.7 | 39.9 | A |
| 28 | 2A.1.53R-E30-C3 | 63.3 | 17.6 | 27.9 | A | 61.4 | 16.2 | 26.4 | A |
| 29 | 2A.30R2-E30-05 | 40.5 | 52.9 | 130.6 | C | 45.8 | 48.5 | 105.9 | C |
| 30 | 2A.30R2-E40-05 | 25.5 | 81.4 | 319.3 | D | 32.3 | 74.7 | 231.4 | D |
| 31 | 3A.1.57-E20-C1 | 32.2 | 13.7 | 42.5 | D | | | | |
| 32 | 3A.1.57-E30-C1 | 50.2 | 11.2 | 22.3 | B | 43.4 | 17.7 | 40.8 | C |
| 33 | Colony 5 | 63.0 | 14.8 | 23.5 | A | 68.4 | 17.4 | 25.4 | A |

Isolates in bold are considered superior based on high overall RPI across hydrolyzate types, low relative standard deviation (Rel. s), and/or exceedingly high RPI on at least one hydrolyzate type as seen in FIG. 10A. Within columns, values with no letters in common are significantly different at P < 0.05 (Student-Newman-Keuls pairwise comparison method).

Example 5 Comparative Kinetics of Superior Isolates

Diauxy during glucose and xylose fermentation at low cell density ($A_{620,o}=0.1$) on ODM is evaluated using the protocols previously described for AFEX-CSH isolates, supra. Additionally, the impact of acetic acid on fermentation of ODM with mixed sugars and diauxy at high cell density is also evaluated. Precultures are inoculated by loop xylose (or glucose)+/−acetic acid or furfural inhibitors at pH 6.0 in 48 well MTP flower plates (part number MTP-48-BOHS; m2p-labs, Inc., Hauppauge, N.Y.). Test cultures are incubated at 25° C., 1100 rpm in a Biolector (m2p-labs, Inc., Hauppauge, N.Y.) which monitors light scattering.

For larger scale hydrolyzate fermentations in flasks for comparative kinetics, liquid precultures are inoculated by sterile loop to 75 mL cultures of ODM+50 g/L xylose in 125 mL flasks (silicone sponge caps; Bellco Glass, Inc., Vineland, N.J.) and incubated 48 hours, 150 rpm (1" orbit), 25° C. The 48 hours precultures are used to inoculate $A_{620}$=approximately 0.5 to 75 mL challenge cultures of 1:1 SGH-N2 and water (pH 6.2) which are incubated similarly in 125 mL flasks. Challenge cultures are harvested between approximately 72 hours and approximately 96 hours as required to obtain populations in the midst of xylose consumption. Test cultures are inoculated at $A_{620}$=8.4±2.5 to 75 mL SGH-N2 (pH 6.2) incubated in 125 mL flasks with silicone sponge caps (Bellco Glass, Inc., Vineland, N.J.) at 25° C., 150 rpm (1" orbit). For low initial cell density experiments, test cultures are inoculated to $A_{620}$=0.5 in 23 mL SGH-N2 per 50 mL flask.

Significant ethanol production occurs on AFEX-CSH prior to xylose uptake as evidenced by the presence of approximately 60 g/L glucose in this hydrolyzate which presents a challenge to induction of enzymes for xylose uptake. This situation may lead to loss of the trait after extended repetitive culturing of AFEX-CSH+/−E derivatives in PSGHL. However, 2 of 3 PSGHL stressed isolates gain a similar reduced diauxy phenotype. Repeated exposure to xylose among the other inhibitors present, such as acetic acid and furan aldehydes, may benefit the evolution process toward reduced diauxy but likely by different mechanisms than during exposure to AFEX-CSH. During PSGHL exposure, furfural and HMF could compete with xylose for reducing equivalents (Liu, et al., *J. of Industrial Microbiology and Biotechnology* 31, 345-352 (2004), Liu, et al., *Applied Biochemistry and Biotechnology* 121-124, 451-460 (2005); Weigert, et al., *Biotechnology Letters* 10, 895-900 (1988)) while acetate could cause cell damage, forcing the need for cells to metabolize xylose to accommodate repair of cell damage.

TABLE 5

| Adaptation stress | Isolate | | Sugar uptake rate (g/L/h) | | | | Ethanol productivity (g/L/h) | | | | Yield per initial sugar (g/g) | | | | | |
|---|---|---|---|---|---|---|---|---|---|---|---|---|---|---|---|---|
| | | | Glucose | | Xylose | | Glucose | | Xylose | | Ethanol | | Biomass | | Xylitol | |
| AFEX-CSH | 33 | Colony 5 | 1.08 | A | 0.38 | A | 0.48 | A | 0.14 | AB | 0.37 | A | 0.016 | BC | 0.018 | B |
| AFEX-CSH > E | 28 | 2A.1.53R-E30-C3 | 1.09 | A | 0.38 | A | 0.48 | A | 0.15 | A | 0.37 | A | 0.020 | AB | 0.018 | B |
| AFEX-CSH > E (UV) | 30 | 2A.1.30R2-E40-C5 | 1.10 | A | 0.38 | A | 0.48 | A | 0.13 | AB | 0.35 | AB | 0.022 | A | 0.029 | A |
| AFEX-CSH > E > PSGHL | 13 | 2A.1.53R-S100E40-1 | 0.96 | A | 0.30 | C | 0.41 | AB | 0.12 | ABC | 0.32 | BC | 0.014 | BC | 0.011 | C |
| AFEX-CSH > E > PSGHL | 16 | 2A.1.53R-1 | 1.05 | A | 0.27 | C | 0.41 | AB | 0.09 | C | 0.29 | C | 0.012 | CD | 0.015 | BC |
| AFEX-CSH > PSGHL | 11 | Colony 5-GP6 | 0.91 | A | 0.27 | C | 0.37 | B | 0.11 | BC | 0.30 | C | 0.010 | D | 0.010 | C |
| PSGHL | 3 | Y7124-S90E40-1 | 1.00 | A | 0.38 | A | 0.41 | AB | 0.15 | A | 0.35 | AB | 0.013 | CD | 0.026 | A |
| PSGHL | 14 | Y7124-6 | 0.97 | A | 0.34 | B | 0.38 | B | 0.13 | AB | 0.32 | BC | 0.017 | BC | 0.018 | B |
| PSGHL | 15 | Y7124-10 | 1.08 | A | 0.29 | C | 0.44 | AB | 0.11 | BC | 0.30 | C | 0.009 | D | 0.012 | C |
| Wild | 1 | Y7124 | 1.05 | A | 0.29 | C | 0.48 | A | 0.11 | BC | 0.34 | ABC | 0.019 | AB | 0.010 | C |

[1]With the exception of glucose uptake rate, all parameters varied significantly among isolates based on one-way ANOVA (P < 0.01) Within columns, values with no letters in common are significantly different at P < 0.05 (Student-Newman-Keuls pairwise comparison method).

utilization. After exposure to AFEX-CSH selection pressure, Colony 5 displays significantly reduced diauxic lag (see FIG. 3D). Consequently, the induction of xylose utilization in cultures inoculated to low initial cell densities ($A_{620,o}$=0.1) on ODM with 75 g/L each of xylose and glucose are evaluated on a selection of the superior strains in order to check the occurrence of the reduced diauxy phenotype in PSGHL-adapted isolates and its retention in derivatives of Colony 5 (AFEX-CSH) obtained after exposure to ethanol-challenged continuous cultures and/or PSGHL. The data summarized in Table 5 infra indicates that while glucose uptake rate remains the same among all isolates, the reduced diauxy trait is evidenced by faster xylose uptake rates (and higher ethanol productivities on xylose) in Colony 5 recovered from AFEX-CSH adaptation, both AFEX-CSH>E isolates with or without UV exposure, and two of three PSGHL-evolved strains. However the trait is notably lost from all AFEX-CSH treatments later exposed to repetitive culturing in PSGHL. Unlike AFEX-CSH, PSGHL is rich in xylose, high in furfural and acetate, but poor in glucose, and so during exposure, little selective pressure favoring reduced diauxy exists because <5 g/L ethanol forms prior to xylose Parent strain *S. stipitis* and hydrolyzate-tolerant derivatives show little difference in their abilities to grow on xylose or glucose in the presence of acetic acid at 6, 10, and 15 g/L (see Table 6 which shows comparative average resistance of superior isolates to acetic acid at 6, 10 and 15 g/L during growth on ODM with 50 g/L glucose or xylose). In the absence of acetic acid, specific growth rates (designated $\mu_o$) are similar among isolates, ranging from 0.23 to 0.28 per hour on glucose and from 0.22 to 0.26 per hour on xylose. However, a clear measure of inhibition by acetic acid is obtained by considering the ratio of specific growth rate in the presence of inhibitory acetic acid to that in the absence of acetic acid ($\mu_i/\mu_o$). The results of a three-way ANOVA conducted on the ratio of specific growth rates as a function of isolate, growth sugar, and acetic acid level reveal that cells growing on xylose are significantly more inhibited by acetic acid (growth rates reduced to 64% by 15 g/L acetic acid) than cells growing on glucose (growth rates reduced to just 79%). Isolate 30 (2A.1.30R2-E40-05) is significantly more resistant to acetic acid on xylose (average $\mu_i/\mu_o$=1.1) than all other strains and among the most resistant to acetic acid on glucose (average $\mu_i/\mu_o$=0.93). See Table 6.

TABLE 6

| Adaptation Stress | Isolate | Average $\mu_o$ (h$^{-1}$) | | Average Ratio $\mu_i/\mu_o$ | |
|---|---|---|---|---|---|
| | | Glucose | Xylose | Glucose | Xylose |
| AFEX-CSH | 33 Colony 5 | 0.23 AB | 0.23 A | 0.86 AB | 0.90 B |
| AFEX-CSH > E | 27 2A.1.53R-E20-C1 | 0.28 A | 0.26 A | 0.72 AB | 0.80 B |
| AFEX-CSH > E | 28 2A.1.53R-E30-C3 | 0.26 AB | 0.24 A | 0.75 AB | 0.68 B |
| AFEX-CSH > E (UV) | 30 2A.1.30R2-E40-C5 | 0.24 AB | 0.21 A | 0.93 AB | 1.10 A |
| AFEX-CSH > E > PSGHL | 13 2A.1.53R S100E40-1 | 0.26 AB | 0.25 A | 0.84 AB | 0.79 B |
| AFEX-CSH > E > PSGHL | 16 2A.1.53R-1 | 0.25 AB | 0.24 A | 0.88 AB | 0.75 B |
| AFEX-CSH > PSGHL | 11 Colony 5-GP6 | 0.22 B | 0.25 A | 1.02 A | 0.84 B |
| PSGHL | 3 Y7124 S90E40-1 | 0.25 AB | 0.22 A | 0.66 B | 0.83 B |
| PSGHL | 15 Y7124-10 | 0.25 AB | 0.24 A | 0.97 A | 0.85 B |
| PSGHL | 14 Y7124-6 | 0.23 AB | 0.23 A | 0.84 AB | 0.81 B |
| Wild | 1 Y7124 | 0.24 AB | 0.25 A | 0.96 AB | 0.87 B |
| | Significance | P = 0.039 | P = 0.223 | P < 0.01 | P < 0.001 |

| Acetic acid (g/L) | Average Ratio $\mu_i/\mu_o$ | |
|---|---|---|
| | Glucose | Xylose |
| 6 | 0.98 A | 0.98 A |
| 10 | 0.80 B | 0.89 B |
| 15 | 0.79 B | 0.64 C |
| Significance | P < 0.001 | P < 0.001 |

$\mu_o$ = initial specific growth rate in the absence of acetic acid;
$\mu_i$ = the specific growth rate in the presence of the inhibitory acetic acid. Within columns, values with no letters in common are significantly different at P < 0.05 (Student-Newman-Keuls pairwise comparison method).

Fermentation of 75 g/L xylose in ODM by large populations is significantly more inhibited as acetic acid increases from 5 g/L to 15 g/L. The level of inhibition is significantly higher when the cell populations are glucose-grown rather than xylose-grown, suggesting the increased difficulty of glucose using cells to switch to xylose utilization when under stress by acetic acid (see Tables 7 and 8). The overall impact of acetic acid across isolates is reflected by significant differences in xylose uptake rate, ethanol productivity, and ethanol yield. When strain populations are pre-grown on xylose, the xylose uptake and ethanol production rates and yields are higher than the parent *S. stipitis* cells for all strains that develop with AFEX-CSH stress. The three strains that received only PSGHL adaptation stress ferment xylose more slowly than the parent *S. stipitis* cells (see Table 7 which illustrates the comparative fermentation of 75 g/L xylose in ODM with 5-15 g/L acetic acid by isolates precultured on xylose). On the contrary, when the cell populations are grown on glucose, all strains that were exposed to only PSGHL adaptation stress ferment xylose significantly faster and at significantly higher ethanol yield (see Table 8 which shows the comparative fermentation of 75 g/L xylose in ODM with 5-15 g/L acetic acid by isolates precultured on glucose).

TABLE 7

| Adaptation stress | Isolate | Xylose uptake rate (g/L/hA)[1,2] | Ethanol productivity (g/L/hA)[1,2] | Ethanol yield per initial sugar (g/g)[2] |
|---|---|---|---|---|
| AFEX-CSH | 33 Colony 5 | 0.090 A | 0.0231 AB | 0.26 B |
| AFEX-CSH > E | 28 2A.1.53R-E30-C3 | 0.078 AB | 0.0197 ABC | 0.23 BCD |
| AFEX-CSH > E (UV) | 30 2A.1.30R2-E40-C5 | 0.071 BC | 0.0155 ABCDE | 0.20 DE |
| AFEX-CSH > E > PSGHL | 13 2A.1.53R S100E40-1 | 0.069 BC | 0.0249 A | 0.23 BCD |
| AFEX-CSH > E > PSGHL | 16 2A.1.53R-1 | 0.078 AB | 0.0175 ABCD | 0.25 BC |
| AFEX-CSH > PSGHL | 11 Colony 5-GP6 | 0.066 BC | 0.0141 BCDE | 0.21 CD |
| PSGHL | 3 Y7124 S90E40-1 | 0.043 D | 0.0080 DE | 0.14 F |
| PSGHL | 14 Y7124-6 | 0.053 CD | 0.0105 CDE | 0.16 EF |
| PSGHL | 15 Y7124-10 | 0.045 D | 0.0061 E | 0.30 A |
| Wild | 1 Y7124 W.T. | 0.060 C | 0.0148 BCDE | 0.19 DE |
| Acetic acid (g/L) | | | | |
| 5 | | 0.083 A | 0.0223 A | 0.29 A |
| 10 | | 0.065 B | 0.0152 B | 0.22 B |
| 15 | | 0.048 C | 0.0088 C | 0.14 C |

[1]Rates are normalized relative to population density in absorbance units (A) at 620 nm.
[2]Parameter variations based on two-way ANOVA (isolate × acetic) were significant (P < 0.001). Within columns, values with no letters in common are significantly different at P < 0.05 (Student-Newman-Keuls pairwise comparison method).

TABLE 8

| Adaptation stress | Isolate | | Xylose uptake rate (g/L/hA)[1,2] | Ethanol productivity (g/L/hA)[1,2] | Ethanol yield per initial sugar (g/g)[2] |
|---|---|---|---|---|---|
| AFEX-CSH | 33 | Colony 5 | 0.014 C | 0.0027 B | 0.09 C |
| AFEX-CSH > E | 28 | 2A.1.53R-E30-C3 | 0.018 C | 0.0039 B | 0.09 C |
| AFEX-CSH > E (UV) | 30 | 2A.1.30R2-E40-C5 | 0.029 BC | 0.0094 AB | 0.16 BC |
| AFEX-CSH > E > PSGHL | 13 | 2A.1.53R S100E40-1 | 0.021 C | 0.0047 B | 0.18 B |
| AFEX-CSH > E > PSGHL | 16 | 2A.1.53R-1 | 0.019 C | 0.0044 B | 0.16 BC |
| AFEX-CSH > PSGHL | 11 | Colony 5-GP6 | 0.014 C | 0.0049 B | 0.15 BC |
| PSGHL | 3 | Y7124 S90E40-1 | 0.058 A | 0.0165 A | 0.26 A |
| PSGHL | 14 | Y7124-6 | 0.044 AB | 0.0108 AB | 0.27 A |
| PSGHL | 15 | Y7124-10 | 0.050 A | 0.0141 A | 0.23 A |
| Wild | 1 | Y7124 | 0.018 C | 0.0050 B | 0.13 BC |
| Acetic acid (g/L) | | | | | |
| | | 5 | 0.043 A | 0.0126 A | 0.24 A |
| | | 10 | 0.028 B | 0.0071 B | 0.17 B |
| | | 15 | 0.014 C | 0.0032 C | 0.10 C |

[1]Rates are normalized relative to population density in absorbance units (A) at 620 nm.
[2]Parameter variations based on two-way ANOVA (isolate × acetic) were significant ($P < 0.001$). Within columns, values with no letters in common are significantly different at $P < 0.05$ (Student-Newman-Keuls pairwise comparison method).

Figure 12A:
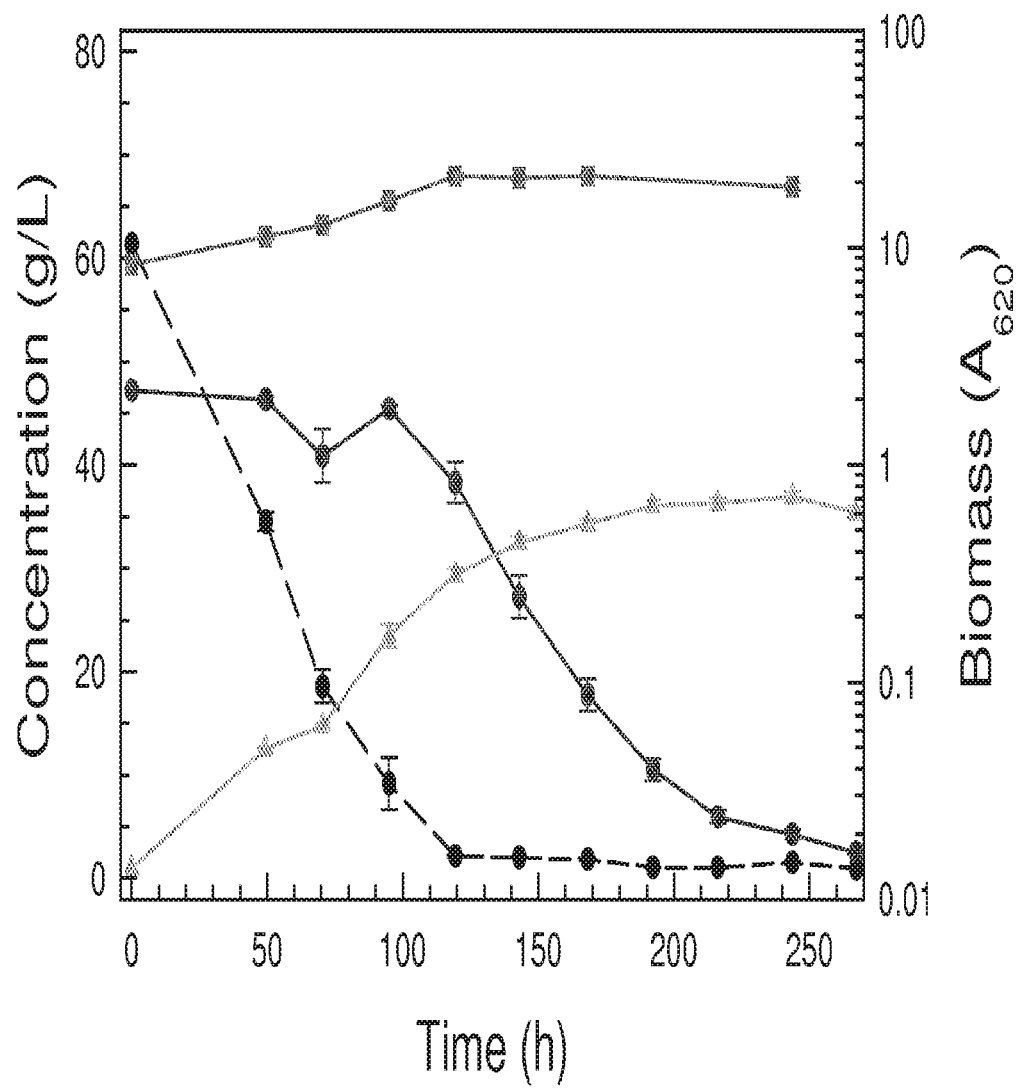
FIGS. 12A, 12B, 12C, 12D, 12E, 12F, 12G, 12H, 12I, and 12J shows the superior adapted strains of *Scheffersomyces stipitis* parent strain fermenting enzymatic hydrolyzates of dilute acid-pretreated switchgrass (20% solids loading) at 25° C. and initial pH 6.2 at high initial cell density for *S. stipitis* parent strain (FIG. 12A), Colony 5 (FIG. 12B), Y-7124-6 (FIG. 12C), and 2A.53R-E30-C3 (FIG. 12D), or low initial cell density *S. stipitis* parent strain (FIG. 12E), Colony 5 (FIG. 12F), Y-7124-6 (FIG. 12G), 2A.53R-E30-C3 (FIG. 12H), 2A.1.30R2-E40-05 (FIG. 12I) and 2A.1.53R-E20-C1 (FIG. 12J). Timecourses of biomass (squares), glucose (circles and dashed line), xylose (circles and solid line), and ethanol (triangles) are shown.
Figure 12B:
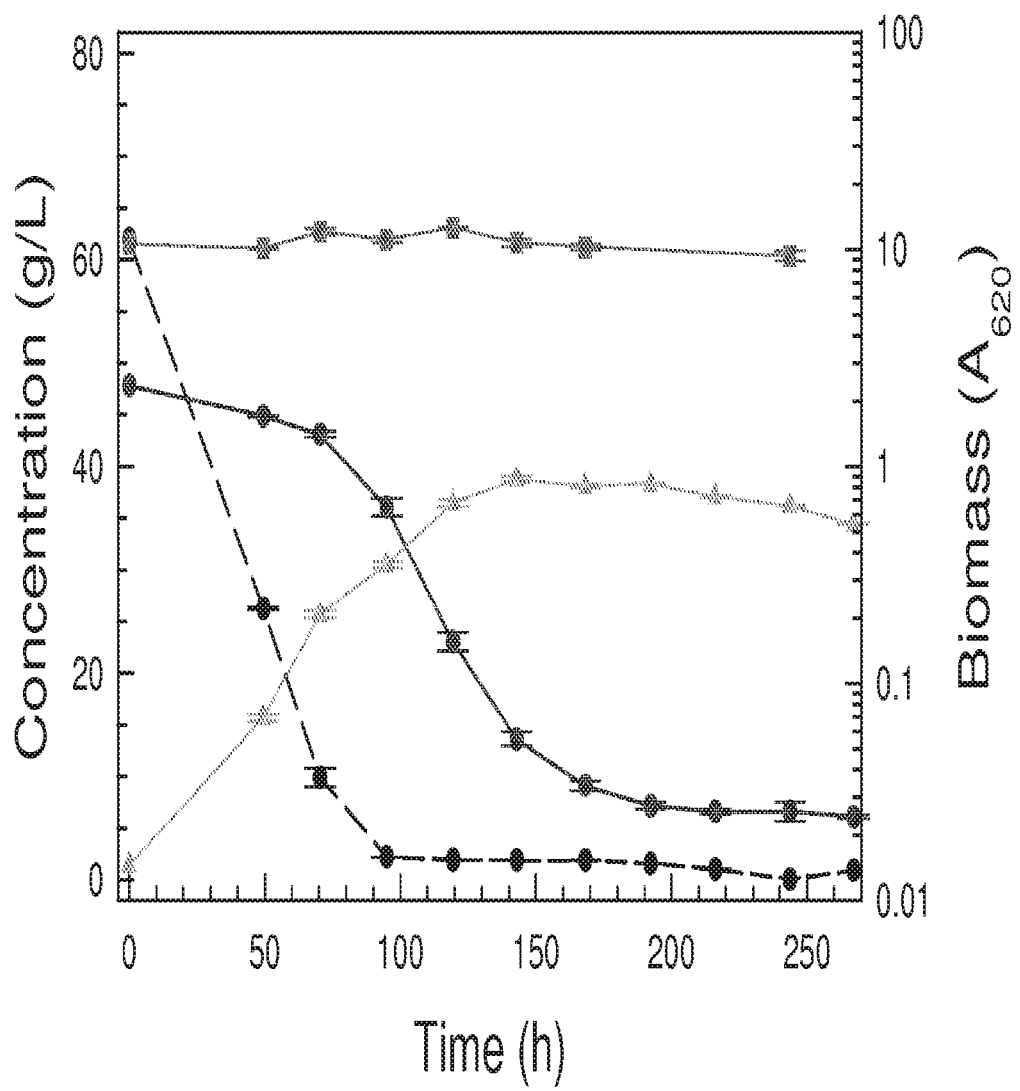
Figure 12C:
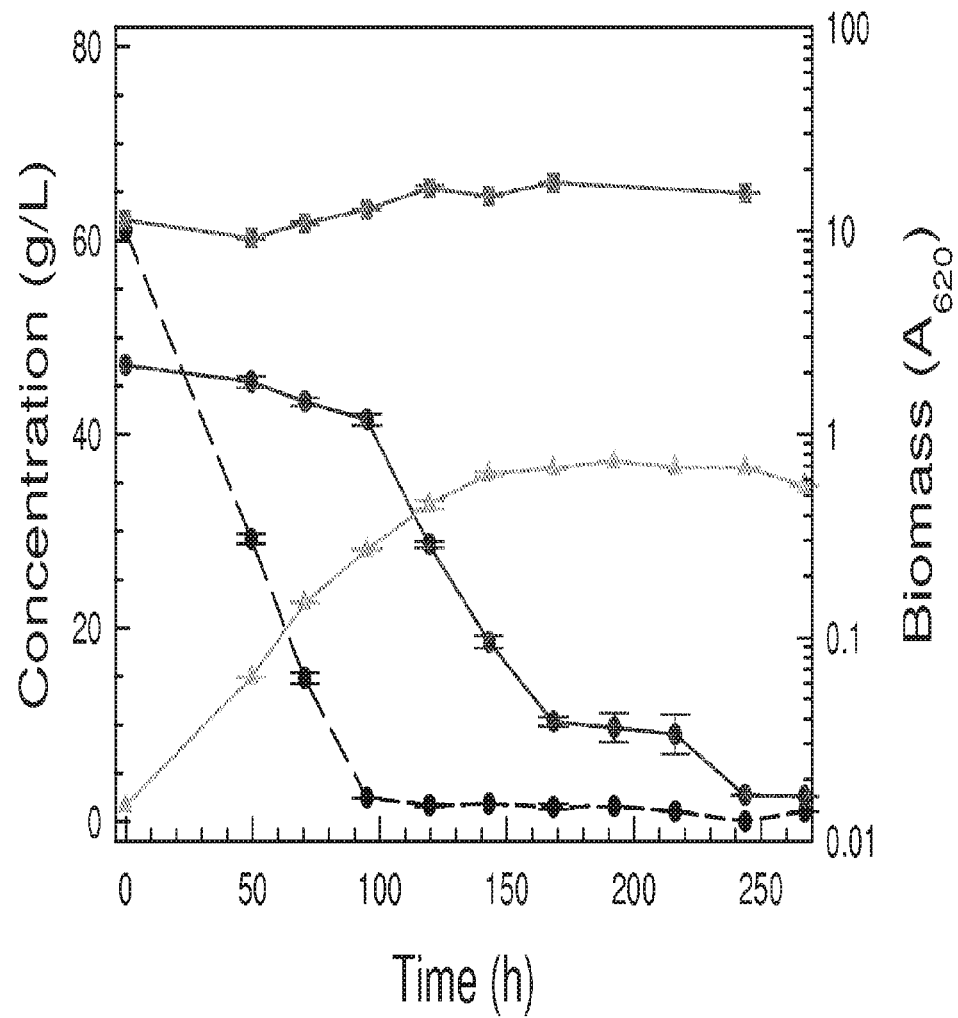
Figure 12D:
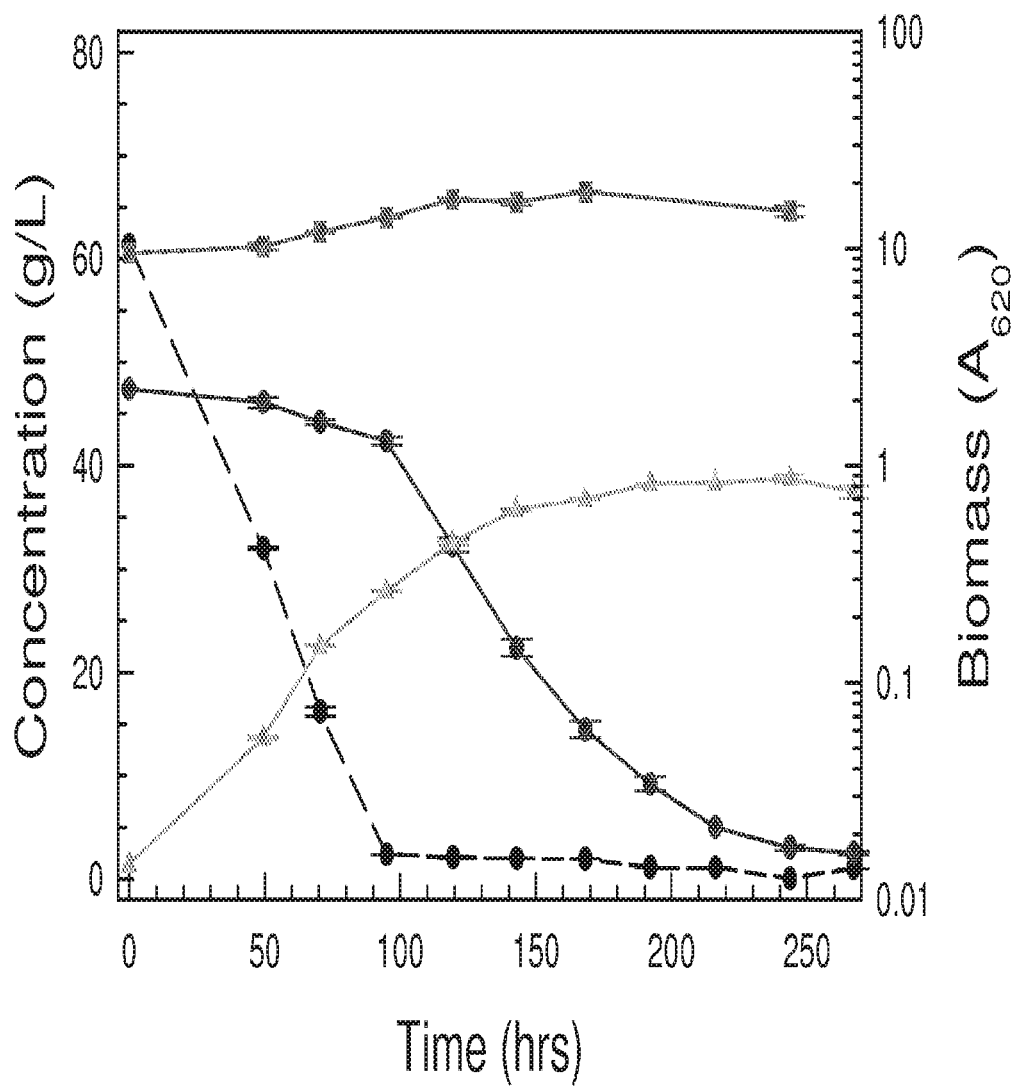
Figure 12E:
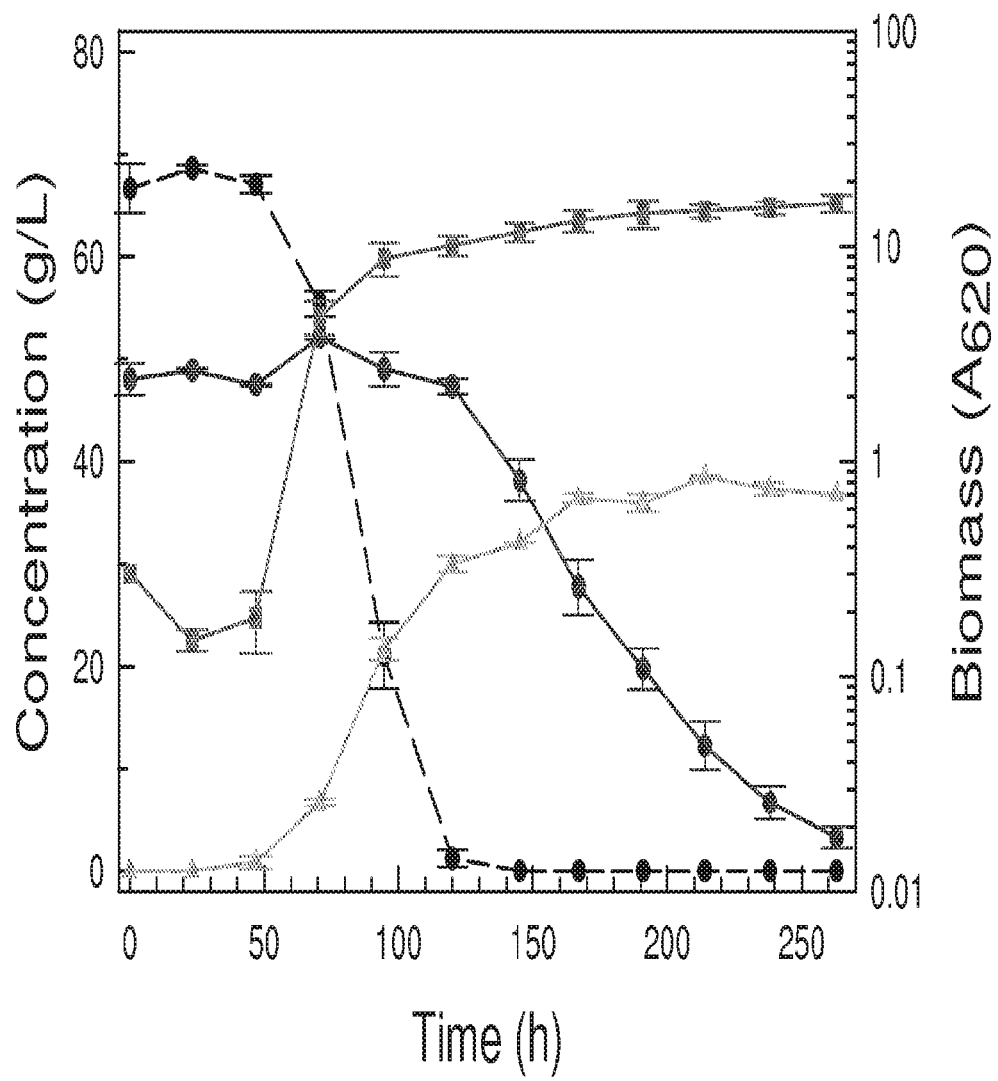
Figure 12F:
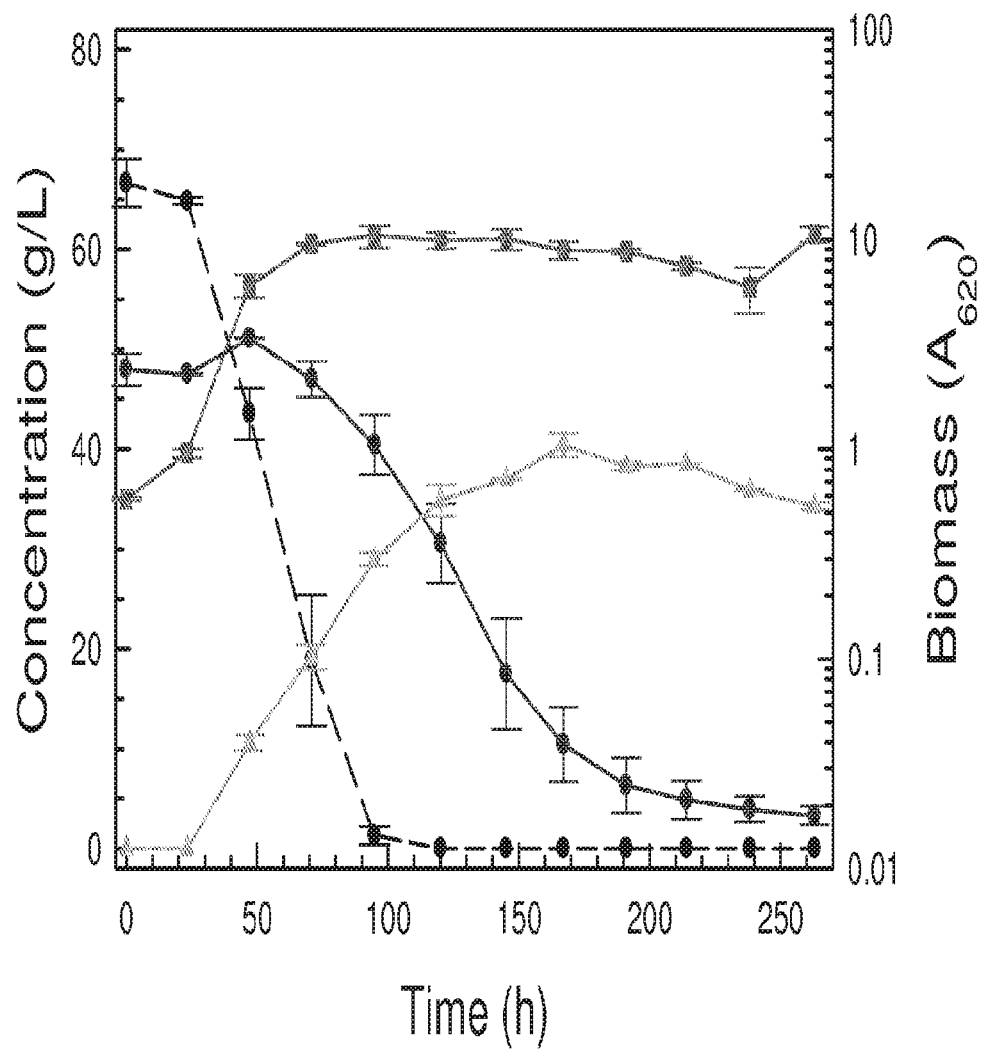
Figure 12G:
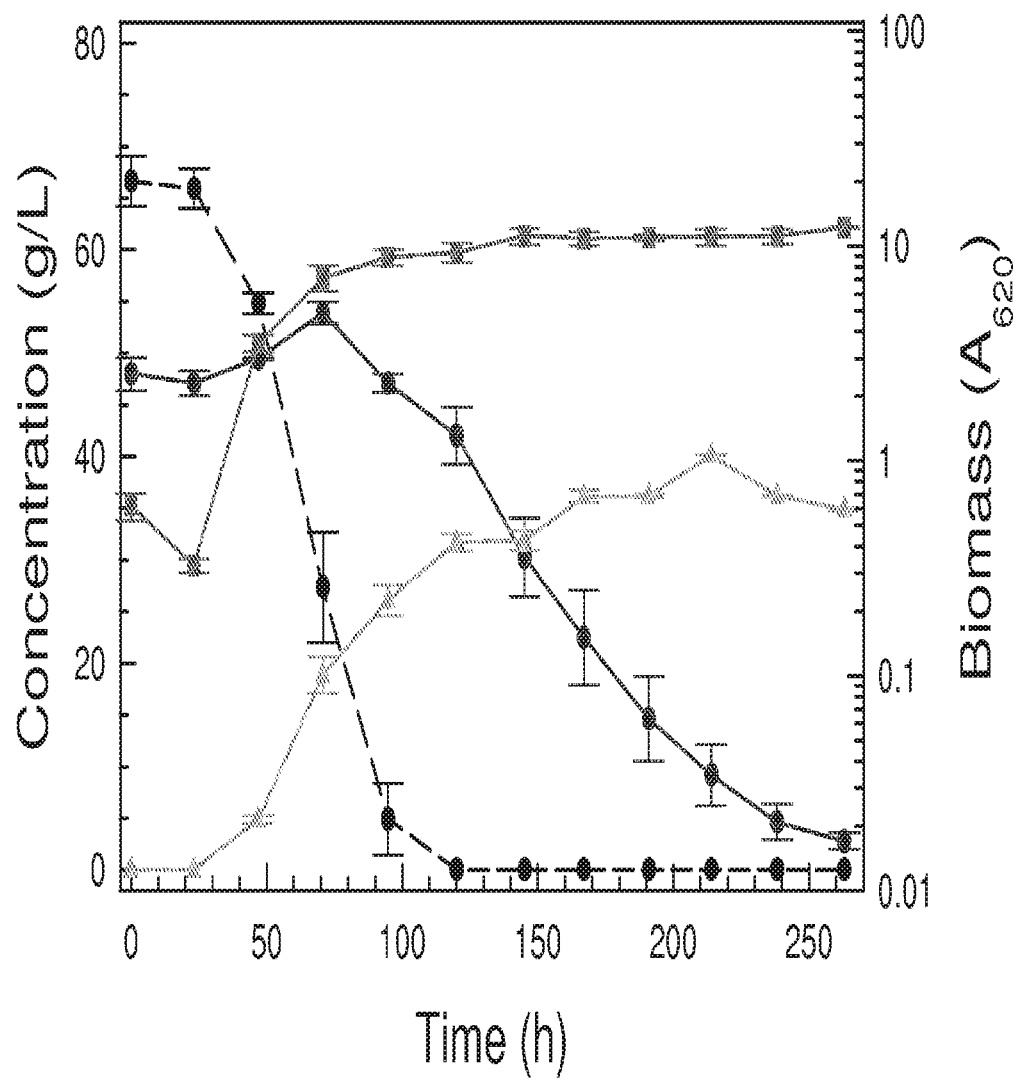
Figure 12H:
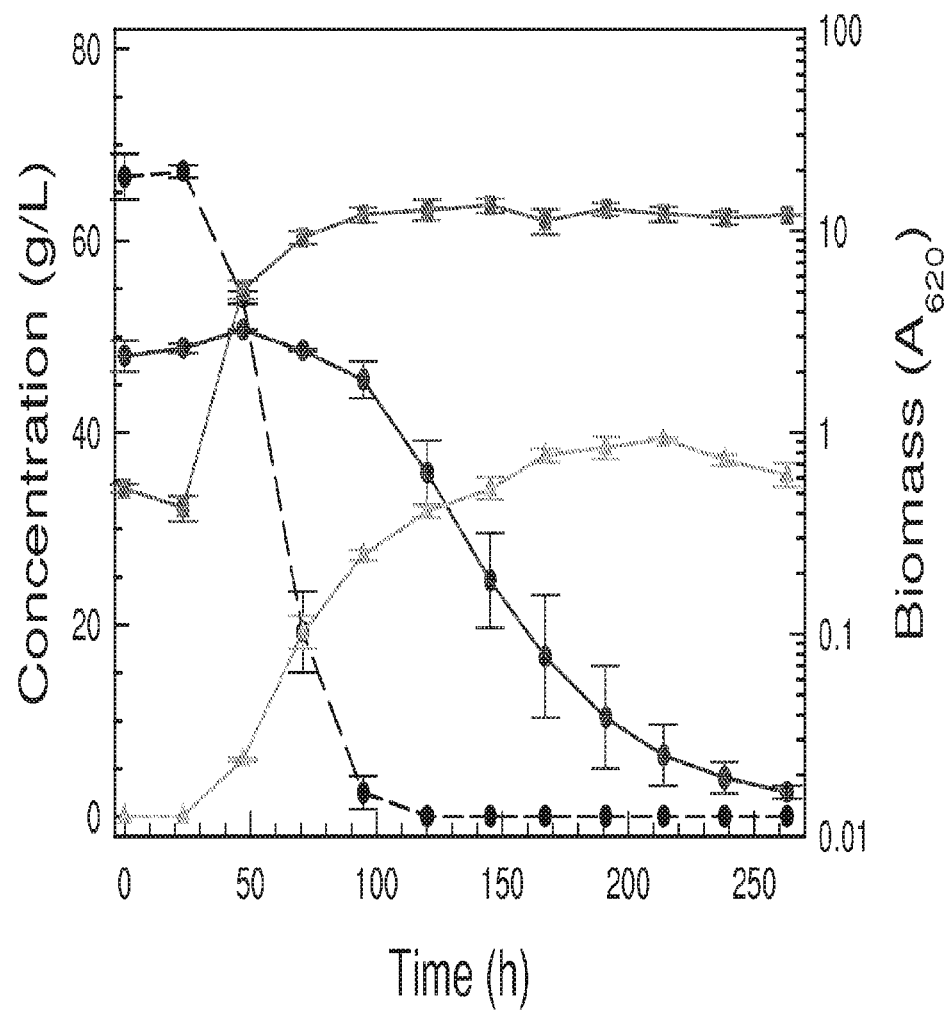
Figure 12I:
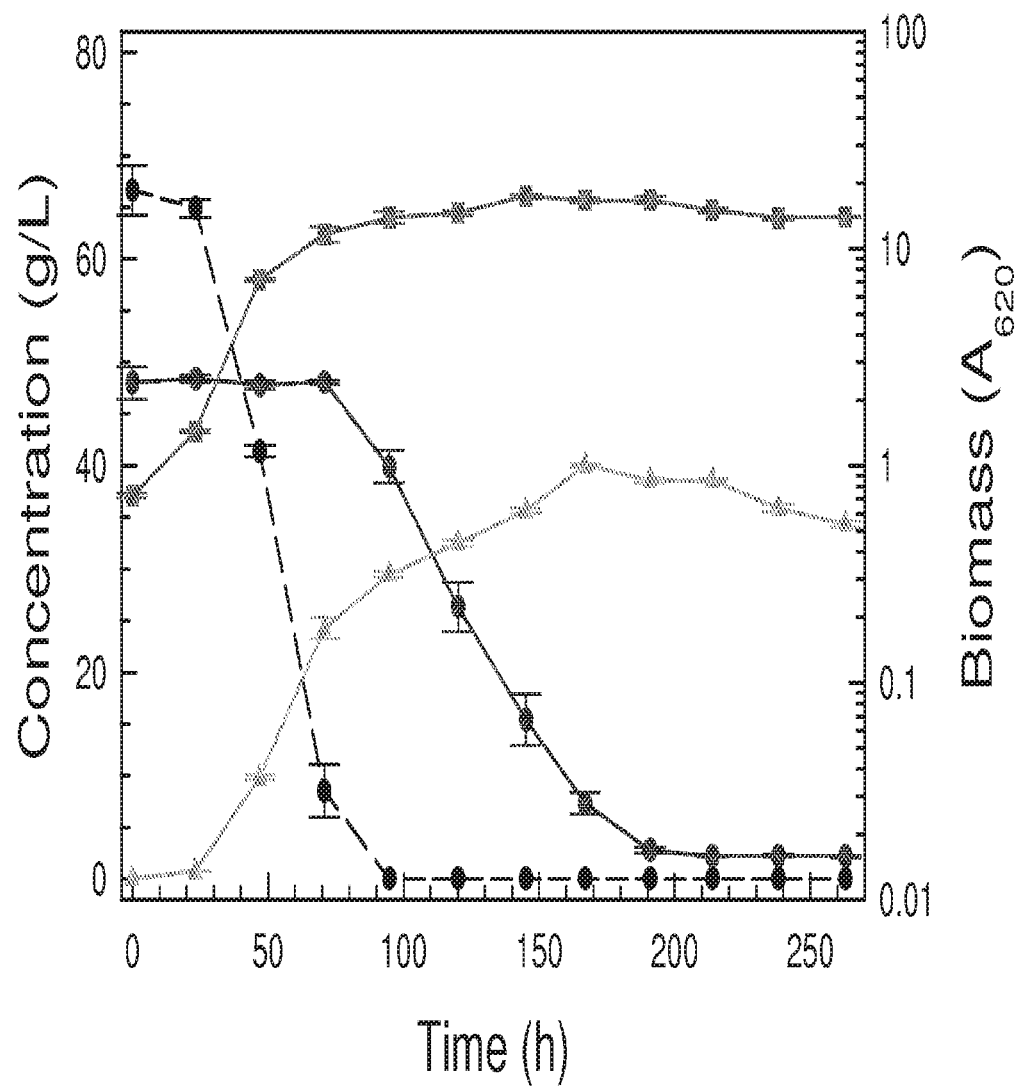
Figure 12J:
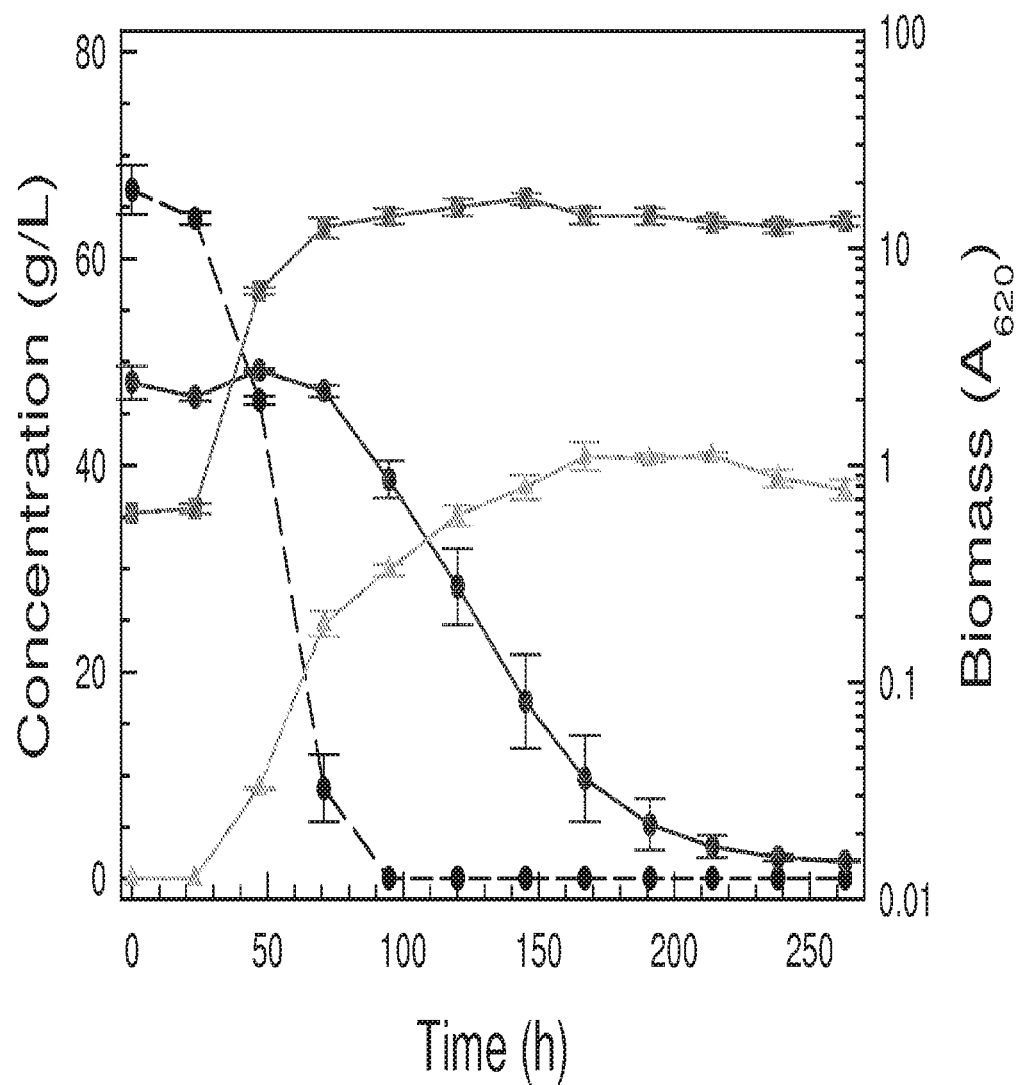

The furfural content of the PSGHL used in adaptation cultures is around 24 mM with little accompanying HMF (Table 1, supra). Furfural is typically reduced enzymatically with NADH cofactors by yeasts to less toxic furan methanol (Liu, et al. (2004); Liu, et al. (2005); Weigert, et al. (1988)). When the parent S. stipitis strain and hydrolyzate tolerant derivatives are challenged to grow in ODM+50 g/L glucose (or xylose) amended with 25 mM distilled furfural, all are able to survive and begin growing within approximately 32.8 hours to approximately 42.1 hours. It has been suggested that xylose and low level furan utilization may be compatible because the competition for NADH limiting xylitol accumulation (see, Hahn-Hagerdal, et al., Enzyme and Microbial Technology 16 (1994)). Statistical analysis of the results of these examples indicate some benefit of xylose shortening lag phase as a general trend across all isolates, but only by approximately 2.5 hours. Considering glucose as the growth substrate most likely to be encountered during detoxification lag, one exceptional isolate, 2A.1.30R2-E40-05 (AFEX-CSH>E (UV)) has a significantly shorter lag phase of approximately 32.7 hours compared with that of the parent S. stipitis strain at approximately 37.6 hours. It is also notable that the growth of isolate 2A.1.30R2-E40-05 is not reduced in the presence of up to 15 g/L acetic acid. These attributes give this strain (2A.1.30R2-E40-05) a competitive advantage in hydrolyzate fermentations as seen in FIG. 12I. Interestingly, strain 2A.1.30R2-E40-05 was exposed to AFEX-CSH, high levels of ethanol with xylose in extended continuous cultures, and UV irradiation during its development, but its exposures to furfural and acetate are only low to moderate during the hydrolyzate phase, suggesting that its adaptive changes are generally useful to coping with stress from inhibitors. Additionally, the finding that most adapted isolates are not, in general, especially faster at detoxifying furfural in defined medium compared with parent S. stipitis strain suggests that other attributes and mechanisms are involved in aiding their ability to cope in hydrolyzates.

When moderately high cell densities are applied initially to inoculate larger flask cultures with SGH-N2, almost all of the adapted strains that are ranked as "superior" are consuming sugars more quickly and producing ethanol more quickly on a volumetric rate basis. To reduce the influence of cell biomass variations resulting from growth advantages of some strains, especially during glucose consumption, rates are normalized based on the average absorbance reading during glucose or xylose uptake. This procedure further enhances statistical separation among strains, especially with respect to xylose uptake and ethanol productivity on xylose. This procedure indicates strain Y7124 S90E40-1 as having particularly high fermentation capacity on a specific rate basis although its ability to grow and accumulate biomass in the full strength hydrolyzate is weaker than for other strains. The ethanol yields of approximately 0.31 g/g to 0.34 g/g initial sugar supplied does not vary significantly among strains. In FIGS. 12A, 12B, 12C, and 12D, time courses are shown for the parent S. stipitis strain (FIG. 12A) and selected adapted strains representing the most successful adaptation schemes based on this cultivation application: Colony 5 (AFEX-CSH) (FIG. 12B), Y-7124-6 (PSGHL) (FIG. 12C), and 2A.53R-E30-C3 (AFEX-CSH>E) (FIG. 12D). Highest ethanol accumulations reached 39 g/L for adapted strains compared to 36 g/L for the parent strain.

A similar flask experiment is performed to compare kinetics in cultures inoculated to a low initial cell density. In this situation the ability of strains to grow in the hydrolyzate and transition to fermentation is tested. Time courses of the control and selected adapted strains are shown in FIGS. 12E, 12F, 12G, 12H, 12I, and 12J, and in this situation the parent strain, S. stipitis (FIG. 12E) performed particularly poorly relative to all of the adapted strains because it suffered a 48 hour lag period before growth began whereas the lag for adapted strains was much shorter at 24 hours or less. Highest ethanol accumulations reached are 42 g/L at 167 hours for adapted strains Colony 5 (FIG. 12F), Y-7124-6 (FIG. 12G), 2A.53R-E30-C3 (FIG. 12H), 2A.1.30R2-E40-05 (FIG. 12I), and 2A.1.53R-E20-C1 (FIG. 12J) compared to 38 g/L at 213 hours for the parent S. stipitis strain. For the adapted strains 85% of maximum ethanol accumulation is reached by 120 hours. The kinetics are the most favorable reported for high solids loading hydrolyzates inoculated with non-engineered yeast strains at pH 5-6 without prior detoxification.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

Recitation of ranges of values herein are merely intended to serve as a shorthand method of referring individually to each separate value falling within the range, unless otherwise indicated herein, and each separate value is incorporated into the specification as if it is individually recited herein. For example, if the range 10-15 is disclosed, then 11, 12, 13, and 14 are also disclosed. All numeric values provided herein include a 10% increase and a 10% decrease of that value. So, "ten" includes all numbers between "nine" and "eleven"; "one hundred" includes all numbers between "ninety" and "one-hundred ten". All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. All publications cited in this application are herein incorporated by reference.

We, the inventors, claim as follows:

1. An isolated *Scheffersomyces stipitis* strain having a shorter lag preceding growth phase when cultured on non-detoxified lignocellulosic hydrolysate compared to length of the lag preceding growth phase of *S. stipitis* cells ARS Culture Collection accession number NRRL Y-7124 when cultured on non-detoxified lignocellulosic hydrolysate, wherein said isolated *S. stipitis* strain produces at least 35 g/L ethanol when cultured on non-detoxified lignocellulosic hydrolysate, and wherein said isolated *S. stipitis* strain is selected from the group consisting of *S. stipitis* having ARS patent deposit accession numbers NRRL Y-50857, Y-50858, Y-50860, Y-50863, Y-50865, Y-50872, Y-50873, and Y-50874.

2. A method of producing ethanol comprising growing at least one of the isolated *Scheffersomyces stipitis* strains of claim 1 on lignocellulosic hydrolyzate for a period of time effective to allow said isolated *S. stipitis* strain to grow on said lignocellulosic hydrolyzate and ferment said lignocellulosic hydrolyzate to ethanol.

* * * * *